(12) United States Patent
Shibakawa et al.

(10) Patent No.: US 9,676,720 B2
(45) Date of Patent: Jun. 13, 2017

(54) SUBSTITUTED BIARYL COMPOUND

(71) Applicant: UBE INDUSTRIES, LTD., Ube-shi, Yamaguchi (JP)

(72) Inventors: Nobuhiko Shibakawa, Ube (JP); Kenji Yoneda, Ube (JP); Tetsushi Katsube, Ube (JP); Tomoko Kanda, Ube (JP); Koji Ito, Ube (JP); Kiyoshi Yamamoto, Ube (JP); Noriaki Iwase, Ube (JP); Shigeru Ushiyama, Ube (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 0 days.

(21) Appl. No.: 14/780,249

(22) PCT Filed: Mar. 28, 2014

(86) PCT No.: PCT/JP2014/059301
§ 371 (c)(1),
(2) Date: Sep. 25, 2015

(87) PCT Pub. No.: WO2014/157672
PCT Pub. Date: Oct. 2, 2014

(65) Prior Publication Data
US 2016/0060221 A1 Mar. 3, 2016

(30) Foreign Application Priority Data

Mar. 28, 2013 (JP) .................. 2013-069363
Nov. 1, 2013 (JP) .................. 2013-228489

(51) Int. Cl.
| C07D 213/74 | (2006.01) |
| A61P 11/00 | (2006.01) |
| A61K 31/444 | (2006.01) |
| A61P 43/00 | (2006.01) |
| A61K 31/4436 | (2006.01) |
| C07D 409/12 | (2006.01) |

(52) U.S. Cl.
CPC ......... C07D 213/74 (2013.01); C07D 409/12 (2013.01)

(58) Field of Classification Search
CPC .. C07D 409/12; C07D 417/14; C07D 213/74; A61K 31/444
USPC ........................................ 546/261
See application file for complete search history.

(56) References Cited

U.S. PATENT DOCUMENTS

| 8,648,097 B2* | 2/2014 | Iwamura ............ C07D 213/74 514/337 |
| 8,685,986 B2* | 4/2014 | Hagihara ............... A61K 31/44 514/256 |
| 2005/0124577 A1 | 6/2005 | Tani et al. |
| 2008/0045545 A1 | 2/2008 | Prasanna et al. |
| 2008/0114043 A1 | 5/2008 | Yamamoto et al. |
| 2011/0054172 A1 | 3/2011 | Iwamura et al. |
| 2012/0184747 A1 | 7/2012 | Iwamura et al. |
| 2012/0190852 A1 | 7/2012 | Hagihara et al. |
| 2012/0226036 A1 | 9/2012 | Hagihara et al. |
| 2012/0259123 A1 | 10/2012 | Iwamura et al. |
| 2014/0113907 A1* | 4/2014 | Iwamura ............ C07D 213/74 514/252.03 |
| 2016/0213657 A1* | 7/2016 | Yoneda ................ A61K 31/44 |

FOREIGN PATENT DOCUMENTS

| JP | 2009-544751 A | 12/2009 |
| WO | WO 98/28264 A1 | 7/1998 |
| WO | WO 99/19300 A1 | 4/1999 |
| WO | WO 03/074483 A1 | 9/2003 |
| WO | WO 2004/078169 A1 | 9/2004 |
| WO | WO 2005/080367 A1 | 9/2005 |
| WO | WO 2006/043655 A1 | 4/2006 |

(Continued)

OTHER PUBLICATIONS

Cameron; Bioorganic & Medicinal Chemistry Letters 2009, 19, 2075-2078.*

(Continued)

*Primary Examiner* — Noble Jarrell
*Assistant Examiner* — Daniel Carcanague
(74) *Attorney, Agent, or Firm* — Birch, Stewart, Kolasch & Birch, LLP

(57) ABSTRACT

The present invention provides a substituted biaryl compound of general formula (I):

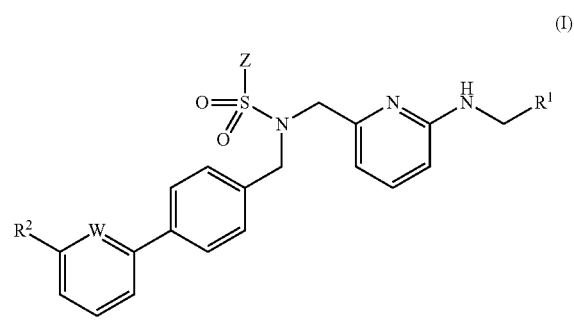

wherein, $R^1$, W, $R^2$, and Z are as defined in the claims and the description, or a pharmacologically acceptable salt thereof. The compound according to the present invention has an excellent inhibition effect of pulmonary fibroblast proliferation, and is therefore useful as a therapeutic agent and/or a prophylactic agent for interstitial pneumonia and pulmonary fibrosis.

7 Claims, No Drawings

(56) References Cited

FOREIGN PATENT DOCUMENTS

| | | |
|---|---|---|
| WO | WO 2007/017687 A2 | 2/2007 |
| WO | WO 2008/015517 A2 | 2/2008 |
| WO | WO 2008/065500 A2 | 6/2008 |
| WO | WO 2009/113600 A1 | 9/2009 |
| WO | WO 2010/113957 A1 | 10/2010 |
| WO | WO 2011/030864 A1 | 3/2011 |
| WO | WO 2011/030865 A1 | 3/2011 |
| WO | WO 2011/030868 A1 | 3/2011 |
| WO | WO 2011/030871 A1 | 3/2011 |
| WO | WO 2011/030872 A1 | 3/2011 |
| WO | WO 2011/030873 A1 | 3/2011 |
| WO | WO 2011/078303 A1 | 6/2011 |
| WO | WO2015030250 * | 3/2015 |

OTHER PUBLICATIONS

Bozyk et al., "Prostaglandin $E_2$ and the Pathogenesis of Pulmonary Fibrosis," American Journal of Respiratory Cell and Molecular Biology, vol. 45, 2011 (Originally Published in Press on Mar. 18, 2011), pp. 445-452.

Huang et al., "Prostaglandin $E_2$ inhibits collagen expression and proliferation in patient-derived normal lung fibroblasts via E prostanoid 2 receptor and cAMP signaling," Am J Physiol Lung Cell Mol Physiol, vol. 292, Feb. 2007 (First published Oct. 6, 2006), pp. L405-L413.

International Search Report (Form PCT/ISA/210) for International Application No. PCT/JP2014/059301, dated Jun. 17, 2014.

* cited by examiner

SUBSTITUTED BIARYL COMPOUND

TECHNICAL FIELD

The present invention relates to a novel substituted biaryl compound, or a pharmacologically acceptable salt thereof, that is useful as pharmaceuticals. More particularly, the substituted biaryl compound of the present invention is useful as a therapeutic agent and/or prophylactic agent for interstitial pneumonia and pulmonary fibrosis since the substituted biaryl compound has an excellent inhibition effect of pulmonary fibroblast proliferation.

BACKGROUND ART

Pulmonary fibrosis is characterized by hyperplasia of stromal cells due to formation of bundles of collagen and the like produced by proliferative fibroblasts in alveolar walls, and is a disease whose cardinal symptoms are dry cough and exertional dyspnea. This disease is caused by progression from interstitial pneumonia, and in many cases, interstitial pneumonia can be the preliminary symptom. Prognosis of interstitial pneumonia is poor and, in many cases, interstitial pneumonia progresses to pulmonary fibrosis. There are many cases where the interstitial pneumonia, in which the cause can be identified, is cured by removing the cause or by administering anti-inflammatory agents such as steroids; however, for the case of unexplained idiopathic interstitial pneumonia, no radical treatments currently exist, and treatments, such as administration of steroids, azathioprine, cyclophosphamide and the like when the symptoms worsen, and oxygen therapy when hypoxemia is caused, are performed at the best. If unexplained idiopathic interstitial pneumonia progresses to pulmonary fibrosis, about the half of the pulmonary fibrosis patients die within 5 years from occurrence of the symptoms. Because of this, interstitial pneumonia is designated as one of the specified intractable diseases in Japan.

On the other hand, it has been known that prostaglandin $E_2$ (hereinafter, abbreviated as "$PGE_2$") has a wide variety of bioactivities as a metabolic product in the arachidonic acid cascade, and acts as an agonist against four receptors that are EP1, EP2, EP3, and EP4. Recently, it has been reported that the EP2 receptor is a receptor that is related to inhibition of pulmonary fibroblast proliferation and collagen formation via $PGE_2$ (see Non-Patent Document 1). Furthermore, it has been suggested that the EP2 receptor is also a receptor that is related to inhibition of apoptosis of alveolar epithelial cells via $PGE_2$ (see Non-Patent Document 2). Therefore, a compound that exhibits agonistic effect like that of $PGE_2$, and in particular, a compound that exhibits effect of EP2 selective agonist is expected to be a therapeutic agent and/or prophylactic agent for interstitial pneumonia and pulmonary fibrosis.

So far, it has been disclosed that a prostanoid-based compound exhibiting EP2 agonistic effect is useful for prophylaxis and/or therapy of respiratory diseases including pulmonary fibrosis (see Patent Documents 1 and 2). Furthermore, a non-prostanoid-based compound exhibiting EP2 agonistic effect has been also known (see Patent Documents 3 to 17). Among these, various diseases that are exemplified as the targets of the medical use of the compounds described in Patent Documents 9 and 11 to 17 include pulmonary fibrosis. However, in Patent Documents 9 and 11 to 17, there are no specific descriptions regarding pharmacological test examples in which these compounds are useful for pulmonary fibrosis. Furthermore, there are no specific descriptions in any of these Patent Documents regarding working examples of a sulfonamide compound related to the present invention having, as its partial structure, a biaryl group in which a particular substituent is substituted at a particular part.

PRIOR ART DOCUMENTS

Patent Documents

Patent Document 1: WO2003/74483
Patent Document 2: WO2006/043655
Patent Document 3: WO98/28264
Patent Document 4: WO99/19300
Patent Document 5: WO2004/078169
Patent Document 6: WO2008/015517
Patent Document 7: WO2005/080367
Patent Document 8: WO2007/017687
Patent Document 9: WO2009/113600
Patent Document 10: WO2010/113957
Patent Document 11: WO2011/030864
Patent Document 12: WO2011/030865
Patent Document 13: WO2011/030868
Patent Document 14: WO2011/030871
Patent Document 15: WO2011/030872
Patent Document 16: WO2011/030873
Patent Document 17: WO2011/078303

Non-Patent Documents

Non-Patent Document 1: American Journal of Physiology-Lung Cellular and Molecular Physiology, 292, L405 (2007)
Non-Patent Document 2: American Journal of Respiratory Cell and Molecular Biology, 45, 445 (2011)

SUMMARY OF THE INVENTION

Problems to be Solved by the Invention

For the purpose of developing an excellent therapeutic agent and/or prophylactic agent for interstitial pneumonia and pulmonary fibrosis, the present inventors conducted intensive research on various sulfonamide compounds exhibiting EP2 agonistic effect. As a result, it was found that introduction of a particular substituent having a particular length to a particular part of a terminal aryl group of a sulfonamide compound having a biaryl group significantly increased the inhibition effect of pulmonary fibroblast proliferations, thereby making it particularly useful as a therapeutic agent and/or prophylactic agent for interstitial pneumonia and pulmonary fibrosis, and thus leading to completion of the present invention.

The present invention provides a substituted biaryl compound or a pharmacologically acceptable salt thereof that exhibits excellent inhibition effect of pulmonary fibroblast proliferation and, in particular, that exhibits EP2 agonistic effect that is useful as a therapeutic agent and/or prophylactic agent for interstitial pneumonia and pulmonary fibrosis.

Means for Solving the Problems

The present invention provides the following.
(1) A substituted biaryl compound of general formula (I):

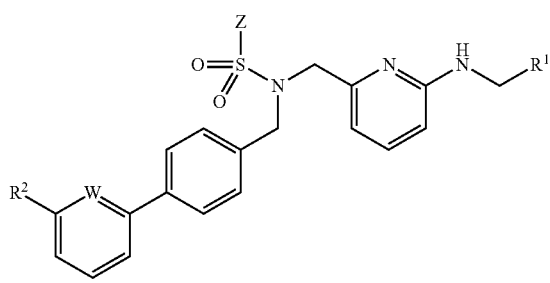

wherein
R¹ represents a protected or unprotected carboxy group,
W represents a nitrogen atom or —CH= group,
R² represents an ethoxy group, 1-propenyl group, or 1-propynyl group, and
Z represents a phenyl group, 3-fluorophenyl group, pyridin-2-yl group, pyridin-3-yl group, thiophen-2-yl group, or thiophen-3-yl group;
or a pharmacologically acceptable salt thereof.

(2) The substituted biaryl compound according to (1), where in general formula (I),
R¹ represents a carboxy group or $C_1$-$C_6$ alkoxycarbonyl group,
or a pharmacologically acceptable salt thereof.

(3) The substituted biaryl compound according to (1), where in general formula (I),
R¹ represents a carboxy group, ethoxycarbonyl group, isopropoxycarbonyl group, or hexyloxycarbonyl group,
or a pharmacologically acceptable salt thereof.

(4) The substituted biaryl compound according to (1), where in general formula (I),
R¹ represents a carboxy group, ethoxycarbonyl group, isopropoxycarbonyl group, or hexyloxycarbonyl group,
W represents a nitrogen atom or —CH= group,
R² represents a 1-propenyl group or 1-propynyl group, and
Z represents a phenyl group, 3-fluorophenyl group, pyridin-2-yl group, pyridin-3-yl group, thiophen-2-yl group, or thiophen-3-yl group, or a pharmacologically acceptable salt thereof.

(5) The substituted biaryl compound according to (1), where the substituted biaryl compound of general formula (I) is
ethyl (6-{[3'-(1-propenyl)biphenyl-4-ylmethyl](pyridin-2-ylsulfonyl)-aminomethyl}pyridin-2-ylamino)acetate,
(6-{[3'-(1-propenyl)biphenyl-4-ylmethyl](pyridin-2-ylsulfonyl)aminomethyl}-pyridin-2-ylamino)acetic acid,
ethyl (6-{[3'-(1-propynyl)biphenyl-4-ylmethyl](pyridin-2-ylsulfonyl)-aminomethyl}pyridin-2-ylamino)acetate,
(6-{[3'-(1-propynyl)biphenyl-4-ylmethyl](pyridin-2-ylsulfonyl)aminomethyl}-pyridin-2-ylamino)acetic acid,
ethyl (6-{[3'-(1-propynyl)biphenyl-4-ylmethyl](pyridin-3-ylsulfonyl)-aminomethyl}pyridin-2-ylamino)acetate,
(6-{[3'-(1-propynyl)biphenyl-4-ylmethyl](pyridin-3-ylsulfonyl)aminomethyl}-pyridin-2-ylamino)acetic acid,
{6-[(3'-ethoxybiphenyl-4-ylmethyl)(pyridin-2-ylsulfonyl)aminomethyl]-pyridin-2-ylamino}acetic acid,
hexyl {6-[(3'-ethoxybiphenyl-4-ylmethyl)(pyridin-2-ylsulfonyl)aminomethyl]-pyridin-2-ylamino}acetate,
{6-[(3'-ethoxybiphenyl-4-ylmethyl)(pyridin-3-ylsulfonyl)aminomethyl]-pyridin-2-ylamino}acetic acid,
{6-[(benzenesulfonyl)(3'-ethoxybiphenyl-4-ylmethyl)aminomethyl]pyridin-2-ylamino}acetic acid,
{6-[(3'-ethoxybiphenyl-4-ylmethyl)(thiophen-2-ylsulfonyl)aminomethyl]-pyridin-2-ylamino}acetic acid,
(6-{[4-(6-ethoxypyridin-2-yl)benzyl](pyridin-2-ylsulfonyl)aminomethyl}-pyridin-2-ylamino)acetic acid,
ethyl (6-{[3'-(1-propynyl)biphenyl-4-ylmethyl](thiophen-2-ylsulfonyl)-aminomethyl}pyridin-2-ylamino)acetate,
(6-{[3'-(1-propynyl)biphenyl-4-ylmethyl](thiophen-2-ylsulfonyl)-aminomethyl}pyridin-2-ylamino)acetic acid,
ethyl (6-{(benzenesulfonyl)[3'-(1-propynyl)biphenyl-4-ylmethyl]-aminomethyl}pyridin-2-ylamino)acetate,
(6-{(benzenesulfonyl)[3'-(1-propynyl)biphenyl-4-ylmethyl]aminomethyl}-pyridin-2-ylamino)acetic acid,
ethyl (6-{[3'-(1-propynyl)biphenyl-4-ylmethyl](thiophen-3-ylsulfonyl)-aminomethyl}pyridin-2-ylamino)acetate,
(6-{[3'-(1-propynyl)biphenyl-4-ylmethyl](thiophen-3-ylsulfonyl)-aminomethyl}pyridin-2-ylamino)acetic acid,
(6-{(3-fluorobenzenesulfonyl)[3'-(1-propynyl)biphenyl-4-ylmethyl]-aminomethyl}pyridin-2-ylamino)acetic acid, or
isopropyl (6-{[3'-(1-propynyl)biphenyl-4-ylmethyl](pyridin-2-ylsulfonyl)-aminomethyl}pyridin-2-ylamino)acetate, or a pharmacologically acceptable salt thereof.

(6) A pharmaceutical composition comprising the substituted biaryl compound according to any of (1) to (5), or a pharmacologically acceptable salt thereof, as an active ingredient.

(7) The pharmaceutical composition according to (6), for prophylaxis or treatment of interstitial pneumonia and/or pulmonary fibrosis.

Effect of the Invention

The substituted biaryl compound of general formula (I) or the pharmacologically acceptable salt thereof of the present invention is useful as pharmaceuticals, especially as a therapeutic agent and/or prophylactic agent for interstitial pneumonia and pulmonary fibrosis, by exhibiting EP2 agonistic effect and excellent inhibition effect of pulmonary fibroblast proliferation.

MODE FOR CARRYING OUT THE INVENTION

Preferred embodiments of each substituent in the substituted biaryl compound of general formula (I) above are described below.

The protected or unprotected carboxy group represented by R¹ of general formula (I) refers to a carboxy group or a carboxyl group protected by a protective group. Examples of such a protective group include ester-type protective groups. Examples of the partial structure of the ester-type protective group include $C_1$-$C_{12}$ alkyl groups, such as a methyl group, ethyl group, propyl group, isopropyl group, 1-ethylpropyl group, butyl group, isobutyl group, sec-butyl group, tert-butyl group, 3,3-dimethylbutyl group, pentyl group, isopentyl group, neopentyl group, tert-pentyl group, 1-methylbutyl group, hexyl group, 1-methylpentyl group, 2-methylpentyl group, 3-methylpentyl group, 1-ethylbutyl group, 2-ethylbutyl group, heptyl group, octyl group, nonyl group, decyl group, undecyl group, and dodecyl group; $C_7$-$C_{18}$ aralkyl groups, such as a benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, and phenyldodecyl group; $C_1$-$C_4$ alkyl groups substituted with a $C_2$-$C_5$ alkanoyloxy group, such as an acetoxymethyl group, 1-acetoxyethyl group, 1-acetoxypropyl group, 1-acetoxybutyl group, propanoyloxymethyl group, 1-propanoyloxyethyl group, butanoyloxymethyl group, 1-butanoyloxyethyl group, pivaloyloxymethyl group, 1-pivaloyloxyethyl group, 1-pivaloyloxypropyl group, and 1-pivaloyloxybutyl group; $C_1$-$C_4$ alkyl groups substituted with a ($C_1$-$C_4$ alkoxy)carbonyloxy group, such as a methoxycarbonyloxymethyl group, 1-methoxycarbonyloxyethyl group, ethoxycarbonyloxymethyl group, 1-ethoxycarbonyloxyethyl group, propoxycarbonyloxymethyl group, 1-propoxycarbonyloxyethyl group, isopropoxycarbonyloxymethyl group, 1-isopropoxycarbonyloxyethyl group, butoxycarbonyloxymethyl group, 1-butoxycarbonyloxyethyl group, tert-butoxycarbonyloxymethyl group, and 1-tert-butoxycarbonyloxyethyl group; N,N-dialkylaminocarbonylalkyl groups, such as an N,N-dimethylaminocarbonylmethyl group and N,N-diethylaminocarbonylmethyl group; 2-(N,N-dialkylamino)ethyl groups, such as a 2-(N,N-dimethylamino)ethyl group and 2-(N,N-diethylamino)ethyl group; $C_1$-$C_4$ alkyl groups substituted with a 5-membered or 6-membered saturated heteromonocyclic group having 1 or 2 hetero atoms selected from N, O, or S, such as a 2-(morpholin-4-yl)ethyl group, 2-piperidinoethyl group, and 2-(4-methylpiperidino)ethyl group; and groups that is readily deprotected in vivo to be converted to a carboxy group, such as a (5-methyl-2-oxo-1,3-dioxolen-4-yl)methyl group and (5-phenyl-2-oxo-1,3-dioxolen-4-yl)methyl group. The partial structure of the ester-type protective group is preferably a $C_1$-$C_{12}$ alkyl group, $C_7$-$C_{18}$ aralkyl group, $C_1$-$C_2$ alkyl group substituted with a $C_2$-$C_5$ alkanoyloxy group, $C_1$-$C_2$-alkyl group substituted with a ($C_1$-$C_4$ alkoxy) carbonyloxy group, N,N-dimethylaminocarbonylmethyl group, 2-(morpholin-4-yl)ethyl group, (5-methyl-2-oxo-1,3-dioxolen-4-yl)methyl group, or (5-phenyl-2-oxo-1,3-dioxolen-4-yl)methyl group. The partial structure of the ester-type protective group is more preferably a $C_1$-$C_6$ alkyl group, and particularly preferably an ethyl group, isopropyl group, or hexyl group.

Therefore, in general formula (I) of the present invention, $R^1$ is preferably a carboxy group or a $C_1$-$C_6$ alkoxycarbonyl group. In a specific embodiment of general formula (I) of the present invention, $R^1$ is a carboxy group, ethoxycarbonyl group, isopropoxycarbonyl group, or hexyloxycarbonyl group.

In general formula (I) of the present invention, W is a nitrogen atom or —CH= group. That is, in general formula (I) of the present invention, the aromatic ring containing W is a pyridine ring or benzene ring. In a specific embodiment of general formula (I) of the present invention, W is a —CH= group. In another specific embodiment of general formula (I) of the present invention, W is a nitrogen atom.

In general formula (I) of the present invention, $R^2$ is an ethoxy group, 1-propenyl group, or 1-propynyl group. In a specific embodiment of general formula (I) of the present invention, $R^2$ is an ethoxy group. In another specific embodiment of general formula (I) of the present invention, $R^2$ is a 1-propenyl group or 1-propynyl group.

In general formula (I) of the present invention, Z is a phenyl group, 3-fluorophenyl group, pyridin-2-yl group, pyridin-3-yl group, thiophen-2-yl group, or thiophen-3-yl group. In a specific embodiment of general formula (I) of the present invention, Z is a phenyl group, 3-fluorophenyl group, pyridin-2-yl group, or pyridin-3-yl group, and preferably a phenyl group, pyridin-2-yl group, or pyridin-3-yl group. In another specific embodiment of general formula (I) of the present invention, Z is a thiophen-2-yl group or thiophen-3-yl group, and preferably a thiophen-2-yl group.

When the compound of general formula (I) of the present invention has a geometrical isomer or a rotational isomer, these isomers are also included in the scope of the present invention. Furthermore, when the compound has a proton tautomer, such tautomer is also included in the scope of the present invention.

The compound of general formula (I) of the present invention can be converted to, as necessary, a pharmacologically acceptable salt by a conventional method; however, the pharmacologically acceptable salt can be also directly separated from the reaction mixture as a salt.

The compound of general formula (I) of the present invention is converted to a pharmacologically acceptable acid addition salt by treating it with an acid. Examples of such a salt include, for example, inorganic acid salts, such as hydrochloride, hydrobromide, hydroiodide, nitrate, sulfate, or phosphate; or organic acid salts, such as acetate, trifluoroacetate, benzoate, oxalate, malonate, succinate, maleate, fumarate, tartrate, citrate, methanesulfonate, ethanesulfonate, trifluoromethanesulfonate, benzenesulfonate, p-toluenesulfonate, glutamate, or aspartate.

When $R^1$ in the compound of general formula (I) of the present invention is a carboxy group, the compound is converted to a pharmacologically acceptable basic salt by treating it with a base. Examples of such a salt include metal salts, such as sodium salt, potassium salt, calcium salt, or magnesium salt; inorganic salts, such as ammonium salt; or organic amine salts, such as triethylamine salt or guanidine salt.

For cases where $R^1$ of the compound of general formula (I) of the present invention is a carboxy group protected by a protective group, when administered intravitally (in vivo test or the like), the compound is easily hydrolyzed by a biochemical reaction (e.g., esterase or the like) in vivo, and thus can be converted to a pharmacologically active compound in which $R^1$ is a carboxy group.

A representative method for producing the compound of the present invention is described below. Note that specific method for producing each compound of the present invention is described in detail in Examples described below.

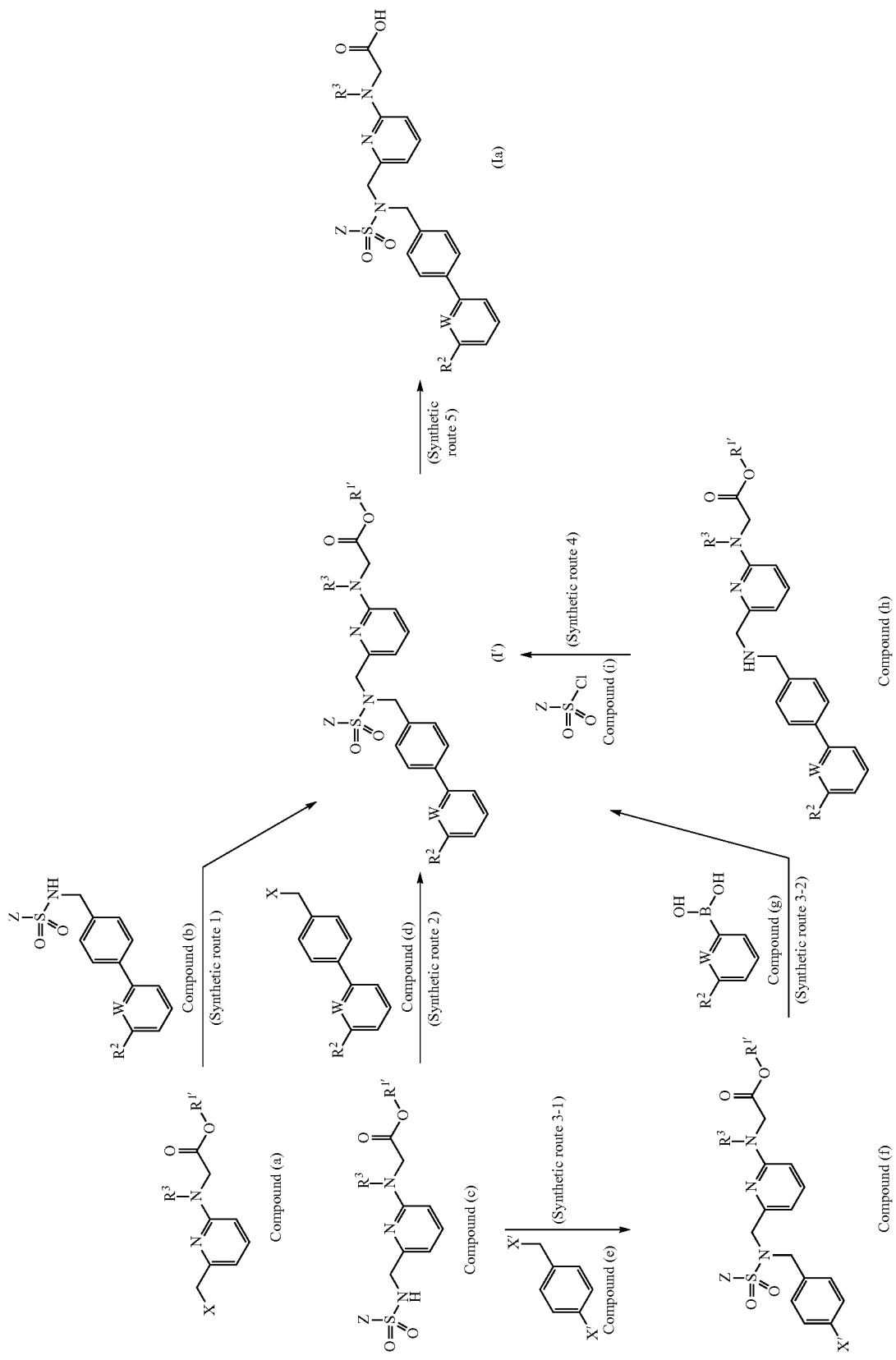

Wherein $R^2$, W, and Z are as defined in the above. $R^{1'}$ represents a protective group of the carboxy group, $R^3$ represents a tert-butoxycarbonyl group or hydrogen atom, X represents a hydroxy group, chloro group, bromo group, iodo group, methanesulfonyloxy group, benzenesulfonyloxy group, p-toluenesulfonyloxy group, or trifluoromethanesulfonyloxy group, and X' represents a chloro group, bromo group, or iodo group.

By any method of synthetic routes 1 to 4, the compound of general formula (I) of the present invention can be obtained as a compound (Ia) in which $R^3$ is a hydrogen atom for cases where $R^1$ is a carboxy group, or can be obtained as a compound (I') in which $R^3$ is a hydrogen atom for cases where $R^1$ is a carboxy group protected by a protective group.

Synthetic Route 1

When X is a hydroxy group in the compound (a), the compound (I') can be obtained by reacting the compound (a) with the compound (b) in an inert organic solvent in the presence of an azo compound-based condensing agent and a phosphine reagent.

The inert organic solvent used is not particularly limited as long as it does not inhibit the reaction and dissolves the raw materials at certain degrees. Examples of the inert organic solvent include aromatic hydrocarbons, such as benzene, toluene, and xylene; ethers, such as diethyl ether, tetrahydrofuran, 1,4-dioxane, and 1,2-dimethoxyethane; amides, such as N,N-dimethylformamide, N,N-dimethylacetamide, and N-methylpyrrolidone; nitriles, such as acetonitrile and propionitrile; esters, such as methyl acetate, ethyl acetate, and isopropyl acetate; and arbitrary mixed solvents thereof, and preferably tetrahydrofuran, N,N-dimethylformamide, acetonitrile, or a mixed solvent thereof.

Examples of the azo compound-based condensing agent used include diethyl azodicarboxylate (DEAD), diisopropyl azodicarboxylate (DIAD), N,N,N',N'-tetraisopropylazodicarboxamide (TIPA), 1,1'-(azodicarbonyl)dipiperidine (ADDP), N,N,N',N'-tetramethylazodicarboxamide (TMAD), or 1,6-dimethyl-1,5,7-hexahydro-1,4,6,7-tetrazocine-2,5-dione (DHTD), and preferably diethylazodicarboxylate (DEAD) or N,N,N',N'-tetramethylazodicarboxamide (TMAD). A molar amount of the azo compound-based condensing agent used is typically 0.9 to 10-fold, and preferably 1 to 5-fold based on 1 mole of the compound (b).

Examples of the phosphine reagent used include trimethylphosphine, triethylphosphine, tri-n-butylphosphine, or triphenylphosphine, and preferably tri-n-butylphosphine or triphenylphosphine. A molar amount of the phosphine compound used is typically 0.9 to 10-fold, and preferably 1 to 5-fold based on 1 mole of the compound (b).

A molar amount of the compound (a) used is typically 0.8 to 2-fold, and preferably 0.9 to 1.5-fold based on 1 mole of the compound (b).

Although varying depending on types and amounts used of raw materials, solvents, and the like, the reaction temperature is typically −20° C. to 100° C., and preferably −5° C. to 50° C.

Although varying depending on the reaction temperature and the like, the reaction time is typically 30 minutes to 48 hours, and preferably 1 hour to 24 hours.

When X in the compound (a) is a chloro group, bromo group, iodo group, methanesulfonyloxy group, benzenesulfonyloxy group, p-toluenesulfonyloxy group, or trifluoromethanesulfonyloxy group, the compound (I') can be obtained by reacting the compound (a) with the compound (b) in an inert organic solvent in the presence of a base.

The inert solvent used is not particularly limited as long as it does not inhibit the reaction and dissolves the raw materials at certain degrees. Examples of the inert solvent include ethers, such as tetrahydrofuran, 1,4-dioxane, and 1,2-dimethoxyethane; halogenated aliphatic hydrocarbons, such as methylene chloride, chloroform, and 1,2-dichloroethane; nitriles, such as acetonitrile and propionitrile; esters, such as methyl formate, ethyl formate, methyl acetate, and ethyl acetate; aromatic hydrocarbons, such as benzene and toluene; amides, such as N,N-dimethylformamide, N,N-dimethylacetamide, and N-methylpyrrolidone; sulfoxides, such as dimethyl sulfoxide; and arbitrary mixed solvents thereof, and preferably tetrahydrofuran, N,N-dimethylformamide, methylene chloride, or 1,2-dichloroethane.

Examples of the base used include alkali metal hydrides, such as sodium hydride and potassium hydride; alkali metal amides, such as lithium amide, sodium amide, lithium diisopropylamide, and lithium bis(trimethylsilyl)amide; alkali metal alkoxides, such as sodium methoxide, sodium ethoxide, sodium tert-butoxide, and potassium tert-butoxide; alkali metal carbonates, such as sodium carbonate and potassium carbonate; amines, such as triethylamine, tributylamine, diisopropylethylamine, pyridine, picoline, 2,6-lutidine, and 4-dimethylaminopyridine, and preferably sodium hydride, potassium carbonate, triethylamine, or diisopropylethylamine. However, when the inert solvent used is an ester, nitrile, or halogenated aliphatic hydrocarbon, the base is preferably triethylamine or diisopropylethylamine.

A molar amount of the base used is typically 1 to 5-fold, and preferably 1 to 2.5-fold based on 1 mole of the compound (b).

A molar amount of the compound (a) used is typically 0.5 to 3-fold, and preferably 0.5 to 1.5-fold based on 1 mole of the compound (b).

Although varying depending on types and amounts used of raw materials, solvents, and the like, the reaction temperature is typically −80° C. to 100° C., and preferably 0° C. to 80° C.

Although varying depending on the reaction temperature and the like, the reaction time is typically 10 minutes to 48 hours, and preferably 1 hour to 24 hours.

Synthetic Route 2

When X is a hydroxy group in the compound (d), the compound (I') can be obtained by reacting the compound (c) with the compound (d) in an inert organic solvent in the presence of an azo compound-based condensing agent and a phosphine reagent. This step is performed in accordance with the case where X in the compound (a) is a hydroxy group in "Synthetic route 1" described above except for using the compound (d) in place of the compound (a) and using the compound (c) in place of the compound (b).

When X in the compound (d) is a chloro group, bromo group, iodo group, methanesulfonyloxy group, benzenesulfonyloxy group, p-toluenesulfonyloxy group, or trifluoromethanesulfonyloxy group, the compound (I') can be obtained by reacting the compound (c) with the compound (d) in an inert organic solvent in the presence of a base. This step is performed in accordance with the case where X in the compound (a) is a chloro group, bromo group, iodo group, methanesulfonyloxy group, benzenesulfonyloxy group, p-toluenesulfonyloxy group, or trifluoromethanesulfonyloxy group in "Synthetic route 1" described above except for using the compound (d) in place of the compound (a) and using the compound (c) in place of the compound (b).

Synthetic Route 3

Synthetic route 3-1 is a step of obtaining the compound (f) by reacting the compound (c) with the compound (e) in an inert organic solvent in the presence of a base. This step is performed in accordance with the case where X in the compound (a) is a chloro group, bromo group, iodo group, methanesulfonyloxy group, benzenesulfonyloxy group, p-toluenesulfonyloxy group, or trifluoromethanesulfonyloxy group in "Synthetic route 1" described above except for using the compound (e) in place of the compound (a) and using the compound (c) in place of the compound (b).

In Synthetic route 3-2, the compound (I') can be obtained by reacting the compound (f) obtained in Synthetic route 3-1 with the compound (g) in an inert solvent under inert gas atmosphere in the presence of a palladium catalyst and either a base or a fluoride.

The inert solvent used is not particularly limited as long as it does not inhibit the reaction and dissolves the raw materials, catalyst, and base (or fluoride) at certain degrees. Examples of the inert solvent include aromatic hydrocarbons, such as benzene and toluene; ethers, such as tetrahydrofuran, 1,2-dimethoxyethane, and 1,4-dioxane; alcohols, such as methanol, ethanol, propanol, and isopropanol; esters, such as methyl acetate and ethyl acetate; amides, such as N,N-dimethylformamide, N,N-dimethylacetamide, and N-methylpyrrolidone; sulfoxides, such as dimethyl sulfoxide; nitriles, such as acetonitrile; water; and arbitrary mixed solvents thereof, and preferably toluene, toluene-ethanol-water mixed solvent, or toluene-water mixed solvent.

Examples of the inert gas used include nitrogen, helium, argon, and the like.

Examples of the palladium catalyst used include metal palladiums, such as palladium-activated carbon and palladium black; organopalladium complexes, such as tetrakis(triphenylphosphine)palladium, bis(triphenylphosphine)palladium chloride, 1,1'-bis(diphenylphosphino)ferrocene palladium chloride, and tris(dibenzylideneacetone)dipalladium; palladium salts, such as palladium chloride and palladium acetate, and preferably tetrakis(triphenylphosphine)palladium or palladium acetate. A molar amount of palladium used as the catalyst is typically 0.0001 to 1-fold, and preferably 0.005 to 0.3-fold based on 1 mole of the compound (f).

When tris(dibenzylideneacetone)dipalladium, palladium chloride, or palladium acetate is used as the catalyst, it is preferably used in the presence of an organophosphine compound. Examples of the organophosphine compound used include tri-n-butylphosphine, tri-tert-butylphosphine, tricyclohexylphosphine, butyldi-1-adamantylphosphine, triphenylphosphine, tri(o-tolyl)phosphine, 2-dicyclohexylphosphino-2',6'-dimethoxybiphenyl, 1,1'-bis(diphenylphosphino)ferrocene, or 1,2,3,4,5-pentaphenyl-1'-(di-tert-butylphosphino)ferrocene, and preferably tricyclohexylphosphine, butyldi-1-adamantylphosphine, triphenylphosphine, or 2-dicyclohexylphosphino-2',6'-dimethoxybiphenyl. A molar amount of the organophosphine compound used is typically 1 to 5-fold, and preferably 1.5 to 2.5-fold based on 1 mole of the palladium.

Examples of the base or fluoride used include alkali metal acetates, such as sodium acetate and potassium acetate; alkali metal carbonates, such as sodium carbonate, potassium carbonate, and cesium carbonate; alkali metal phosphates, such as trisodium phosphate and tripotassium phosphate; alkali metal hydroxides, such as lithium hydroxide, sodium hydroxide, and potassium hydroxide; quaternary ammonium hydroxides, such as tetramethylammonium hydroxide, tetraethylammonium hydroxide, and tetrabutylammonium hydroxide; fluorides, such as cesium fluoride, tetramethylammonium fluoride, tetraethylammonium fluoride, and tetrabutylammonium fluoride, and preferably sodium carbonate or tripotassium phosphate. A molar amount of the base or fluoride used is typically 1 to 10-fold, and preferably 1.5 to 5-fold based on 1 mole of the compound (f).

A molar amount of the compound (g) used is typically 1 to 3-fold, and preferably 1 to 2-fold based on 1 mole of the compound (f).

Although varying depending on types and amounts used of raw materials, solvents, and the like, the reaction temperature is typically 0° C. to 200° C., and preferably 50° C. to 150° C.

Although varying depending on the reaction temperature and the like, the reaction time is typically 10 minutes to 120 hours, and preferably 1 hour to 48 hours.

Synthetic Route 4

The compound (I') can be obtained by reacting the compound (h) with the compound (i) in an inert organic solvent in the presence or absence of (preferably in the presence of) a base.

The inert organic solvent used is not particularly limited as long as it does not inhibit the reaction and dissolves the raw materials at certain degrees. Examples of the inert organic solvent include aromatic hydrocarbons, such as benzene, toluene, and xylene; halogenated aliphatic hydrocarbons, such as methylene chloride, chloroform, and 1,2-dichloroethane; ethers, such as 1,4-dioxane, tetrahydrofuran, diethyl ether, and 1,2-dimethoxyethane; amides, such as N,N-dimethylformamide, N,N-dimethylacetamide, and N-methylpyrrolidone; nitriles, such as acetonitrile and propionitrile, and arbitrary mixed solvents thereof, and preferably methylene chloride, 1,2-dichloroethane, N,N-dimethylformamide, acetonitrile, and a mixed solvent thereof.

Examples of the base used include organic bases, such as triethylamine and diisopropylethylamine; inorganic bases such as sodium bicarbonate, potassium bicarbonate, sodium carbonate, and potassium carbonate, and preferably triethylamine and diisopropylethylamine. A molar amount of the base used is typically 0.9 to 20-fold, and preferably 1 to 10-fold based on 1 mole of the compound (i).

A molar amount of the compound (h) used is typically 0.7 to 5-fold, and preferably 0.8 to 1.5-fold based on 1 mole of the compound (i).

Although varying depending on types and amounts used of raw materials, solvents, and the like, the reaction temperature is typically −20° C. to 100° C., and preferably −5° C. to 50° C.

Although varying depending on the reaction temperature and the like, the reaction time is typically 1 minute to 36 hours, and preferably 1 hour to 18 hours.

Synthetic Route 5

When $R^3$ in the compound (I') is a tert-butoxycarbonyl group, the compound of general formula (I), in which $R^1$ is a carboxy group protected by the ester-type protective group, can be obtained by deprotecting the compound (I') via acid treatment. However, when $R^{1'}$ is a tert-butyl group and $R^3$ is a tert-butoxycarbonyl group in the compound (I'), the compound of general formula (I), in which $R^1$ is a carboxy group, can be obtained by deprotection via acid treatment with hydrochloric acid, trifluoroacetic acid, or the like. Similarly, when $R^3$ in the compound (I') is a hydrogen atom, the compound of general formula (I), in which $R^1$ is a carboxy group, can be obtained by suitably deprotecting the compound (I') via alkaline hydrolysis or the like.

For the substituent $R^2$, a desired substituent may be introduced at the beginning, or a desired substituent may be introduced, after its basic structure is produced by the method described above, using a general synthesizing method including oxidation, reduction, alkylation, esterification, amidation, dehydration reaction, deprotection reaction, hydrolysis, coupling reaction, cyclization reaction, and/or a combination of these reactions.

The starting compound of the compound of the present invention is commercially available or can be produced by a production method that is publicly known by those skilled in the art. The methods for producing the starting compound and an intermediate compound of the compound of the present invention are described in detail in Reference Examples described below.

The target compound formed in each of the reactions can be obtained from the reaction mixture in accordance with conventional methods. For example, after suitably neutralizing the reaction mixture, or removing insolubles by filtration in the case such insolubles are present, an organic solvent such as ethyl acetate that is immiscible with water is added followed by washing with water, separating the organic layer containing the target compound, drying using a drying agent such as anhydrous magnesium sulfate or anhydrous sodium sulfate and then distilling off the solvent to obtain the target compound.

If necessary, the obtained target compound can be separated and/or purified by suitably combining conventional methods, such as recrystallization; reprecipitation; and typical methods that have been commonly used for separation and purification of organic compounds (e.g., adsorption column chromatography methods using silica gel, alumina, or the like as a carrier; ion-exchange chromatography methods; or normal phase/reversed phase column chromatography methods using silica gel or alkylated silica gel (preferably high performance liquid chromatography)).

When the compound of general formula (I) or the pharmacologically acceptable salt thereof in the present invention is used as pharmaceuticals, the compound can be administered alone (as bulk powder), or the compound can be administered orally or parenterally (intravenous administration, intramuscular administration, intraperitoneal administration, dermal administration, transnasal administration, intrabronchial administration, pulmonary administration, intracutaneous administration, subcutaneous administration, or the like) in the dosage form, such as a tablet, capsule, powder, syrup, granule, fine granule, pill, suspension, emulsion, percutaneous absorption agent, suppository, ointment, lotion, aerosol, powder inhalation agent, or injection, that is produced by mixing with suitable pharmacologically acceptable excipients or diluents and the like.

These dosage forms are prepared by commonly known methods using additives, such as excipients, lubricants, binders, disintegrators, emulsions, stabilizers, flavoring agents, diluents, or the like.

Examples of the excipients include organic excipients and inorganic excipients. Examples of the organic excipients include sugar derivatives, such as lactose, sucrose, glucose, mannitol, and sorbitol; starch derivatives, such as cone starch, potato starch, α-starch, and dextrin; cellulose derivatives, such as crystalline cellulose; gum arabic; dextran; pullulan; and the like. Examples of the inorganic excipients include light anhydrous silicic acid; sulfates, such as calcium sulfate; and the like.

Examples of the lubricants include stearic acid; stearic acid metal salts, such as calcium stearate and magnesium stearate; talc; colloidal silica; waxes, such as beeswax and spermaceti wax; boric acid; adipic acid; sulfates, such as sodium sulfate; glycol; fumaric acid; sodium benzoate; D,L-leucine; sodium lauryl sulfate; silicic acids, such as silicic acid anhydride and silicic acid hydrate; starch derivatives described above for the excipients; and the like.

Examples of the binders include hydroxypropyl cellulose, hydroxypropyl methyl cellulose, polyvinylpyrrolidone, macrogol, or compounds described above for the excipients, and the like.

Examples of the disintegrators include cellulose derivatives, such as low substituted hydroxypropyl cellulose, carboxymethyl cellulose, calcium carboxymethyl cellulose, and internally crosslinked calcium carboxymethyl cellulose; crosslinked polyvinylpyrrolidone; chemically modified starch or cellulose derivatives, such as carboxymethyl starch and sodium carboxymethyl starch; and the like.

Examples of the emulsifiers include colloidal clays, such as bentonite and Veegum; anionic surfactants, such as sodium lauryl sulfate; cationic surfactants, such as benzalkonium chloride; nonionic surfactants, such as polyoxyethylene alkyl ether, polyoxyethylene sorbitan fatty acid ester, and sucrose fatty acid ester; and the like.

Examples of the stabilizers include para-hydroxybenzoates, such as methylparaben and propylparaben; alcohols, such as chlorobutanol, benzyl alcohol, and phenylethyl alcohol; benzalkonium chloride; phenols, such as phenol and cresol; thimerosal; acetic anhydride; sorbic acid; and the like.

Examples of the corrigents include sweeteners, such as saccharin sodium and aspartame; acidulants, such as citric acid, malic acid, and tartaric acid; flavorings, such as menthol, lemon extract, and orange extract; and the like.

Examples of diluents include compounds commonly used as diluents, such as lactose, mannitol, glucose, sucrose, calcium sulfate, hydroxypropyl cellulose, microcrystalline cellulose, water, ethanol, polyethylene glycol, propylene glycol, glycerol, starch, polyvinylpyrrolidone, mixtures thereof, and the like.

In addition, suitable additives can be used depending on the dosage form. For example, when the compound of general formula (I) or the pharmacologically acceptable salt of the present invention is formed into an aerosol for transnasal administration or intrabronchial administration, chlorofluorocarbons (CFCs), such as dichlorodifluoromethane, trichlorofluoromethane, and dichlorotetrafluoroethane; carbon dioxide, and the like can be used as a propellant.

Although the dosage of the compound of general formula (I) or the pharmacologically acceptable salt of the present invention can be varied depending on the conditions such as symptoms, age, and weight of the patient, the dosage for an adult in the case of oral administration has the lower limit of 0.001 mg/kg (preferably 0.01 mg/kg) and the upper limit of 20 mg/kg (preferably 10 mg/kg), while the dosage for an adult in the case of parenteral administration has the lower limit of 0.0001 mg/kg (preferably 0.0005 mg/kg) and the upper limit of 10 mg/kg (preferably 5 mg/kg), which can be administered corresponding to symptoms for 1 to 6 times per day.

EXAMPLES

Although the following provides a more detailed explanation of the present invention through Examples, Reference Examples, Comparative Examples, and Test Examples; however, the present invention is not limited to these.

Example 1

Ethyl (6-{[3'-(1-propenyl)biphenyl-4-ylmethyl]
(pyridin-2-ylsulfonyl)-aminomethyl}pyridin-2-ylamino)acetate To a solution of 205 mg (0.913 mmol) of 3'-(1-propenyl)biphenyl-4-ylmethanol obtained in Reference Example 3-(b)

in 9.4 mL of tetrahydrofuran, 320 mg (0.913 mmol) of ethyl {6-[(pyridin-2-ylsulfonyl)aminomethyl]pyridin-2-ylamino}acetate obtained in the same manner as in Reference Example 1-(g), 570 μL (2.31 mmol) of tri-n-butylphosphine, and 236 mg (1.37 mmol) of N,N,N',N'-tetramethylazodicarboxamide were added and stirred for 5 hours at room temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=2:3 (V/V)), and fractions containing the target product were concentrated under reduced pressure to afford 510 mg of the title compound as a slightly yellow oil. (Quantitative)

Mass spectrum (FAB, m/z): 557 ($M^+$+1)
$^1$H-NMR spectrum (CDCl$_3$, δ ppm): 8.62 (ddd, J=4.7, 1.8, 1.0 Hz, 1H), 7.83 (ddd, J=7.8, 1.0, 1.0 Hz, 1H), 7.75 (ddd, J=7.8, 7.6, 1.8 Hz, 1H), 7.52-7.43 (m, 3H), 7.41-7.30 (m, 6H), 7.27-7.20 (m, 1H), 6.51 (d, J=7.3 Hz, 1H), 6.50-6.42 (m, 1H), 6.38-6.26 (m, 1H), 6.23 (d, J=8.3 Hz, 1H), 4.80 (s, 2H), 4.70 (t, J=5.4 Hz, 0.911), 4.42 (s, 2H), 4.22 (q, J=7.1 Hz, 2H), 3.96 (d, J=5.4 Hz, 2H), 1.91 (dd, J=6.3, 1.5 Hz, 3H), 1.28 (t, J=7.1 Hz, 3H)

Example 2

(6-{[3'-(1-Propenyl)biphenyl-4-ylmethyl](pyridin-2-ylsulfonyl)aminomethyl}-pyridin-2-ylamino)acetic acid To a solution of 220 mg (0.395 mmol) of ethyl (6-{[3'-(1-propenyl)biphenyl-4-ylmethyl](pyridin-2-ylsulfonyl)aminomethyl}pyridin-2-ylamino)acetate obtained in Example 1 in 2.0 mL of ethanol, 1.98 mL (1.98 mmol) of 1 mol/L aqueous sodium hydroxide solution was added and stirred for 2.5 hours at room temperature. After the completion of the reaction, water was added to the reaction solution, and pH of the solution was adjusted to 4.5 with 1 mol/L hydrochloric acid. The precipitated solid was collected by filtration and then dried under reduced pressure to afford 146 mg of the title compound as a white solid. (Yield: 70%)

Mass spectrum (FAB, m/z): 529 ($M^+$+1)
$^1$H-NMR spectrum (DMSO-d$_6$, δ ppm): 8.64 (ddd, J=4.8, 1.7, 0.9 Hz, $^1$H), 7.95 (ddd, J=7.7, 7.7, 1.7 Hz, 1H), 7.80 (ddd, J=7.7, 1.0, 0.9 Hz, 1H), 7.61-7.56 (m, 4H), 7.48-7.44 (m, 1H), 7.39-7.37 (m, 2H), 7.35-7.32 (m, 2H), 7.19 (dd, J=8.3, 7.2 Hz, 1H), 6.61 (brs, 0.8H), 6.52-6.47 (m, 1H), 6.44-6.37 (m, 1H), 6.33 (d, J=8.3 Hz, 1H), 6.28 (d, J=7.2 Hz, 1H), 4.74 (s, 2H), 4.24 (s, 2H), 3.76 (d, J=4.0 Hz, 2H), 1.87 (dd, J=6.2, 1.5 Hz, 3H)

Example 3

Ethyl (6-{[3'-(1-propynyl)biphenyl-4-ylmethyl](pyridin-2-ylsulfonyl)-aminomethyl}pyridin-2-ylamino)acetate To a solution of 200 mg (0.900 mmol) of 3'-(1-propynyl)biphenyl-4-ylmethanol obtained in Reference Example 4-(b) in 4.0 mL of tetrahydrofuran, 315 mg (0.900 mmol) of ethyl {6-[(pyridin-2-ylsulfonyl)-aminomethyl]pyridin-2-ylamino}acetate obtained in the same manner as in Reference Example 1-(g), 450 μL (1.82 mmol) of tri-n-butylphosphine, and 310 mg (1.80 mmol) of N,N,N',N'-tetramethylazodicarboxamide were added and stirred for 3 hours at room temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=3:2→2:3 (V/V)), and fractions containing the target product were concentrated under reduced pressure to afford 483 mg of the title compound as a white foam. (Yield: 97%)

Mass spectrum (FAB, m/z): 555 ($M^+$+1)
$^1$H-NMR spectrum (CDCl$_3$, δ ppm): 8.62 (ddd, J=4.6, 1.7, 1.0 Hz, 1H), 7.83 (ddd, J=7.7, 1.3, 1.0 Hz, 1H), 7.75 (ddd, J=7.7, 7.7, 1.7 Hz, 1H), 7.59-7.58 (m, 1H), 7.47-7.43 (m, 3H), 7.41-7.31 (m, 5H), 7.23 (dd, J=8.2, 7.1 Hz, 1H), 6.51 (d, J=7.1 Hz, 1H), 6.23 (d, J=8.2 Hz, 1H), 4.79 (s, 2H), 4.70 (t, J=5.4 Hz, 1H), 4.42 (s, 2H), 4.22 (q, J=7.1 Hz, 2H), 3.96 (d, J=5.4 Hz, 2H), 2.08 (s, 3H), 1.28 (t, J=7.1 Hz, 3H)

Example 4

(6-{[3'-(1-Propynyl)biphenyl-4-ylmethyl](pyridin-2-ylsulfonyl)aminomethyl}-pyridin-2-ylamino)acetic acid To a solution of 476 mg (0.858 mmol) of ethyl (6-{[3'-(1-propynyl)biphenyl-4-ylmethyl](pyridin-2-ylsulfonyl)aminomethyl}pyridin-2-ylamino)acetate obtained in Example 3 in 3.0 mL of ethanol, 3.43 mL (3.43 mmol) of 1 mol/L aqueous sodium hydroxide solution was added and stirred for 5 hours at room 0.15 temperature. After the completion of the reaction, water was added to the reaction solution. Then, pH of the solution was adjusted to 4.5 with 1 mol/L hydrochloric acid, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; methylene chloride:methanol=15:1→10:1 (V/V)), and fractions containing the target product were concentrated under reduced pressure to afford 444 mg of the title compound as a white foam. (Yield: 98%)

Mass spectrum (FAB, m/z): 527 ($M^+$+1)
$^1$H-NMR spectrum (DMSO-d$_6$, δ ppm): 12.42 (brs, 0.6H), 8.64 (ddd, J=4.7, 1.8, 1.0 Hz, 1H), 7.95 (ddd, J=7.7, 7.7, 1.8 Hz, 1H), 7.80 (ddd, J=7.7, 1.0, 1.0 Hz, 1H), 7.63-7.56 (m, 5H), 7.43 (dd, J=7.9, 7.9 Hz, 1H), 7.38-7.36 (m, 1H), 7.35-7.32 (m, 2H), 7.19 (dd, J 8.4, 7.0 Hz, 1H), 6.75 (t, =5.9 Hz, 1H), 6.34 (d, J=8.4 Hz, 1H), 6.28 (d, J=7.0 Hz, 1H), 4.74 (s, 2H), 4.24 (s, 2H), 3.82 (d, J=5.9 Hz, 2H), 2.07 (s, 3H)

Example 5

Ethyl (6-{[3'-(1-propynyl)biphenyl-4-ylmethyl](pyridin-3-ylsulfonyl)-aminomethyl}pyridin-2-ylamino)acetate To a solution of 178 mg (0.800 mmol) of 3'-(1-propynyl)biphenyl-4-ylmethanol obtained in the same manner as in Reference Example 4-(b) in 4.0 mL of tetrahydrofuran, 280 mg (0.800 mmol) of ethyl {6-[(pyridin-3-ylsulfonyl)aminomethyl]pyridin-2-ylamino}acetate obtained in the same manner as in Reference Example 2-(b), 395 μL (1.60 mmol) of tri-n-butylphosphine, and 276 mg (1.60 mmol) of N,N,N',N'-tetramethylazodicarboxamide were added and stirred for 3 hours at room temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=3:7→0:1 (V/V)), and fractions containing the target product were concentrated under reduced pressure to afford 400 mg of the title compound as a slightly yellow oil. (Yield: 90%)

Mass spectrum (ESI$^+$, m/z): 555 (M$^+$+1)

$^1$H-NMR spectrum (CDCl$_3$, δ ppm): 8.97 (dd, J=2.3, 0.7 Hz, 1H), 8.69 (dd, J=4.9, 1.7 Hz, 1H), 7.92 (ddd, J=8.0, 2.3, 1.7 Hz, 1H), 7.61-7.60 (m, 1H), 7.52-7.49 (m, 2H), 7.48-7.46 (m, 1H), 7.38-7.35 (m, 4H), 7.32-7.27 (m, 2H), 6.46 (d, J=7.0 Hz, 1H), 6.28 (d, J=8.2 Hz, 1H), 4.74 (t, J=5.4 Hz, 1H), 4.66 (s, 2H), 4.34 (s, 2H), 4.22 (q, J 7.2 Hz, 2H), 3.87 (d, J=5.4 Hz, 2H), 2.08 (s, 3H), 1.29 (t, J=7.2 Hz, 3H)

Example 6

(6-{[3'-(1-Propynyl)biphenyl-4-ylmethyl](pyridin-3-ylsulfonyl)aminomethyl}-pyridin-2-ylamino)acetic acid To a solution of 395 mg (0.712 mmol) of ethyl (6-{[3'-(1-propynyl)-biphenyl-4-ylmethyl](pyridin-3-ylsulfonyl) aminomethyl}pyridin-2-ylamino)acetate obtained in Example 5 in 3.0 mL of ethanol, 3.0 mL (3.0 mmol) of 1 mol/L aqueous sodium hydroxide solution was added and stirred for 16 hours at room temperature. After the completion of the reaction, water was added to the reaction solution. Then, pH of the solution was adjusted to 4.5 with 1 mol/L hydrochloric acid, followed by extraction with ethyl acetate. The organic layer was washed with saturated aqueous sodium chloride solution, dried over anhydrous sodium sulfate, and then concentrated under reduced pressure. To the residue were added 10 mL of tert-butyl methyl ether and 0.5 mL of methanol, followed by sonication. The precipitated solid was collected by filtration and dried under reduced pressure to afford 340 mg of the title compound as a white solid. (Yield: 91%)

Mass spectrum (ESI$^+$, m/z): 527 (M$^+$+1)

$^1$H-NMR spectrum (DMSO-d$_6$, δ ppm): 12.42 (brs, 0.6H), 8.83 (dd, J=2.4, 0.6 Hz, 1H), 8.72 (dd, J=4.8, 1.6 Hz, 1H), 8.02 (ddd, J=8.1, 2.4, 1.6 Hz, 1H), 7.65-7.61 (m, 4H), 7.47 (ddd, J=8.1, 4.8, 0.6 Hz, 1H), 7.44 (dd, J=7.9, 7.9 Hz, 1H), 7.39-7.36 (m, 3H), 7.24 (dd, J=8.3, 7.1 Hz, 1H), 6.78 (t, J=5.9 Hz, 1H), 6.37 (d, J=8.3 Hz, 1H), 6.33 (d, J=7.1 Hz, 1H), 4.71 (s, 2H), 4.21 (s, 2H), 3.71 (d, J=5.9 Hz, 2H), 2.07 (s, 3H)

Example 7

{6-[(3'-Ethoxybiphenyl-4-ylmethyl)(pyridin-2-ylsulfonyl)aminomethyl]-pyridin-2-ylamino}acetic acid 7-(a): tert-Butyl (tert-butoxycarbonyl {6-[(3'-ethoxybiphenyl-4-ylmethyl)-(pyridin-2-ylsulfonyl) aminomethyl]pyridin-2-yl}amino)acetate To a solution of 183 mg (0.800 mmol) of 3'-ethoxybiphenyl-4-ylmethanol obtained in Reference Example 5 in 4.0 mL of tetrahydrofuran, 422 mg (0.880 mmol) of tert-butyl (tert-butoxycarbonyl{6-[(pyridin-2-ylsulfonyl)aminomethyl]-pyridin-2-yl}-amino)acetate obtained in the same manner as in Reference Example 1-(f), 395 μL (1.60 mmol) of tri-n-butylphosphine, and 276 mg (1.60 mmol) of N,N,N',N'-tetramethylazodicarboxamide were added and stirred for 3 hours at room temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; toluene: ethyl acetate=8:1→6:1 (V/V)), and fractions containing the target product were concentrated under reduced pressure to afford 537 mg of the title compound as a white foam. (Yield: 98%)

Mass spectrum (FAB, m/z): 689 (M$^+$+1)

$^1$H-NMR spectrum (CDCl$_3$, δ ppm): 8.60 (ddd, J=4.6, 1.8, 1.0 Hz, 1H), 7.82 (ddd, J=7.7, 1.0, 1.0 Hz, 1H), 7.77 (ddd, J=7.7, 7.6, 1.8 Hz, 1H), 7.65 (d, J=8.3 Hz, 1H), 7.48-7.26 (m, 7H), 7.11 (ddd, J=7.9, 1.7, 0.9 Hz, 1H), 7.07 (dd, J=2.3, 1.7 Hz, 1H), 6.91 (d, J=7.3 Hz, 1H), 6.88 (ddd, J=7.9, 2.3, 0.9 Hz, 1H), 4.74 (s, 2H), 4.51 (s, 2H), 4.46 (s, 2H), 4.10 (q, J=6.9 Hz, 2H), 1.52 (s, 9H), 1.45 (t, J=6.9 Hz, 3H), 1.42 (s, 9H)

7-(b): {6-[(3'-Ethoxybiphenyl-4-ylmethyl)(pyridin-2-ylsulfonyl)-aminomethyl]pyridin-2-ylamino}acetic acid To a solution of 525 mg (0.762 mmol) of tert-butyl (tert-butoxycarbonyl {6-[(3'-ethoxybiphenyl-4-ylmethyl) (pyridin-2-ylsulfonyl)-aminomethyl]pyridin-2-yl}amino) acetate obtained in Example 7-(a) in 4.0 mL of 1,4-dioxane, 3.2 mL (19.2 mmol) of 6 mol/L hydrochloric acid and 0.8 mL of water were added, and stirred at 70° C. for 2 hours. After the completion of the reaction, the reaction solution was concentrated under reduced pressure, followed by addition of water. Then, pH of the solution was adjusted to 4.4 with 1 mol/L aqueous sodium hydroxide solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; methylene chloride:methanol=15:1→10:1 (V/V)), and fractions containing the target product ware concentrated under reduced pressure to afford 369 mg of the title compound as a white foam. (Yield: 91%)

Mass spectrum (FAB, m/z): 533 (M$^+$+1)

$^1$H-NMR spectrum (DMSO-d$_6$, δ ppm): 12.41 (brs, 0.4H), 8.64 (ddd, J=4.6, 1.8, 0.9 Hz, 1H), 7.95 (ddd, J=7.8, 7.8, 1.8 Hz, 1H), 7.80 (ddd, J=7.8, 1.0, 0.9 Hz, 1H), 7.59-7.56 (m, 3H), 7.36 (dd, J=8.1, 8.1 Hz, 1H), 7.33-7.31 (m, 2H), 7.20 (dd, J=8.2, 7.1 Hz, 1H), 7.18 (ddd, J=8.1, 1.8, 0.8 Hz, 1H), 7.14 (dd, J=2.3, 1.8 Hz, 1H), 6.92 (ddd, J=8.1, 2.3, 0.8 Hz, 1H), 6.75 (t, J=5.9 Hz, 1H), 6.34 (d, J=8.2 Hz, 1H), 6.28 (d, J=7.1 Hz, 1H), 4.74 (s, 2H), 4.24 (s, 2H), 4.10 (q, J=7.0 Hz, 2H), 3.82 (d, J=5.9 Hz, 2H), 1.35 (t, J=7.0 Hz, 3H)

Example 8

Hexyl {6-[(3'-ethoxybiphenyl-4-ylmethyl)(pyridin-2-ylsulfonyl)aminomethyl]pyridin-2-ylamino}acetate To a solution of 171 mg (0.750 mmol) of 3'-ethoxybiphenyl-4-ylmethanol obtained in Reference Example 5 in 4.0 mL of tetrahydrofuran, 305 mg (0.750 mmol) of hexyl {6-[(pyridin-2-ylsulfonyl)aminomethyl]pyridin-2-ylamino}acetate obtained in Reference Example 6, 280 pit (1.14 mmol) of tri-n-butylphosphine, and 196 mg (1.14 mmol) of N,N,N',N'-tetramethylazodicarboxamide were added and stirred for 16 hours at room temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=3:2→2:3 (V/V)), and fractions containing the target product were concentrated under reduced pressure to afford 429 mg of the title compound as a colorless oil. (Yield: 93%)

Mass spectrum (FAB, m/z): 617 (M$^+$+1)

$^1$H-NMR spectrum (CDCl$_3$, δ ppm): 8.61 (ddd, J=4.7, 1.7, 1.0 Hz, 1H), 7.82 (ddd, J=7.7, 1.1, 1.0 Hz, 1H), 7.75 (ddd, J=7.7, 7.7, 1.7 Hz, 1H), 7.47-7.45 (m, 2H), 7.38 (ddd, J=7.7, 4.7, 1.1 Hz, 1H), 7.35-7.31 (m, 3H), 7.23 (dd, J=8.4, 7.3 Hz, 1H), 7.12 (ddd, J=8.1, 1.8, 1.0 Hz, 1H), 7.08 (dd, J=2.4, 1.8 Hz, 1H), 6.88 (ddd, J=8.1, 2.4, 1.0 Hz, 1H), 6.51 (d, J=7.3 Hz, 1H), 6.23 (d, J=8.4 Hz, 1H), 4.79 (s, 2H), 4.70 (t, J=5.3 Hz, 1H), 4.42 (s, 2H), 4.15 (t, J=6.8 Hz, 2H), 4.10 (q, J=7.0 Hz, 2H), 3.96 (d, J=5.3 Hz, 2H), 1.66-1.60 (m, 2H), 1.45 (t, J=7.0 Hz, 3H), 1.34-1.25 (m, 6H), 0.87 (t, J=7.0 Hz, 3H)

Example 9

{6-[(3'-Ethoxybiphenyl-4-ylmethyl)(pyridin-3-ylsulfonyl)aminomethyl]-pyridin-2-ylamino}acetic acid 9-(a): tert-Butyl (tert-butoxycarbonyl{6-{(3'-ethoxybiphenyl-4-ylmethyl)(pyridin-3-ylsulfonyl)aminomethyl}pyridin-2-yl}amino)acetate To a solution of 183 mg (0.800 mmol) of 3'-ethoxybiphenyl-4-ylmethanol obtained in Reference Example 5 in 4.0 mL of tetrahydrofuran, 422 mg (0.880 mmol) of tert-butyl (tert-butoxycarbonyl{6-[(pyridin-3-ylsulfonyl)aminomethyl]-pyridin-2-yl}amino)acetate obtained in the same manner as in Reference Example 2-(a), 395 μL (1.60 mmol) of tri-n-butylphosphine, and 276 mg (1.60 mmol) of N,N,N',N'-tetramethylazodicarboxamide were added and stirred for 3 hours at room temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=7:3→1:1 (V/V)), and fractions containing the target product were concentrated under reduced pressure to afford 550 mg of the title compound as a white foam. (Quantitative)

Mass spectrum (FAB, m/z): 689 (M$^+$+1)

$^1$H-NMR spectrum (CDCl$_3$, δ ppm): 8.96 (dd, J=2.4, 0.7 Hz, 1H), 8.71 (dd, J=4.8, 1.6 Hz, 1H), 7.87 (ddd, J=7.9, 2.4, 1.6 Hz, 1H), 7.71 (d, J=8.5 Hz, 1H), 7.54-7.47 (m, 3H), 7.36-7.26 (m, 4H), 7.13 (ddd, J=7.9, 1.9, 1.0 Hz, 1H), 7.08 (dd, J=2.3, 1.9 Hz, 1H), 6.89 (ddd, J=8.3, 2.3, 1.0 Hz, 1H), 6.87 (d, J=7.3 Hz, 1H), 4.62 (s, 2H), 4.42 (s, 2H), 4.37 (s, 2H), 4.10 (q, J=7.0 Hz, 2H), 1.52 (s, 9H), 1.45 (t, J=7.0 Hz, 3H), 1.42 (s, 9H)

9-(b): {6-[(3'-Ethoxybiphenyl-4-ylmethyl)(pyridin-3-ylsulfonyl)aminomethyl]-pyridin-2-ylamino}acetic acid To a solution of 540 mg (0.784 mmol) of tert-butyl (tert-butoxycarbonyl-{6-[(3'-ethoxybiphenyl-4-ylmethyl)(pyridin-3-ylsulfonyl)aminomethyl]pyridin-2-yl}-amino)acetate obtained in Example 9-(a) in 4.0 mL of 1,4-dioxane, 3.3 mL (20 mmol) of 6 mol/L hydrochloric acid and 1.0 mL of water were added, and stirred at 70° C. for 2 hours. After the completion of the reaction, the reaction solution was concentrated under reduced pressure, followed by addition of water. Then pH of the solution was adjusted to 4.4 with 1 mol/L aqueous sodium hydroxide solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; methylene chloride:methanol=15:1→10:1 (V/V)), and fractions containing the target product were concentrated under reduced pressure. To the concentrated product were added 2 mL of ethyl acetate and 8 mL of n-hexane, and the precipitated solid was collected by filtration, followed by drying under reduced pressure to afford 388 mg of the title compound as a white solid. (Yield: 93%)

Mass spectrum (FAB, m/z): 533 (M$^+$+1)

$^1$H-NMR spectrum (DMSO-d$_6$, δ ppm): 12.43 (brs, 0.4H), 8.83 (dd, J=2.4, 0.7 Hz, 1H), 8.72 (dd, J=4.8, 1.7 Hz, 1H), 8.02 (ddd, J=8.0, 2.4, 1.7 Hz, 1H), 7.64-7.61 (m, 2H), 7.47 (ddd, J=8.0, 4.8, 0.7 Hz, 1H), 7.38-7.34 (m, 3H), 7.24 (dd, J=8.3, 7.2 Hz, 1H), 7.20 (ddd, J=7.8, 1.7, 0.9 Hz, 1H), 7.16 (dd, J=2.3, 1.7 Hz, 1H), 6.92 (ddd, J=8.2, 2.3, 0.9 Hz, 1H), 6.78 (t, J=5.9 Hz, 1H), 6.37 (d, J=8.3 Hz, 1H), 6.33 (d, J=7.2 Hz, 1H), 4.70 (s, 2H), 4.21 (s, 2H), 4.10 (q, J=7.0 Hz, 2H), 3.71 (d, J=5.9 Hz, 2H), 1.36 (t, J=7.0 Hz, 3H)

Example 10

{6-[(Benzenesulfonyl)(3'-ethoxybiphenyl-4-ylmethyl)aminomethyl]pyridin-2-ylamino}acetic acid 10-(a): tert-Butyl ({6-[(benzenesulfonyl)(3'-ethoxybiphenyl-4-ylmethyl)-aminomethyl]pyridin-2-yl}tert-butoxycarbonylamino)acetate To a solution of 350 mg (0.639 mmol) of tert-butyl (tert-butoxycarbonyl-{6-[(3'-ethoxybiphenyl-4-ylmethyl)aminomethyl]pyridin-2-yl}amino)acetate obtained in Reference Example 7-(b) in 1.8 mL of methylene chloride, 178 μL (1.28 mmol) of triethylamine and 98 μL (0.77 mmol) of benzenesulfonyl chloride were added under ice cooling and then stirred for 1 hour at room temperature. After the completion of the reaction, the reaction solution was subjected to silica gel column chromatography (elution solvent; n-hexane:ethyl acetate=4:1→7:3 (V/V)), and fractions containing the target product were concentrated under reduced pressure to afford 392 mg of the title compound as a white foam. (Yield: 89%)

Mass spectrum (CI, m/z): 688 (M$^+$+1)

$^1$H-NMR spectrum (CDCl$_3$, δ ppm): 7.77-7.73 (m, 2H), 7.67 (d, J=8.3 Hz, 1H), 7.56-7.41 (m, 6H), 7.33 (dd, J=7.9, 7.7 Hz, 1H), 7.24-7.19 (m, 2H), 7.11 (ddd, J=7.7, 1.7, 0.9 Hz, 1H), 7.07 (dd, J=2.3, 1.7 Hz, 1H), 6.88 (ddd, J=7.9, 2.3, 0.9 Hz, 1H), 6.86 (d, J=7.5 Hz, 1H), 4.54 (s, 2H), 4.39 (s, 2H), 4.35 (s, 2H), 4.09 (q, J=7.1 Hz, 2H), 1.51 (s, 9H), 1.44 (t, J=7.1 Hz, 3H), 1.41 (s, 9H)

10-(b): {6-[(Benzenesulfonyl)(3'-ethoxybiphenyl-4-ylmethyl)aminomethyl]-pyridin-2-ylamino}acetic acid To a solution of 389 mg (0.566 mmol) of tert-butyl ({6-[(benzenesulfonyl)(3'-ethoxybiphenyl-4-ylmethyl)aminomethyl]pyridin-2-yl}-tert-butoxycarbonylamino)acetate obtained in Example 10-(a) in 5.8 mL of methylene chloride, 5.8 mL (76 mmol) of trifluoroacetic acid was added at room temperature and allowed to stand undisturbed for 3.5 hours. After the completion of the reaction, the reaction solution was concentrated under reduced pressure, followed by addition of water. Then pH of the solution was adjusted to 4.4 with saturated aqueous sodium bicarbonate solution and 1 mol/L hydrochloric acid, followed by extraction with ethyl acetate. The organic layer was washed with saturated aqueous sodium chloride solution, dried over anhydrous sodium sulfate, and then concentrated under reduced pressure. To the concentrated product was added 3.9 mL of diisopropyl ether, and the precipitated solid was collected by filtration, followed by drying under reduced pressure to afford 293 mg of the title compound as a white solid. (Yield: 97%)

Mass spectrum (FAB, m/z): 532 ($M^+$+1)

$^1$H-NMR spectrum (DMSO-$d_6$, δ ppm): 12.41 (brs, 0.8H), 7.74-7.72 (m, 2H), 7.61-7.59 (m, 3H), 7.52-7.48 (m, 2H), 7.35 (dd, J=7.8, 7.8 Hz, 1H), 7.31-7.29 (m, 2H), 7.23 (dd, J=8.4, 7.2 Hz, 1H), 7.19 (ddd, J=7.8, 1.7, 0.9 Hz, 1H), 7.14 (dd, J=2.3, 1.7 Hz, 1H), 6.91 (ddd, J=7.8, 2.3, 0.9 Hz, 1H), 6.76 (t, J=5.9 Hz, 1H), 6.37 (d, J=8.4 Hz, 1H), 6.29 (d, J=7.2 Hz, 1H), 4.59 (s, 2H), 4.16 (s, 2H), 4.10 (q, J=7.0 Hz, 2H), 3.77 (d, J=5.9 Hz, 2H), 1.35 (t, J=7.0 Hz, 3H)

Example 11

{6-[(3'-Ethoxybiphenyl-4-ylmethyl)(thiophen-2-ylsulfonyl)aminomethyl]-pyridin-2-ylamino}acetic acid

11-(a): tert-Butyl (tert-butoxycarbonyl{6-[(3'-ethoxybiphenyl-4-ylmethyl)-(thiophen-2-ylsulfonyl)aminomethyl]pyridin-2-yl}amino)acetate To a solution of 350 mg (0.639 mmol) of tert-butyl (tert-butoxycarbonyl-{6-[(3'-ethoxybiphenyl-4-ylmethyl)aminomethyl]pyridin-2-yl}amino)acetate obtained in Reference Example 7-(b) in 1.8 mL of methylene chloride, 178 μL (1.28 mmol) of triethylamine and a solution of 141 mg (0.772 mmol) of 2-thiophenesulfonyl chloride in 0.3 mL of methylene chloride were added under ice cooling and then stirred for 1.5 hours at room temperature. After the completion of the reaction, the reaction solution was subjected to silica gel column chromatography (elution solvent; n-hexane:ethyl acetate=9:1→3:2 (V/V)), and fractions containing the target product were concentrated under reduced pressure to afford 376 mg of the title compound as a white foam. (Yield: 85%)

Mass spectrum (CI, m/z): 694 ($M^+$+1)

$^1$H-NMR spectrum (CDCl$_3$, δ ppm): 7.70 (d, J=8.5 Hz, 1H), 7.54-7.42 (m, 5H), 7.33 (dd, J=8.0, 7.8 Hz, 1H), 7.27-7.23 (m, 2H), 7.12 (ddd, J=7.7, 1.7, 0.9 Hz, 1H), 7.08 (dd, J=2.4, 1.7 Hz, 1H), 7.02 (dd, J=5.1, 3.7 Hz, 1H), 6.92 (d, J=7.6 Hz, 1H), 6.88 (ddd, J=8.0, 2.4, 0.9 Hz, 1H), 4.56 (s, 2H), 4.43 (s, 2H), 4.39 (s, 2H), 4.10 (q, J=7.0 Hz, 2H), 1.52 (s, 9H), 1.44 (t, J=7.0 Hz, 3H), 1.42 (s, 9H)

11-(b): {6-[(3'-Ethoxybiphenyl-4-ylmethyl)(thiophen-2-ylsulfonyl)aminomethyl]pyridin-2-ylamino}acetic acid To a solution of 374 mg (0.538 mmol) of tert-butyl (tert-butoxycarbonyl{6-[(3'-ethoxybiphenyl-4-ylmethyl)(thiophen-2-ylsulfonyl)-aminomethyl]pyridin-2-yl}amino)acetate obtained in Example 11-(a) in 5.6 mL of methylene chloride, 5.6 mL (73 mmol) of trifluoroacetic acid was added at room temperature and allowed to stand undisturbed for 3.5 hours. After the completion of the reaction, the reaction solution was concentrated under reduced pressure, followed by addition of water. Then pH of the solution was adjusted to 4.4 using saturated aqueous sodium bicarbonate solution and 1 mol/L hydrochloric acid, followed by extraction with ethyl acetate. The organic layer was washed with saturated aqueous sodium chloride solution, dried over anhydrous sodium sulfate, and then concentrated under reduced pressure. To the concentrated product was added 3.7 mL of tert-butyl methyl ether, and the precipitated solid was collected by filtration, followed by drying under reduced pressure to afford 272 mg of the title compound as a white solid. (Yield: 94%)

Mass spectrum (FAB, m/z): 538 ($M^+$+1)

$^1$H-NMR spectrum (DMSO-$d_6$, δ ppm): 12.42 (brs, 0.7H), 7.91 (dd, J=5.1, 1.4 Hz, 1H), 7.61-7.58 (m, 2H), 7.54 (dd, J=3.7, 1.4 Hz, 1H), 7.35 (dd, J=7.9, 7.8 Hz, 1H), 7.34-7.31 (m, 2H), 7.27 (dd, J=8.4, 7.2 Hz, 1H), 7.19 (ddd, J=7.8, 1.7, 0.9 Hz, 1H), 7.15 (dd, J=2.3, 1.7 Hz, 1H), 7.13 (dd, J=5.1, 3.7 Hz, 1H), 6.91 (ddd, J=7.9, 2.3, 0.9 Hz, 1H), 6.79 (t, J=5.8 Hz, 1H), 6.41 (d, J=8.4 Hz, 1H), 6.35 (d, J=7.2 Hz, 1H), 4.58 (s, 2H), 4.17 (s, 2H), 4.10 (q, J=7.0 Hz, 2H), 3.83 (d, J=5.8 Hz, 2H), 1.35 (t, J=7.0 Hz, 3H)

Example 12

(6-{[4-(6-Ethoxypyridin-2-yl)benzyl](pyridin-2-ylsulfonyl)aminomethyl}-pyridin-2-ylamino)acetic acid

12-(a): tert-Butyl [tert-butoxycarbonyl(6-{[4-(6-ethoxypyridin-2-yl)benzyl]-(pyridin-2-ylsulfonyl)aminomethyl}pyridin-2-yl)amino]acetate To a solution of 267 mg (1.16 mmol) of 4-(6-ethoxypyridin-2-yl)phenylmethanol obtained in Reference Example 8 in 11 mL of tetrahydrofuran, 560 mg (1.17 mmol) of tert-butyl (tert-butoxycarbonyl-{6-[(pyridin-2-ylsulfonyl)aminomethyl]pyridin-2-yl}amino)acetate obtained in the same manner as in Reference Example 1-(f), 724 μL (2.90 mmol) of tri-n-butylphosphine, and 300 mg (1.74 mmol) of N,N,N',N'-tetramethylazodicarboxamide were added and stirred for 1.5 hours at room temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=3:1 (V/V)), and fractions containing the target product were concentrated under reduced pressure to afford 606 mg of the title compound as a white foam. (Yield: 76%)

Mass spectrum (CI, m/z): 690 ($M^+$+1)

¹H-NMR spectrum (CDCl₃, δ ppm): 8.60 (ddd, J=4.7, 1.8, 1.1 Hz, 1H), 7.92-7.88 (m, 2H), 7.82 (ddd, J=7.7, 1.3, 1.1 Hz, 1H), 7.76 (ddd; J=7.7, 7.5, 1.8 Hz, 1H), 7.65 (d, J=8.5 Hz, 1H), 7.6.1 (dd, J=8.2, 7.5 Hz, 1H), 7.45 (dd, J=8.3, 7.5 Hz, 1H), 7.38 (ddd, J=7.5, 4.7, 1.3 Hz, 1H), 7.34-7.30 (m, 2H), 7.28 (dd, J=7.5, 0.6 Hz, 1H), 6.90 (d, J=7.5 Hz, 1H), 6.66 (dd, J=8.3, 0.6 Hz, 1H), 4.76 (s, 2H), 4.49 (s, 2H), 4.48 (q, J=7.1 Hz, 2H), 4.46 (s, 2H), 1.52 (s, 9H), 1.44 (t, J=7.1 Hz, 3H), 1.42 (s, 9H)

12-(b): (6-{[4-(6-Ethoxypyridin-2-yl)benzyl](pyridin-2-ylsulfonyl)aminomethyl}pyridin-2-ylamino) acetic acid To a solution of 590 mg (0.855 mmol) of tert-butyl [tert-butoxycarbonyl(6-{[4-(6-ethoxypyridin-2-yl)benzyl](pyridin-2-ylsulfonyl)-aminomethyl}pyridin-2-yl)amino] acetate obtained in Example 12-(a) in 8.6 mL of methylene chloride, 8.6 mL (112 mmol) of trifluoroacetic acid was added at room temperature and stirred for 6 hours at room temperature. After the completion of the reaction, the reaction solution was concentrated under reduced pressure, followed by addition of water. Then pH of the solution was adjusted to 4.5 with 2 mol/L aqueous sodium hydroxide solution and dilute hydrochloric acid, followed by extraction with ethyl acetate. The organic layer was washed with saturated aqueous sodium chloride solution, dried over anhydrous magnesium sulfate, and then concentrated under reduced pressure to afford 357 mg of the title compound as white foam. (Yield: 78%)

Mass spectrum (FAB, m/z): 534 (M⁺+1)

¹H-NMR spectrum (DMSO-d₆, δ ppm): 12.59 (brs, 0.5H), 8.67 (d, J=4.7 Hz, 1H), 8.01-7.95 (m, 3H), 7.85 (d, J=7.7 Hz, 1H), 7.76 (dd, J=8.4, 7.5 Hz, 1H), 7.61 (dd, J=7.2, 4.7 Hz, 1H), 7.50 (d, J=7.5 Hz, 1H), 7.36-7.27 (m, 3H), 6.75 (d, J=8.4 Hz, 1H), 6.44 (s, 1H), 6.37 (s, 1H), 4.72 (s, 2H), 4.42 (q, J=7.1 Hz, 2H), 4.33 (s, 2H), 3.87 (s, 2H), 1.37 (t, J=7.1 Hz, 3H)

Example 13

Ethyl (6-{[3'-(1-propynyl)biphenyl-4-ylmethyl](thiophen-2-ylsulfonyl)-aminomethyl}pyridin-2-ylamino)acetate To a solution of 533 mg (1.50 mmol) of ethyl {6-[(thiophen-2-ylsulfonyl)aminomethyl]pyridin-2-ylamino}acetate obtained in Reference Example 9-(b) in 8.0 mL of tetrahydrofuran, 333 mg (1.50 mmol) of 3'-(1-propynyl)biphenyl-4-ylmethanol obtained in the same manner as in Reference Example 13, 740 μL (3.00 mmol) of tri-n-butylphosphine, and 517 mg (3.00 mmol) of N,N,N',N'-tetramethylazodicarboxamide were added and stirred for 7 hours at room temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=1:0→1:1 (V/V)), and fractions containing the target product were concentrated under reduced pressure to afford 806 mg of the title compound as a colorless oil. (Yield: 96%)

Mass spectrum (CI, m/z): 560 (M⁺+1)

¹H-NMR spectrum (CDCl₃, δ ppm): 7.60-7.59 (m, 1H), 7.51 (dd, J=5.0, 1.3 Hz, 1H), 7.48-7.43 (m, 4H), 7.36-7.27 (m, 5H), 7.01 (dd, J=5.0, 3.8 Hz, 1H), 6.54 (d, J=6.9 Hz, 1H), 6.29 (d, J=8.0 Hz, 1H), 4.78 (t, J=5.4 Hz, 1H), 4.60 (s, 2H), 4.33 (s, 2H), 4.21 (q, J=7.1 Hz, 2H), 3.99 (d, J=5.4 Hz, 2H), 2.07 (s, 3H), 1.27 (t, J=7.1 Hz, 3H)

Example 14

(6-{[3'-(1-Propynyl)biphenyl-4-ylmethyl](thiophen-2-ylsulfonyl)-aminomethyl}pyridin-2-ylamino)acetic acid To a solution of 800 mg (1.43 mmol) of ethyl (6-{[3'-(1-propynyl)biphenyl-4-ylmethyl](thiophen-2-ylsulfonyl) aminomethyl}pyridin-2-ylamino)acetate obtained in Example 13 in 6.0 mL of ethanol, 6.0 mL (6.0 mmol) of 1 mol/L aqueous sodium hydroxide solution was added and stirred for 4 hours at room temperature. After the completion of the reaction, water was added to the reaction solution. Then pH of the solution was adjusted to 4.5 with 1 mol/L hydrochloric acid, followed by extraction with ethyl acetate. The organic layer was washed with saturated aqueous sodium chloride solution, dried over anhydrous sodium sulfate, and then concentrated under reduced pressure. The concentrated product was dissolved in 10 mL of ethyl acetate, followed by addition of 10 mL of n-hexane at 50° C., and then the solution was cooled to room temperature for 1.5 hours with stirring. The precipitated solid was collected by filtration and then dried under reduced pressure to afford 620 mg of the title compound as a white solid. (Yield: 82%)

Mass spectrum (ESI⁺, m/z): 532 (M⁺+1)

¹H-NMR spectrum (DMSO-d₅, δ ppm): 12.39 (brs, 0.9H), 7.91 (dd, J=5.0, 1.3 Hz, 1H), 7.64-7.59 (m, 4H), 7.54 (dd, J=3.8, 1.3 Hz, 1H), 7.43 (dd, J=7.7, 7.7 Hz, 1H), 7.38-7.32 (m, 3H), 7.26 (dd, J=8.3, 7.2 Hz, 1H), 7.13 (dd, J=5.0, 3.8 Hz, 1H), 6.80 (t, J=5.8 Hz, 1H), 6.41 (d, J=8.3 Hz, 1H), 6.35 (d, J=7.2 Hz, 1H), 4.59 (s, 2H), 4.18 (s, 2H), 3.84 (d, J=5.8 Hz, 2H), 2.07 (s, 3H)

Example 15

Ethyl (6-{(benzenesulfonyl)[3'-(1-propynyl)biphenyl-4-ylmethyl]-aminomethyl}pyridin-2-ylamino) acetate To a solution of 524 mg (1.50 mmol) of ethyl {6-[(benzenesulfonyl)aminomethyl]pyridin-2-ylamino}acetate obtained in Reference Example 10-(b) in 8.0 mL of tetrahydrofuran, 333 mg (1.50 mmol) of 3'-(1-propynyl)biphenyl-4-ylmethanol obtained in the same manner as in Reference Example 13, 740 μL (3.00 mmol) of tri-n-butylphosphine, and 517 mg (3.00 mmol) of N,N,N',N'-tetramethylazodicarboxamide were added and stirred for 2 hours at room temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=3:1→1:1 (V/V)), and fractions containing the target product were concentrated under reduced pressure to afford 809 mg of the title compound as a colorless oil. (Yield: 97%)

Mass spectrum (CI, m/z): 554 (M⁺+1)

¹H-NMR spectrum (CDCl₃, δ ppm): 7.78-7.75 (m, 2H), 7.59-7.58 (m, 1H), 7.53-7.40 (m, 6H), 7.37-7.25 (m, 5H), 6.48 (d, J=7.0 Hz, 1H), 6.27 (d, J=8.0 Hz, 1H), 4.74 (t, J=5.2

Hz, 1H), 4.58 (s, 2H), 4.32 (s, 2H), 4.21 (q, J=7.2 Hz, 2H), 3.90 (d, J=5.2 Hz, 2H), 2.07 (s, 3H), 1.27 (t, J=7.2 Hz, 3H)

Example 16

(6-{(Benzenesulfonyl)[3'-(1-propynyl)biphenyl-4-ylmethyl]aminomethyl}-pyridin-2-ylamino)acetic acid To a solution of 804 mg (1.45 mmol) of ethyl (6-{(benzenesulfonyl)[3'-(1-propynyl)biphenyl-4-ylmethyl]aminomethyl}pyridin-2-ylamino)acetate obtained in Example 15 in 6.0 mL of ethanol, 6.0 mL (6.0 mmol) of 1 mol/L aqueous sodium hydroxide solution was added and stirred for 4 hours at room temperature. After the completion of the reaction, water was added to the reaction solution. Then pH of the solution was adjusted to 4.5 with 1 mol/L hydrochloric acid, followed by extraction with ethyl acetate. The organic layer was washed with saturated aqueous sodium chloride solution, dried over anhydrous sodium sulfate, and then concentrated under reduced pressure. The concentrated product was dissolved in 10 mL of ethyl acetate, followed by addition of 10 mL of n-hexane at 50° C., and then the solution was cooled to room temperature for 2 hours with stirring. The precipitated solid was collected by filtration and then dried under reduced pressure to afford 724 mg of the title compound as a white solid. (Yield: 95%)

Mass spectrum (EsI$^+$, m/z): 526 (M$^+$+1)

$^1$H-NMR spectrum (DMSO-d$_6$, δ ppm): 12.40 (brs, 0.6H), 7.75-7.72 (m, 2H), 7.63-7.58 (m, 5H), 7.53-7.48 (m, 2H), 7.43 (dd, J=7.7, 7.7 Hz, 1H), 7.38-7.35 (m, 1H), 7.33-7.30 (m, 2H), 7.23 (dd, J=8.3, 7.2 Hz, 1H), 6.75 (t, J=5.6 Hz, 1H), 6.37 (d, J=8.3 Hz, 1H), 6.29 (d, J=7.2 Hz, 1H), 4.59 (s, 2H), 4.17 (s, 2H), 3.77 (d, J=5.6 Hz, 2H), 2.07 (s, 3H)

Example 17

Ethyl (6-{[3'-(1-propynyl)biphenyl-4-ylmethyl](thiophen-3-ylsulfonyl)-aminomethyl}pyridin-2-ylamino)acetate To a solution of 284 mg (0.800 mmol) of ethyl {6-[(thiophen-3-ylsulfonyl)aminomethyl]pyridin-2-ylamino}acetate obtained in Reference Example 11-(b) in 4.0 mL of tetrahydrofuran, 178 mg (0.800 mmol) of 3'-(1-propynyl)biphenyl-4-ylmethanol obtained in the same manner as in Reference Example 13, 395 μL (1.60 mmol) of tri-n-butylphosphine, and 276 mg (1.60 mmol) of N,N,N',N'-tetramethylazodicarboxamide were added and stirred for 3 hours at room temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=4:1→1:1 (V/V)), and fractions containing the target product were concentrated under reduced pressure to afford 432 mg of the title compound as a colorless syrup. (Yield: 97%)

Mass spectrum (CI, m/z): 560 (M$^+$+1)

$^1$H-NMR spectrum (CDCl$_3$, δ ppm): 7.80 (dd, J=3.1, 1.3 Hz, 1H), 7.60-7.59 (m, 1H), 7.50-7.45 (m, 3H), 7.36-7.28 (m, 6H), 7.17 (dd, J=5.1, 1.3 Hz, 1H), 6.52 (d, J=7.2 Hz, 1H), 6.31 (d, J=8.0 Hz, 1H), 4.80 (t, J=5.4 Hz, 1H), 4.61 (s, 2H), 4.32 (s, 2H), 4.21 (q, J=7.2 Hz, 2H), 3.99 (d, J=5.4 Hz, 2H), 2.08 (s, 3H), 1.27 (t, J=7.2 Hz, 3H)

Example 18

6-{[3'-(1-Propynyl)biphenyl-4-ylmethyl](thiophen-3-ylsulfonyl)-aminomethyl}pyridin-2-ylamino)acetic acid To a solution of 426 mg (0.762 mmol) of ethyl (6-{[3'-(1-propynyl)biphenyl-4-ylmethyl](thiophen-3-ylsulfonyl)aminomethyl}pyridin-2-ylamino)acetate obtained in Example 17 in 3.5 mL of ethanol, 3.5 mL (3.5 mmol) of 1 mol/L aqueous sodium hydroxide solution was added and stirred for 16 hours at room temperature. After the completion of the reaction, water was added to the reaction solution. Then pH of the solution was adjusted to 4.4 with 1 mol/L hydrochloric acid, followed by extraction with ethyl acetate. The organic layer was washed with saturated aqueous sodium chloride solution, dried over anhydrous sodium sulfate, and then concentrated under reduced pressure. To the concentrated product were added 5 mL of ethyl acetate and 5 mL of n-hexane and heated to 50° C., and then the solution was cooled to room temperature for 2 hours with stirring. The precipitated solid was collected by filtration and then dried under reduced pressure to afford 390 mg of the title compound as a white solid. (Yield: 96%)

Mass spectrum (CI, m/z): 532 (M$^+$+1)

$^1$H-NMR spectrum (DMSO-d$_6$, δ ppm): 12.46 (brs, 0.6H), 8.14 (dd, J=3.0, 1.4 Hz, 1H), 7.66 (dd, J=5.1, 3.0 Hz, 1H), 7.64-7.59 (m, 4H), 7.45-7.24 (m, 6H), 6.81 (t, =5.5 Hz, 1H), 6.40 (d, J=8.2 Hz, 1H), 6.33 (d, J=7.0 Hz, 1H), 4.58 (s, 2H), 4.16 (s, 2H), 3.84 (d, J=5.5 Hz, 2H), 2.07 (s, 3H)

Example 19

(6-{(3-Fluorobenzenesulfonyl)[3'-(1-propynyl)biphenyl-4-ylmethyl]-aminomethyl}pyridin-2-ylamino)acetic acid 19-(a): tert-Butyl [tert-butoxycarbonyl(6-{(3-fluorobenzenesulfonyl)-[3'-(1-propynyl)biphenyl-4-ylmethyl]aminomethyl}pyridin-2-yl)amino]acetate To a solution of 542 mg (1.00 mmol) of tert-butyl [tert-butoxycarbonyl(6-{[3'-(1-propynyl)biphenyl-4-ylmethyl]aminomethyl}pyridin-2-yl)amino]acetate obtained in Reference Example 12-(c) in 3.5 mL of methylene chloride, 280 μL (2.01 mmol) of triethylamine and 150 μL (1.13 mmol) of 3-fluorobenzenesulfonyl chloride were added under ice cooling and stirred for 2 hours at room temperature. After the completion of the reaction, water was added to the reaction solution, followed by extraction with methylene chloride. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=9:1→7:3 (V/V)), and fractions containing the target product were concentrated under reduced pressure to afford 673 mg of the title compound as a white foam. (Yield: 96%)

Mass spectrum (CI, m/z): 700 (M$^+$+1)

$^1$H-NMR spectrum (CDCl$_3$, δ ppm): 7.70 (d, J=8.1 Hz, 1H), 7.59-7.58 (m, 1H), 7.53-7.32 (m, 9H), 7.27-7.19 (m, 3H), 6.87 (d, J=7.3 Hz, 1H), 4.57 (s, 2H), 4.39 (s, 2H), 4.37 (s, 2H), 2.08 (s, 3H), 1.52 (s, 9H), 1.42 (s, 9H)

19-(b): (6-{(3-Fluorobenzenesulfonyl)[3'-(1-propynyl)biphenyl-4-ylmethyl]-aminomethyl}pyridin-2-ylamino)acetic acid To a solution of 595 mg (0.850 mmol) of tert-butyl [tert-butoxycarbonyl(6-{(3-fluorobenzenesulfonyl)[3'-(1-propynyl)biphenyl-4-ylmethyl]aminomethyl}pyridin-2-yl)amino]acetate obtained in Example 19-(a) in 5.0 mL of tetrahydrofuran, 5.0 mL (20 mmol) of 4 mol/L hydrochloric acid was added, and stirred at 70° C. for 5 hours. After the completion of the reaction, pH of the solution was adjusted to 4.5 with 1 mol/L aqueous sodium hydroxide solution, followed by extraction with ethyl acetate. The organic layer was washed with saturated aqueous sodium chloride solution, dried over anhydrous sodium sulfate, and then concentrated under reduced pressure. To the concentrated product were added 10 mL of ethyl acetate and 5 mL of n-hexane and heated to 50° C., and then the solution was cooled to room temperature for 2 hours with stirring. The precipitated solid was collected by filtration and then dried under reduced pressure to afford 429 mg of the title compound as a white solid. (Yield: 93%)

Mass spectrum (ESI$^+$, m/z): 544 (M$^+$+1)

$^1$H-NMR spectrum (DMSO-d$_6$, δ ppm): 12.41 (brs, 0.9H), 7.65-7.60 (m, 4H), 7.58-7.50 (m, 2H), 7.46-7.34 (m, 6H), 7.25 (dd, J=8.3, 7.2 Hz, 1H), 6.79 (t, J=5.7 Hz, 1H), 6.38 (d, J=8.3 Hz, 1H), 6.32 (d, J=7.2 Hz, 1H), 4.67 (s, 2H), 4.19 (s, 2H), 3.74 (d, J=5.7 Hz, 2H), 2.07 (s, 3H)

Example 20

Isopropyl (6-{[3'-(1-propynyl)biphenyl-4-ylmethyl](pyridin-2-ylsulfonyl)-aminomethyl}pyridin-2-ylamino)acetate To a solution of 1.05 g (2.88 mmol) of isopropyl {6-[(pyridin-2-ylsulfonyl)aminomethyl]pyridin-2-ylamino}acetate obtained in Reference Example 14 in 15.0 mL of tetrahydrofuran, 640 mg (2.88 mmol) of 3'-(1-propynyl)biphenyl-4-ylmethanol obtained in the same manner as in Reference Example 13, 1.42 mL (5.76 mmol) of tri-n-butylphosphine, and 992 mg (5.76 mmol) of N,N,N',N'-tetramethylazodicarboxamide were added and stirred for 3 hours at room temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=3:2→2:3 (V/V)), and fractions containing the target product were concentrated under reduced pressure to afford 1.59 g of the title compound as a colorless syrup. (Yield: 97%)

Mass spectrum (CI, m/z): 569 (M$^+$+1)

$^1$H-NMR spectrum (CDCl$_3$, δ ppm): 8.62 (ddd, J=4.7, 1.7, 1.0 Hz, 1H), 7.83 (ddd, J=7.7, 1.0, 1.0 Hz, 1H), 7.76 (ddd, J=7.7, 7.7, 1.7 Hz, 1H), 7.60-7.58 (m, 1H), 7.47-7.43 (m, 3H), 7.38 (ddd, J=7.7, 4.7, 1.0 Hz, 1H), 7.36-7.32 (m, 4H), 7.23 (dd, J=8.2, 7.3 Hz, 1H), 6.50 (d, J=7.3 Hz, 1H), 6.22 (d, J=8.2 Hz, 1H), 5.09 (sep, J=6.3 Hz, 1H), 4.79 (s, 2H), 4.70 (t, J=5.3 Hz, 1H), 4.42 (s, 2H), 3.92 (d, J=5.3 Hz, 2H), 2.08 (s, 3H), 1.26 (d, J=6.3 Hz, 6H)

The compounds used in Examples were synthesized as described below.

Reference Example 1

Ethyl {6-[(pyridin-2-ylsulfonyl)aminomethyl]pyridin-2-ylamino}acetate 1-(a): tert-Butyl [tert-butoxycarbonyl(6-ethoxycarbonylpyridin-2-yl)-amino]acetate To a solution of 15.7 g (0.360 mol) of sodium hydride (55 wt. % mineral oil dispersion) in 362 mL of N,N-dimethylformamide, a solution of 81.2 g (0.305 mol) of 6-tert-butoxycarbonylamino-pyridine-2-carboxylic acid ethyl ester (see WO2006/074884) in 300 mL of N,N-dimethylformamide was added dropwise for 20 minutes under ice cooling in an argon atmosphere, and stirred for 1 hour at room temperature. Thereafter, 54.0 mL (0.366 mol) of tert-butyl bromoacetate was added dropwise for 10 minutes under ice cooling, and further stirred for 1 hour at room temperature. After the completion of the reaction, an aqueous solution in which 1.77 g (33.0 mmol) of ammonium chloride and 300 mL of water were dissolved was added to the reaction solution, followed by extraction with toluene. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=9:1→4:1 (V/V)), and fractions containing the target product were concentrated under reduced pressure to afford 108 g of the title compound as a pale yellow oil. (Yield: 93%)

Mass spectrum (CI, m/z): 381 (M$^+$+1)

$^1$H-NMR spectrum (CDCl$_3$, δ ppm): 8.04 (d, J=7.8 Hz, 1H), 7.81 (dd, J=7.6, 1.5 Hz, 1H), 7.76 (dd, J=7.8, 7.6 Hz, 1H), 4.67 (s, 2H), 4.40 (q, J=7.1 Hz, 2H), 1.52 (s, 9H), 1.45 (s, 9H), 1.40 (t, J=7.1 Hz, 3H)

1-(b): tert-Butyl [tert-butoxycarbonyl(6-hydroxymethylpyridin-2-yl)-amino]acetate To a solution of 98.8 g (0.260 mol) of tert-butyl [tert-butoxycarbonyl(6-ethoxycarbonylpyridin-2-yl)amino]acetate obtained in Reference Example 1-(a) in 195 mL of ethanol, a solution of 34.6 g (0.312 mol) of calcium chloride in 195 mL of ethanol was added dropwise for 20 minutes under ice cooling. After the completion of dropwise addition, 105 mL (0.315 mol) of 3 mol/L sodium borohydride/tetraethylene glycol dimethyl ether solution was added dropwise for 20 minutes at 35° C. or lower, and then further stirred for 15 minutes at room temperature. After the completion of the reaction, the reaction solution was added dropwise to a mixed solution of 17.8 mL of acetic acid and 195 mL of water for 10 minutes under ice cooling, and stirred for 1 hour at room temperature. Thereafter, 315 mL of water was added to the solution, followed by extraction with toluene. The organic layer was sequentially washed with saturated aqueous sodium bicarbonate solution, water, and then saturated aqueous sodium chloride solution, and concentrated under reduced pressure. The residue was subjected to silica gel column chromatography (elution solvent; n-hexane:ethyl acetate=4:1→3:2 (V/V)), and fractions containing the target product were concentrated under reduced pressure to afford 81.1 g of the title compound as a pale yellow oil. (Yield: 92%)

Mass spectrum (CI, m/z): 339 (M$^+$+1)

$^1$H-NMR spectrum (CDCl$_3$, δ ppm): 7.74 (d, J=8.2 Hz, 1H), 7.63 (dd, J=8.2, 7.4 Hz, 1H), 6.93-6.98 (m, 1H), 4.68-4.65 (m, 2H), 4.54 (s, 2H), 3.39 (t, J=5.3 Hz, 1H), 1.54 (s, 9H), 1.46 (s, 9H)

1-(c): tert-Butyl [tert-butoxycarbonyl(6-formylpyridin-2-yl)amino]acetate

To a solution of 12.9 g (30.4 mmol) of the Dess-Martin reagent in 130 mL of methylene chloride, a solution of 10.0 g (29.6 mmol) of tert-butyl [tert-butoxycarbonyl(6-hydroxymethylpyridin-2-yl)amino]acetate obtained in Reference Example 1-(b) in 50 mL of methylene chloride was added dropwise for 20 minutes under ice cooling in an argon atmosphere. After the completion of the dropwise addition, the solution was stirred for 2 hours at room temperature. After the completion of the reaction, 305 mL of 0.1 wt. % aqueous sodium thiosulfate solution was added to the reaction solution, followed by extraction with methylene chloride. The organic layer was sequentially washed with 0.5 mol/L aqueous sodium hydroxide solution and saturated aqueous sodium chloride solution, and then dried over anhydrous magnesium sulfate. Thereafter, by concentrating under reduced pressure, 9.61 g of the title compound was obtained substantially quantitatively as a slightly yellow oil.

Mass spectrum (EI, m/z): 336 (M$^+$)

$^1$H-NMR spectrum (DMSO-d$_6$, δ ppm): 9.82 (s, 1H), 8.11-7.99 (m, 2H), 7.68 (dd, J=6.6, 1.5 Hz, 1H), 4.58 (s, 2H), 1.48 (s, 9H), 1.42 (s, 9H)

1-(d): tert-Butyl [tert-butoxycarbonyl(6-hydroxyiminomethylpyridin-2-yl)-amino]acetate To a solution of 2.88 g (8.56 mmol) of tert-butyl [tert-butoxycarbonyl(6-formylpyridin-2-yl)amino]acetate obtained in Reference Example 1-(c) in 29 mL of methanol, 0.650 g (9.35 mmol) of hydroxylammonium chloride and 3.5 mL (43 mmol) of pyridine were added and stirred for 1 hour at room temperature. After the completion of the reaction, the reaction solution was concentrated under reduced pressure. To the obtained residue, ethyl acetate was added, and the residue was sequentially washed with a 5 wt. % aqueous potassium hydrogen sulfate solution, saturated aqueous sodium bicarbonate solution, and saturated aqueous sodium chloride solution. Then, the residue was dried over anhydrous magnesium sulfate and concentrated under reduced pressure. The residue was subjected to silica gel column chromatography (elution solvent; n-hexane:ethyl acetate=3:2 (V/V)), and fractions containing the target product were concentrated under reduced pressure to afford 2.76 g of the title compound as a colorless oil. (Yield: 92%)

Mass spectrum (EI, m/z): 351 (M$^+$)

$^1$H-NMR spectrum (CDCl$_3$, δ ppm): 8.06 (s, 1H), 7.91 (s, 1H), 7.85 (d, J=8.2 Hz, 1H), 7.65 (dd, J=8.2, 7.6 Hz, 1H), 7.47 (dd, J=7.6, 0.7 Hz, 1H), 4.59 (s, 2H), 1.53 (s, 9H), 1.45 (s, 9H)

1-(e): tert-Butyl [(6-aminomethylpyridin-2-yl)tert-butoxycarbonylamino]acetate

To a solution of 2.75 g (7.83 mmol) of tert-butyl [tert-butoxycarbonyl(6-hydroxyiminomethylpyridin-2-yl)amino]acetate obtained in Reference Example 1-(d) in 49 mL of ethanol, 0.98 g of 10 wt. % palladium-activated carbon (containing 50 wt. % of water) was added and stirred for 1 hour at room temperature in a hydrogen atmosphere at 1 atm. After the completion of the reaction, insoluble substances were filtered off. The filtrate was then concentrated under reduced pressure to afford 2.48 g of the title compound as a colorless oil. (Yield: 94%)

Mass spectrum (CI, m/z): 338 (M$^+$+1)

$^1$H-NMR spectrum (CDCl$_3$, δ ppm): 7.68 (d, J=8.3 Hz, 1H), 7.58 (dd, J=8.3, 7.4 Hz, 1H), 6.91 (d, J=7.4 Hz, 1H), 4.57 (s, 2H), 3.85 (s, 2H), 1.53 (s, 9H), 1.46 (s, 9H)

1-(f): tert-Butyl (tert-butoxycarbonyl {6-[(pyridin-2-ylsulfonyl)aminomethyl]-pyridin-2-yl}amino)acetate To a solution of 0.640 g (3.60 mmol) of 2-pyridylsulfonyl chloride in 14 mL of methylene chloride, a solution of 1.20 g (3.56 mmol) of tert-butyl [(6-aminomethylpyridin-2-yl) tert-butoxycarbonylamino]acetate obtained in Reference Example 1-(e) and 2.24 mL (16.2 mmol) of triethylamine in 12 mL methylene chloride was added and stirred for 0.5 hours at room temperature. After the completion of the reaction, a 5 wt. % aqueous potassium hydrogen sulfate solution was added to the reaction solution, followed by extraction with methylene chloride. The organic layer was sequentially washed with saturated aqueous sodium bicarbonate solution and saturated aqueous sodium chloride solution. Then, the residue was dried over anhydrous magnesium sulfate and concentrated under reduced pressure. The residue was subjected to silica gel column chromatography (elution solvent; n-hexane:ethyl acetate=1:1 (V/V)), and fractions containing the target product were concentrated under reduced pressure to afford 1.46 g of the title compound as a white solid. (Yield: 86%)

Mass spectrum (APCI, m/z): 479 (M$^+$+1)

$^1$H-NMR spectrum (CDCl$_3$, δ ppm): 8.56 (ddd, J=4.7, 1.7, 0.9 Hz, 1H), 7.97 (ddd, J=7.8, 1.1, 0.9 Hz, 1H), 7.84 (ddd, J=7.8, 7.7, 1.7 Hz, 1H), 7.68 (d, J=8.4 Hz, 1H), 7.52 (dd, J=8.4, 7.4 Hz, 1H), 7.40 (ddd, J=7.7, 4.7, 1.1 Hz, 1H), 6.84 (dd, J=7.4, 0.5 Hz, 1H), 5.86 (t, J=5.6 Hz, 1H), 4.48 (s, 2H), 4.36 (d, J=5.6 Hz, 2H), 1.53 (s, 9H), 1.45 (s, 9H)

1-(g): Ethyl {6-[(pyridin-2-ylsulfonyl)aminomethyl] pyridin-2-ylamino}acetate

To 3.59 g (7.50 mmol) of tert-butyl (tert-butoxycarbonyl {6-[(pyridin-2-ylsulfonyl)aminomethyl]pyridin-2-yl}amino)acetate obtained in the same manner as in Reference Example 1-(f), 37.5 mL (75.0 mmol) of 2 mol/L hydrogen chloride/ethanol solution was added and heated to reflux for 3 hours with stirring. After the completion of the reaction, water was added to the reaction solution, and the reaction solution was neutralized with 1 mol/L aqueous sodium hydroxide solution, followed by extraction with ethyl acetate. The organic layer was washed with saturated aqueous sodium chloride solution, dried over anhydrous magnesium sulfate, and then concentrated under reduced pressure to afford 2.17 g of the title compound as a brown oil. (Yield: 83%)

Mass spectrum (CI, m/z): 351 (M$^+$+1)

$^1$H-NMR spectrum (DMSO-d$_6$, δ ppm): 8.71 (ddd, J=4.8, 1.8, 0.8 Hz, 1H), 8.18 (brs, 0.1H), 8.05 (ddd, J=7.8, 7.6, 1.8 Hz, 1H), 7.91 (ddd, J=7.8, 1.0, 0.8 Hz, 1H), 7.64 (ddd, J=7.6, 4.6, 1.0 Hz, 1H), 7.33 (dd, J=8.1, 7.2 Hz, 1H), 6.86 (t, J=6.1 Hz, 0.2H), 6.52 (d, J=7.2 Hz, 1H), 6.39 (d, J=8.1 Hz, 1H), 4.08 (q, J=7.1 Hz, 2H), 4.01 (s, 2H), 3.95 (s, 2H), 1.16 (t, J=7.1 Hz, 3H)

Reference Example 2

Ethyl {6-[(pyridin-3-ylsulfonyl)aminomethyl]pyridin-2-ylamino}acetate 2-(a): tert-Butyl (tert-butoxycarbonyl{6-[(pyridin-3-ylsulfonyl)aminomethyl]-pyridin-2-yl}amino)acetate The reaction and post-treatment were performed in accordance with Reference Example 1-(f) except for using 1.20 g (3.56 mmol) of tert-butyl [(6-aminomethylpyridin-2-yl)tert-butoxycarbonylamino]acetate obtained in the same manner as in Reference Example 1-(e), and using 640 mg (3.60 mmol) of 3-pyridylsulfonyl chloride in place of 2-pyridylsulfonyl chloride, to afford 1.45 g of the title compound as a colorless oil. (Yield: 85%)

Mass spectrum (CI, m/z): 479 (M$^+$+1)

$^1$H-NMR spectrum (CDCl$_3$, δ ppm): 9.06 (d, J=2.2 Hz, 1H), 8.71 (dd, J=4.6, 1.5 Hz, 1H), 8.13-8.08 (m, 1H), 7.68 (d, J=8.2 Hz, 1H), 7.52 (dd, J=8.2, 7.4 Hz, 1H), 7.38-7.32 (m, 1H), 6.77 (d, J=7.4 Hz, 1H), 5.80 (t, J=5.1 Hz, 1H), 4.40 (s, 2H), 4.24 (d, J=5.1 Hz, 2H), 1.53 (s, 9H), 1.46 (s, 9H)

2-(b): Ethyl {6-[(pyridin-3-ylsulfonyl)aminomethyl] pyridin-2-ylamino}acetate

The reaction and post-treatment were performed in accordance with Reference Example 1-(g) except for using 1.00 g (2.09 mmol) of tert-butyl (tert-butoxycarbonyl {6-[(pyridin-3-ylsulfonyl)aminomethyl]pyridin-2-yl}amino)acetate obtained in the same manner as in Reference Example 2-(a) in place of tert-butyl (tert-butoxycarbonyl {6-[(pyridin-2-ylsulfonyl)aminomethyl]pyridin-2-yl}amino)acetate, and using 10.4 mL (20.8 mmol) of 2 mol/L hydrogen chloride/ethanol solution, to afford 686 mg of the title compound as a brown oil. (Yield: 94%)

$^1$H-NMR spectrum (CDCl$_3$, δ ppm): 9.06 (dd, J=2.3, 0.7 Hz, 1H), 8.71 (dd, J=4.9, 1.6 Hz, 1H), 8.09 (ddd, J=8.0, 2.3, 1.6 Hz, 1H), 7.35 (ddd, J=8.0, 4.9, 0.7 Hz, 1H), 7.28 (dd, J=8.3, 7.3 Hz, 1H), 6.38 (d, J=7.3 Hz, 1H), 6.29 (d, J=8.3 Hz, 1H), 5.95 (t, J=5.4 Hz, 1H), 4.96 (t, J=5.4 Hz, 1H), 4.27 (q, J=7.2 Hz, 2H), 4.14 (d, J=5.4 Hz, 2H), 4.03 (d, J=5.4 Hz, 2H), 1.32 (t, J=7.2 Hz, 3H)

Reference Example 3

3'-(1-Propenyl)biphenyl-4-ylmethanol 3-(a): 3'-(1-Propenyl)biphenyl-4-ylcarbaldehyde To 500 mg (1.91 mmol) of 3'-bromobiphenyl-4-ylcarbaldehyde (see Journal of Organic Chemistry, 68, 247 (2003)), 27.5 mL of toluene and 1.65 mL of water were added, and then 1.63 g (7.68 mmol) of tripotassium phosphate and 656 mg (7.64 mmol) of 1-propenylboronic acid were added. Thereafter, the mixture was placed in a nitrogen gas atmosphere. Furthermore, 6.2 mg (0.028 mmol) of palladium acetate and 20.2 mg (0.0563 mmol) of butyldi-1-adamantylphosphine were added and stirred for 4.5 hours at 100° C. in a nitrogen gas atmosphere. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=4:1 (V/V)), and fractions containing the target product were concentrated under reduced pressure to afford 420 mg of the title compound as a slightly yellow oil. (Yield: 99%)

Mass spectrum (CI, m/z): 223 (M$^+$+1)

$^1$H-NMR spectrum (CDCl$_3$, δ ppm): 10.06 (s, 1H), 7.98-7.92 (m, 2H), 7.79-7.72 (m, 2H), 7.59-7.55 (m, 1H), 7.49-7.42 (m, 1H), 7.41-7.37 (m, 2H), 6.48 (dd, J 15.9, 1.5 Hz, 1H), 6.33 (dq, J=15.9, 6.3 Hz, 1H), 1.92 (dd, J=6.3, 1.5 Hz, 3H)

3-(b): 3'-(1-Propenyl)biphenyl-4-ylmethanol

To a solution of 417 mg (1.88 mmol) of 3'-(1-propenyl)biphenyl-4-ylcarbaldehyde obtained in Reference Example 3-(a) in 4.6 mL of ethanol, 35.6 mg (0.941 mmol) of sodium borohydride was added at room temperature and stirred for 45 minutes at the same temperature. After the completion of the reaction, saturated aqueous ammonium chloride solution was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=7:3 (V/V)), and fractions containing the target product were concentrated under reduced pressure to afford 401 mg of the title compound as a white solid. (Yield: 95%)

Mass spectrum (EI, m/z): 224 (M$^+$)

$^1$H-NMR spectrum (CDCl$_3$, δ ppm): 7.63-7.56 (m, 2H), 7.55-7.52 (m, 1H), 7.47-7.29 (m, 5H), 6.47 (dd, J=15.9, 1.5 Hz, 1H), 6.31 (dq, J=15.9, 6.6 Hz, 1H), 4.74 (d, J=5.7 Hz, 2H), 1.91 (dd, J=6.6, 1.5 Hz, 3H), 1.70 (t, J=5.7 Hz, 1H)

Reference Example 4

3'-(1-Propynyl)biphenyl-4-ylmethanol 4-(a): 3'-(1-Propynyl)biphenyl-4-ylcarbaldehyde A solution of 1.04 g (3.98 mmol) of 3'-bromobiphenyl-4-ylcarbaldehyde in 10 mL of toluene was degassed under reduced pressure and then substituted with argon gas. Thereafter, 231 mg (0.200 mmol) of tetrakis(triphenylphosphine) palladium and 1.46 mL (4.80 mmol) of tributyl(1-propynyl) tin were added and stirred for 7 hours at 110° C. in an argon gas atmosphere. After the completion of the reaction, 60 mL of 0.8 mol/L aqueous potassium fluoride solution was added to the reaction solution, followed by extraction with toluene. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=1:0→4:1 (V/V)), and fractions containing the target product were concentrated under reduced pressure to afford 660 mg of the title compound as a pale yellow solid. (Yield: 75%)

Mass spectrum (CI, m/z): 221 (M$^+$+1)

$^1$H-NMR spectrum (CDCl$_3$, δ ppm): 10.06 (s, 1H), 7.97-7.93 (m, 2H), 7.76-7.72 (m, 2H), 7.68-7.67 (m, 1H), 7.55-7.52 (m, 1H), 7.45-7.37 (m, 2H), 2.08 (s, 3H)

4-(b): 3'-(1-Propynyl)biphenyl-4-ylmethanol

The reaction and post-treatment were performed in accordance with Reference Example 3-(b) except for using 723 mg (3.28 mmol) of 3'-(1-propynyl)biphenyl-4-ylcarbaldehyde obtained in the same manner as in Reference Example 4-(a) in place of 3'-(1-propenyl)biphenyl-4-ylcarbaldehyde, and using 62.2 mg (1.64 mmol) of sodium borohydride, to afford 588 mg of the title compound as a pale yellowish white solid. (Yield: 81%)

Mass spectrum (EI, m/z): 222 (M$^+$)

$^1$H-NMR spectrum (CDCl$_3$, δ ppm): 7.63-7.62 (m, 1H), 7.60-7.56 (m, 2H), 7.51-7.47 (m, 1H), 7.46-7.42 (m, 2H), 7.38-7.32 (m, 2H), 4.75 (d, J=6.0 Hz, 2H), 2.07 (s, 3H), 1.68 (t, J=6.0 Hz, 1H)

Reference Example 5

3'-Ethoxybiphenyl-4-ylmethanol

To 1.21 g (6.02 mmol) of 3-bromophenetole were added 15 mL of toluene, 15 mL of ethanol, and 4.5 mL (9.0 mmol) of 2 mol/L aqueous sodium carbonate solution, degassed under reduced pressure, and then substituted with argon gas. Thereafter, 1.37 g (9.02 mmol) of 4-(hydroxymethyl)phenylboronic acid and 347 mg (0.300 mmol) of tetrakis(triphenylphosphine)palladium were added and stirred for 4 hours at 100° C. in an argon gas atmosphere. After the completion of the reaction, the reaction solution was concentrated under reduced pressure. Thereafter, water was added to the residue, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=9:1→7:3 (V/V)), and fractions containing the target product were concentrated under reduced pressure to afford 1.23 g of the title compound as a pale yellow oil. (Yield: 90%)

Mass spectrum (CI, m/z): 229 (M$^+$+1)

$^1$H-NMR spectrum (CDCl$_3$, δ ppm): 7.61-7.56 (m, 2H), 7.46-7.41 (m, 2H), 7.34 (dd, J=8.0, 8.0 Hz, 1H,), 7.18-7.11 (m, 2H), 6.91-6.87 (m, 1H), 4.74 (d, J=5.9 Hz, 2H), 4.10 (q, J=7.0 Hz, 2H), 1.67 (t, J=5.9 Hz, 1H), 1.45 (t, J=7.0 Hz, 3H)

Reference Example 6

Hexyl {6-[(pyridin-2-ylsulfonyl)aminomethyl]pyridin-2-ylamino}acetate

To a solution of 957 mg (2.00 mmol) of tert-butyl (tert-butoxycarbonyl {6-[(pyridin-2-ylsulfonyl)aminomethyl]pyridin-2-yl}amino)acetate obtained in the same manner as in Reference Example 1-(f) in 6.0 mL of n-hexanol, 0.56 mL (10 mmol) of concentrated sulfuric acid was added and stirred for 8 hours at 100° C. After the completion of the reaction, the reaction solution was poured into saturated aqueous sodium bicarbonate solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=1:1→3:7 (V/V)), and fractions containing the target product were concentrated under reduced pressure to afford 658 mg of the title compound as a slightly yellow oil. (Yield: 81%)

$^1$H-NMR spectrum (CDCl$_3$, δ ppm): 8.62 (ddd, J=4.6, 1.8, 1.0 Hz, 1H), 7.97 (ddd, J=7.7, 1.2, 1.0 Hz, 1H), 7.84 (ddd, J=7.7, 7.7, 1.8 Hz, 1H), 7.41 (ddd, J=7.7, 4.6, 1.2 Hz, 1H), 7.29 (dd, J=8.4, 7.4 Hz, 1H), 6.44 (d, J=7.4 Hz, 1H), 6.28 (d, J=8.4 Hz, 1H), 6.02 (t, J=5.3 Hz, 1H), 4.92 (t, J=5.3 Hz, 1H), 4.25 (d, J=5.3 Hz, 2H), 4.18 (t, J=6.7 Hz, 2H), 4.08 (d, J=5.3 Hz, 2H), 1.71-1.61 (m, 2H), 1.39-1.26 (m, 6H), 0.91-0.87 (m, 3H)

Reference Example 7 tert-Butyl (tert-butoxycarbonyl{6-[(3'-ethoxybiphenyl-4-ylmethyl)aminomethyl]pyridine-2-yl}amino) acetate 7-(a): 3'-Ethoxybiphenyl-4-ylcarbaldehyde The reaction and post-treatment were performed in accordance with Reference Example 5 except for using 4.20 g (22.7 mmol) of 4-bromobenzaldehyde in place of 3-bromophenetole, using 3.13 g (18.9 mmol) of 3-ethoxyphenylboronic acid in place of 4-(hydroxymethyl)phenylboronic acid, and using 28.4 mL (56.8 mmol) of 2 mol/L aqueous sodium carbonate solution and 2.18 g (1.89 mmol) of tetrakis(triphenylphosphine)palladium, to afford 4.08 g of the title compound as a colorless oil. (Yield: 95%)

Mass spectrum (CI, m/z): 227 (M$^+$+1)

$^1$H-NMR spectrum (CDCl$_3$, δ ppm): 10.06 (s, 1H), 7.97-7.93 (m, 2H), 7.76-7.73 (m, 2H), 7.38 (dd, J=8.1, 7.9 Hz, 1H), 7.21 (ddd, J=7.9, 2.0, 0.9 Hz, 1H), 7.16 (dd, J=2.3, 2.0 Hz, 1H), 6.95 (ddd, J=8.1, 2.3, 0.9 Hz, 1H), 4.11 (q, J=6.9 Hz, 2H), 1.46 (t, J=6.9 Hz, 3H)

7-(b): tert-Butyl (tert-butoxycarbonyl{6-[(3'-ethoxybiphenyl-4-ylmethyl)-aminomethyl]pyridin-2-yl}amino)acetate To a solution of 4.02 g (11.9 mmol) of tert-butyl [(6-aminomethylpyridin-2-yl)tert-butoxycarbonylamino]acetate obtained in the same manner as in Reference Example 1-(e) in 12 mL of methylene chloride, 2.46 g (10.9 mmol) of 3'-ethoxybiphenyl-4-ylcarbaldehyde obtained in Reference Example 7-(a) was added and stirred for 30 minutes at room temperature. Thereafter, 3.25 g (15.3 mmol) of sodium triacetoxyborohydride was added under ice cooling and stirred for 3.5 hours at the same temperature. After the completion of the reaction, an aqueous sodium bicarbonate solution was added to the reaction solution, followed by extraction with ethyl acetate. The organic layer was washed with saturated aqueous sodium chloride solution, dried over anhydrous potassium carbonate, and then concentrated under reduced pressure. The residue was subjected to silica gel column chromatography (elution solvent; n-hexane:ethyl acetate=3:2→0:1 (V/V)), and fractions containing the target product were concentrated under reduced pressure to afford 3.68 g of the title compound as a pale yellow oil. (Yield: 62%)

Mass spectrum (CI, m/z): 548 (M$^+$+1)

$^1$H-NMR spectrum (CDCl$_3$, δ ppm): 7.69 (d, J=8.2 Hz, 1H), 7.59 (dd, J=8.2, 7.3 Hz, 1H), 7.57-7.53 (m, 2H), 7.43-7.39 (m, 2H), 7.33 (dd, J=7.9, 7.7 Hz, 1H), 7.16 (ddd, J=7.7, 1.7, 0.9 Hz, 1H), 7.12 (dd, J=2.3, 1.7 Hz, 1H), 6.97 (d, J=7.3 Hz, 1H), 6.87 (ddd, J=7.9, 2.3, 1.0 Hz, 1H), 4.57 (s, 2H), 4.10 (q, J=7.1 Hz, 2H), 3.84 (s, 2H), 3.83 (s, 2H), 1.53 (s, 9H), 1.44 (t, J=7.1 Hz, 3H), 1.42 (s, 9H)

Reference Example 8

4-(6-Ethoxypyridin-2-yl)phenylmethanol

The reaction and post-treatment were performed in accordance with Reference Example 5 except for using 0.49 g (2.4 mmol) of 2-bromo-6-ethoxypyridine (see US2003/199440) in place of 3-bromophenetole, and using 0.59 g (3.9 mmol) of 4-(hydroxymethyl)phenylboronic acid, 1.7 mL (3.4 mmol) of 2 mol/L aqueous sodium carbonate solution, and 138 mg (0.119 mmol) of tetrakis(triphenylphosphine)palladium, to afford 284 mg of the title compound as a white solid. (Yield: 51%)

Mass spectrum (CI, m/z): 230 ($M^+ +1$)

$^1$H-NMR spectrum (CDCl$_3$, δ ppm): 8.05-8.01 (m, 2H), 7.62 (dd, J=8.2, 7.4 Hz, 1H), 7.47-7.43 (m, 2H), 7.32 (dd, J=7.4, 0.6 Hz, 1H), 6.67 (dd, J=8.2, 0.6 Hz, 1H), 4.75 (d, J=6.0 Hz, 2H), 4.49 (q, J=7.1 Hz, 2H), 1.67 (t, J=6.0 Hz, 1H), 1.44 (t, J=7.1 Hz, 3H)

Reference Example 9

Ethyl {6-[(thiophen-2-ylsulfonyl)aminomethyl]pyridin-2-ylamino}acetate 9-(a): tert-Butyl (tert-butoxycarbonyl {6-[(thiophen-2-ylsulfonyl)-aminomethyl]pyridin-2-yl}amino)acetate The reaction and post-treatment were performed in accordance with Reference Example 1-(f) except for using 1.35 g (4.00 mmol) of tert-butyl [(6-aminomethylpyridin-2-yl)tert-butoxycarbonylamino]acetate obtained in the same manner as in Reference Example 1-(e), and using 731 mg (4.00 mmol) of 2-thiophenesulfonyl chloride in place of 2-pyridylsulfonyl chloride, to afford 1.61 g of the title compound as a white solid. (Yield: 84%)

Mass spectrum (CI, m/z): 484 ($M^+ +1$)

$^1$H-NMR spectrum (CDCl$_3$, δ ppm): 7.71 (d, J=8.4 Hz, 1H), 7.57 (dd, J=3.8, 1.3 Hz, 1H), 7.56 (dd, J=8.4, 7.4 Hz, 1H), 7.50 (dd, J=5.0, 1.3 Hz, 1H), 7.01 (dd, J=5.0, 3.8 Hz, 1H), 6.83 (d, J=7.4 Hz, 1H), 5.67 (t, J=5.3 Hz, 1H), 4.45 (s, 2H), 4.27 (d, J=5.3 Hz, 2H), 1.53 (s, 9H), 1.47 (s, 9H)

9-(b): Ethyl {6-[(thiophen-2-ylsulfonyl)aminomethyl]-pyridin-2-ylamino}acetate

To 1.60 g (3.31 mmol) of tert-butyl (tert-butoxycarbonyl {6-[(thiophen-2-yl-sulfonyl)aminomethyl]pyridin-2-yl}amino)acetate obtained in Reference Example 9-(a), 20 mL (40 mmol) of 2 mol/L hydrogen chloride/ethanol solution was added and heated to reflux with stirring for 3 hours. After the completion of the reaction, the reaction solution was concentrated under reduced pressure and was neutralized using saturated aqueous sodium bicarbonate solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=7:3→1:1 (V/V)), and fractions containing the target product were concentrated under reduced pressure to afford 1.10 g of the title compound as a colorless oil. (Yield: 93%)

Mass spectrum (CI, m/z): 356 ($M^+ +1$)

$^1$H-NMR spectrum (CDCl$_3$, δ ppm): 7.57 (dd, J=3.8, 1.3 Hz, 1H), 7.51 (dd, J=5.0, 1.3 Hz, 1H), 7.32 (dd, J=8.3, 7.3 Hz, 1H), 7.01 (dd, J=5.0, 3.8 Hz, 1H), 6.44 (dd, J=7.3, 0.6 Hz, 1H), 6.32 (dd, J=8.3, 0.6 Hz, 1H), 5.86 (t, J=4.9 Hz, 1H), 4.96 (t, J=5.3 Hz, 1H), 4.26 (q, J=7.2 Hz, 2H), 4.18 (d, J=4.9 Hz, 2H), 4.06 (d, J=5.3 Hz, 2H), 1.32 (t, J=7.2 Hz, 3H)

Reference Example 10

Ethyl {6-[(benzenesulfonyl)aminomethyl]pyridin-2-ylamino}acetate 10-(a): tert-Butyl ({6-[(benzenesulfonyl)aminomethyl]pyridin-2-yl}-tert-butoxycarbonylamino)acetate The reaction and post-treatment were performed in accordance with Reference Example 1-(f) except for using 1.35 g (4.00 mmol) of tert-butyl [(6-aminomethylpyridin-2-yl)tert-butoxycarbonylamino]acetate obtained in the same manner as in Reference Example 1-(e), and using 707 mg (4.00 mmol) of benzenesulfonyl chloride in place of 2-pyridylsulfonyl chloride, to afford 1.71 g of the title compound as a slightly beige solid. (Yield: 89%)

Mass spectrum (CI, m/z): 478 ($M^+ +1$)

$^1$H-NMR spectrum (CDCl$_3$, δ ppm): 7.86-7.83 (m, 2H), 7.67 (d, J=8.4 Hz, 1H), 7.53-7.48 (m, 2H), 7.45-7.41 (m, 2H), 6.78 (dd, J=7.4, 0.6 Hz, 1H), 5.56 (t, J=5.4 Hz, 1H), 4.41 (s, 2H), 4.19 (d, J=5.4 Hz, 2H), 1.53 (s, 9H), 1.46 (s, 9H)

10-(b): Ethyl {6-[(benzenesulfonyl)aminomethyl]pyridin-2-ylamino}acetate

The reaction and post-treatment were performed in accordance with Reference Example 9-(b) except for using 1.70 g (3.56 mmol) of tert-butyl ({6-[(benzenesulfonyl)aminomethyl]pyridin-2-yl}tert-butoxycarbonylamino)acetate obtained in Reference Example 10-(a) in place of tert-butyl (tert-butoxycarbonyl{6-[(thiophen-2-ylsulfonyl)aminomethyl]pyridin-2-yl}amino)acetate, and using 20 mL (40 mmol) of 2 mol/L hydrogen chloride/ethanol solution, to afford 1.13 g of the title compound as a white solid. (Yield: 91%)

Mass spectrum (CI, m/z): 350 ($M^+ +1$)

$^1$H-NMR spectrum (CDCl$_3$, δ ppm): 7.87-7.84 (m, 2H), 7.53-7.42 (m, 3H), 7.28 (dd, J=8.3, 7.3 Hz, 1H), 6.39 (dd, J=7.3, 0.6 Hz, 1H), 6.30 (dd, J=8.3, 0.6 Hz, 1H), 5.73 (t, J=4.9 Hz, 1H), 4.92 (t, J=5.2 Hz, 1H), 4.26 (q, J=7.2 Hz, 2H), 4.09 (d, J=4.9 Hz, 2H), 4.04 (d, J=5.2 Hz, 2H), 1.32 (t, J=7.2 Hz, 3H)

Reference Example 11

Ethyl {6-[(thiophen-3-ylsulfonyl)aminomethyl]pyridin-2-ylamino}acetate 11-(a): tert-Butyl (tert-butoxycarbonyl {6-[(thiophen-3-ylsulfonyl)-aminomethyl]pyridin-2-yl}amino)acetate The reaction and post-treatment were performed in accordance with Reference Example 1-(f) except for using 1.35 g (4.00 mmol) of tert-butyl [(6-aminomethylpyridin-2-yl)tert-butoxycarbonylamino]acetate obtained in the same manner as in Reference Example 1-(e), and using 731 mg (4.00 mmol) of 3-thiophenesulfonyl chloride in place of 2-pyridylsulfonyl chloride, to afford 1.64 g of the title compound as a pale yellowish white solid. (Yield: 85%)

Mass spectrum (CI, m/z): 484 ($M^+ +1$)

$^1$H-NMR spectrum (CDCl$_3$, δ ppm): 7.93 (dd, J=2.9, 1.4 Hz, 1H), 7.69 (d, J=8.3 Hz, 1H), 7.54 (dd, J=8.3, 7.4 Hz, 1H), 7.30 (dd, J=5.1, 2.9 Hz, 1H), 7.28 (dd, J=5.1, 1.4 Hz, 1H), 6.80 (dd, J=7.4, 0.6 Hz, Hi), 5.59 (t, J=5.4 Hz, 1H), 4.43 (s, 2H), 4.23 (d, J=5.4 Hz, 2H), 1.53 (s, 9H), 1.47 (s, 9H)

11-(b): Ethyl {6-[(thiophen-3-ylsulfonyl)aminomethyl]pyridin-2-ylamino}acetate

The reaction and post-treatment were performed in accordance with Reference Example 9-(b) except for using 1.63 g (3.37 mmol) of tert-butyl (tert-butoxycarbonyl {6-[(thiophen-3-ylsulfonyl)aminomethyl]pyridin-2-yl}amino)acetate obtained in Reference Example 11-(a) in place of tert-butyl (tert-butoxycarbonyl{6-[(thiophen-2-ylsulfonyl)aminomethyl]pyridin-2-yl}amino)acetate, and using 17.5 mL (35.0 mmol) of 2 mol/L hydrogen chloride/ethanol solution. The residue was subjected to silica gel column chromatography (elution solvent; n-hexane:ethyl acetate=7:3→1:1 (V/V)), and fractions containing the target product were concentrated under reduced pressure. The obtained crude material was recrystallized from 5 mL of ethyl acetate to afford 731 mg of the title compound as a white solid. (Yield: 61%)

Mass spectrum (CI, m/z): 356 (M$^+$+1)

$^1$H-NMR spectrum (CDCl$_3$, δ ppm): 7.93 (dd, J=3.0, 1.4 Hz, 1H), 7.33-7.28 (m, 3H), 6.40 (dd, J=7.3, 0.6 Hz, 1H), 6.32 (dd, J=8.3, 0.6 Hz, 1H), 5.76 (t, J=5.1 Hz, 1H), 4.95 (t, J=5.4 Hz, 1H), 4.27 (q, J=7.2 Hz, 2H), 4.13 (d, J=5.1 Hz, 2H), 4.06 (d, J=5.4 Hz, 2H), 1.32 (t, =7.2 Hz, 3H)

Reference Example 12 tert-Butyl [tert-butoxycarbonyl(6-{[3'-(1-propynyl)biphenyl-4-ylmethyl]-aminomethyl}pyridin-2-yl)amino]acetate 12-(a): 1-Bromo-3-(1-propynyl)benzene To a solution of 7.07 g (25.0 mmol) of 1-bromo-3-iodobenzene in 50 mL of toluene were added 1.43 g (7.51 mmol) of copper(I) iodide and 1.45 g (1.25 mmol) of tetrakis(triphenylphosphine)palladium, degassed under reduced pressure, and then substituted with argon gas. Thereafter, 2.81 g (25.0 mmol) of 1-trimethylsilyl-1-propyne, 11.5 mL (82.5 mmol) of triethylamine, and 25.0 mL (25.0 mmol) of 1 mol/L tetrafluoroammonium fluoride/tetrahydrofuran solution were added and stirred for 17 hours at room temperature in an argon gas atmosphere. After the completion of the reaction, water and t-butyl methyl ether were added to the reaction solution, and insoluble substances were filtered off through Celite (trade name). The organic layer after separation was dried over anhydrous magnesium sulfate and concentrated under reduced pressure. The residue was subjected to silica gel column chromatography (elution solvent; n-hexane), and fractions containing the target product were concentrated under reduced pressure to afford 4.22 g of the title compound as a colorless oil. (Yield: 86%)

Mass spectrum (CI, m/z): 195, 197 (M$^+$+1)

$^1$H-NMR spectrum (CDCl$_3$, δ ppm): 7.53 (dd, J=1.7, 1.7 Hz, 1H), 7.39 (ddd, J=8.0, 1.7, 1.0 Hz, 1H), 7.31-7.29 (m, 1H), 7.14 (dd, J=8.0, 8.0 Hz, 1H), 2.04 (s, 3H)

12-(b): 3'(1-Propynyl)biphenyl-4-ylcarbaldehyde

The reaction and post-treatment were performed in accordance with Reference Example 5 except for using 2.93 g (15.0 mmol) of 1-bromo-3-(1-propynyl)benzene obtained in the same manner as in Reference Example 12-(a) in place of 3-bromophenetole, using 3.37 g (37.5 mmol) of 4-formylphenylboronic acid in place of 4-(hydroxymethyl)phenylboronic acid, and using 11.3 mL (22.6 mmol) of 2 mol/L aqueous sodium carbonate solution and 867 mg (0.750 mmol) of tetrakis(triphenylphosphine)palladium, to afford 3.31 g of the title compound as a pale yellowish white solid. (Quantitative)

The NMR spectrum for the compound obtained in this Reference Example 12-(b) was identical to the NMR spectrum for the compound obtained in Reference Example 4-(a).

12-(c): tert-Butyl [tert-butoxycarbonyl(6-{[3'-(1-propynyl)biphenyl-4-ylmethyl]aminomethyl}pyridin-2-yl)amino]acetate The reaction and post-treatment were performed in accordance with Reference Example 7-(b) except for using 5.57 g (16.5 mmol) of tert-butyl [(6-aminomethylpyridin-2-yl)tert-butoxycarbonylamino]acetate obtained in the same manner as in Reference Example 1-(e), using 3.30 g (15.0 mmol) of 3'-(1-propynyl)biphenyl-4-ylcarbaldehyde obtained in Reference Example 12-(b) in place of 3'-ethoxybiphenyl-4-ylcarbaldehyde, and using 4.45 g (21.0 mmol) of sodium triacetoxyborohydride, to afford 6.48 g of the title compound as a pale yellow oil. (Yield: 80%)

Mass spectrum (CI, m/z): 542 (M$^+$+1)

$^1$H-NMR spectrum (CDCl$_3$, δ ppm): 7.70 (d, J=8.2 Hz, 1H), 7.63-7.62 (m, 1H), 7.59 (dd, J=8.2, 7.4 Hz, 1H), 7.55-7.52 (m, 2H), 7.50-7.47 (m, 1H), 7.43-7.40 (m, 2H), 7.37-7.32 (m, 2H), 6.97 (d, J=7.4 Hz, 1H), 4.57 (s, 2H), 3.85 (s, 2H), 3.83 (s, 2H), 2.07 (s, 3H), 1.53 (s, 9H), 1.41 (s, 9H)

Reference Example 13

3'-(1-Propynyl)biphenyl-4-ylmethanol

The reaction was performed in accordance with Reference Example 5 except for using 3.90 g (20.0 mmol) of 1-bromo-3-(1-propynyl)benzene obtained in the same manner as in Reference Example 12-(a) in place of 3-bromophenetole, and using 4.56 g (30.0 mmol) of 4-(hydroxymethyl)phenylboronic acid, 15 mL (30 mmol) of 2 mol/L aqueous sodium carbonate solution, and 1.16 g (1.00 mmol) of tetrakis (triphenylphosphine)palladium. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=4:1→1:1 (V/V)), and fractions containing the target product were concentrated under reduced pressure. The obtained crude material was stirred in 45 mL of mixed solvent (ethyl acetate:n-hexane=1:10 (V/V)) for 1 hour. The precipitated solid was collected by filtration and then dried under reduced pressure to afford 3.85 g of the title compound as a white solid. (Yield: 87%)

The NMR spectrum for the compound obtained in this Reference Example 13 was identical to the NMR spectrum for the compound obtained in Reference Example 4-(b).

Reference Example 14

Isopropyl {6-[(pyridin-2-ylsulfonyl)aminomethyl]pyridin-2-ylamino}acetate

The reaction and post-treatment were performed in accordance with Reference Example 9-(b) except for using 1.44 g (3.01 mmol) of tert-butyl (tert-butoxycarbonyl {6-[(pyridin-2-ylsulfonyl)aminomethyl]pyridin-2-yl}amino)acetate obtained in the same manner as in Reference Example 1-(f) in place of tert-butyl (tert-butoxycarbonyl {6-[(thiophen-2-ylsulfonyl)aminomethyl]pyridin-2-yl}amino)acetate, and using 16.0 mL (32.0 mmol) of 2 mol/L hydrogen chloride/isopropanol solution in place of 2 mol/L hydrogen chloride/ethanol solution, to afford 1.05 g of the title compound as a white solid. (Yield: 96%)

Mass spectrum (CI, m/z): 365 ($M^++1$)

$^1$H-NMR spectrum (CDCl$_3$, δ ppm): 8.63 (ddd, J=4.7, 1.7, 1.0 Hz, 1H), 7.97 (ddd, J=7.7, 1.0, 1.0 Hz, 1H), 7.84 (ddd, J=7.7, 7.7, 1.7 Hz, 1H), 7.41 (ddd, J=7.7, 4.7, 1.0 Hz, 1H), 7.29 (dd, J=8.2, 7.3 Hz, 1H), 6.44 (d, J=7.3 Hz, 1H), 6.28 (d, J=8.2 Hz, 1H), 6.04 (t, J=5.4 Hz, 1H), 5.10 (sep, J=6.3 Hz, 1H), 4.93 (t, J=5.4 Hz, 1H), 4.25 (d, J=5.4 Hz, 2H), 4.04 (d, J=5.4 Hz, 2H), 1.28 (d, J=6.3 Hz, 6H)

Comparative Example 1

{6-[(Biphenyl-4-ylmethyl)(pyridin-2-ylsulfonyl)aminomethyl]pyridin-2-ylamino}acetic acid This compound is the compound described in Example 17 of WO2009/113600 (Example Number 538).

Comparative Example 2

{6-[(Biphenyl-4-ylmethyl)(pyridin-3-ylsulfonyl)aminomethyl]pyridin-2-ylamino}acetic acid This compound is the compound described in Example 6 of WO2009/113600 (Example Number 546).

Comparative Example 3

{6-[(4'-Fluorobiphenyl-4-ylmethyl)(pyridin-3-ylsulfonyl)aminomethyl]-pyridin-2-ylamino}acetic acid This compound is the compound described in Example 9 of WO2009/113600 (Example Number 605).

Comparative Example 4

{6-[(4'-Chlorobiphenyl-4-ylmethyl)(pyridin-3-ylsulfonyl)aminomethyl]-pyridin-2-ylamino}acetic acid This compound is the compound described in Example 10 of WO2009/113600 (Example Number 681).

Comparative Example 5

(6-{[4-(5-Methylthiazol-2-yl)benzyl](pyridin-2-ylsulfonyl)aminomethyl}-pyridin-2-ylamino)acetic acid This compound is the compound described in Example 22 of WO2009/113600 (Example Number 1446).

Comparative Example 6

{6-[(3'-Methylbiphenyl-4-ylmethyl)(pyridin-2-ylsulfonyl)aminomethyl]-pyridin-2-ylamino}acetic acid This compound is the compound of Example Number 740 described in WO2009/113600.

6-(a): 3'-Methylbiphenyl-4-ylmethanol

The reaction and post-treatment were performed in accordance with Reference Example 5 except for using 1.71 g (10.0 mmol) of 3-bromotoluene in place of 3-bromophenetole, and using 2.28 g (15.0 mmol) of 4-(hydroxymethyl)phenylboronic acid, 7.5 mL (15 mmol) of 2 mol/L aqueous sodium carbonate solution, and 580 mg (0.500 mmol) of tetrakis(triphenylphosphine)palladium, to afford 1.74 g of the title compound as a pale white yellow solid. (Yield: 88%)

Mass spectrum (EI, m/z): 198 ($M^+$)

$^1$H-NMR spectrum (CDCl$_3$, δ ppm): 7.60-7.57 (m, 2H), 7.45-7.38 (m, 4H), 7.35-7.31 (m, 1H), 7.18-7.15 (m, 1H), 4.74 (d, J=6.0 Hz, 2H), 2.42 (s, 3H), 1.66 (t, J=6.0 Hz, 1H)

6-(b): tert-Butyl (tert-butoxycarbonyl{6-[(3'-methylbiphenyl-4-ylmethyl)-(pyridin-2-ylsulfonyl)aminomethyl]pyridin-2-yl}amino)acetate The reaction and post-treatment were performed in accordance with Example 1 except for using 403 mg (0.841 mmol) of tert-butyl (tert-butoxycarbonyl {6-[(pyridin-2-ylsulfonyl)aminomethyl]pyridin-2-yl}amino)acetate obtained in the same manner as in Reference Example 1-(f) and 159 mg (0.800 mmol) of 3'-methylbiphenyl-4-ylmethanol obtained in Comparative Example 6-(a) in place of 3'-(1-propenyl)biphenyl-4-ylmethanol, and using 395 μL (1.60 mmol) of tri-n-butylphosphine and 277 mg (1.60 mmol) of N,N,N',N'-tetramethylazodicarboxamide, to afford 480 mg of the title compound as a white foam. (Yield: 91%)

Mass spectrum (ESI$^+$, m/z): 659 ($M^++1$)

$^1$H-NMR spectrum (CDCl$_3$, δ ppm): 8.60 (ddd, J=4.8, 1.7, 0.9 Hz, 1H), 7.82 (ddd, J=7.7, 1.2, 0.9 Hz, 1H), 7.77 (ddd, J=7.7, 7.6, 1.7 Hz, 1H), 7.65 (d, J=7.8 Hz, 1H), 7.47-7.42 (m, 3H), 7.38 (ddd, J=7.6, 4.8, 1.2 Hz, 1H), 7.35-7.27 (m, 5H), 7.17-7.14 (m, 1H), 6.92 (d, J=7.4 Hz, 1H), 4.74 (s, 2H), 4.51 (s, 2H), 4.46 (s, 2H), 2.42 (s, 3H), 1.52 (s, 9H), 1.43 (s, 9H)

6-(c): {6-[(3'-Methylbiphenyl-4-ylmethyl)(pyridin-2-ylsulfonyl)-aminomethyl]pyridin-2-ylamino}acetic acid To a solution of 477 mg (0.724 mmol) of tert-butyl (tert-butoxycarbonyl {6-[(3'-methylbiphenyl-4-ylmethyl)(pyridin-2-ylsulfonyl)-aminomethyl]pyridin-2-yl}amino)acetate obtained in Comparative Example 6-(b) in 10 mL of methylene chloride, 2.8 mL (37 mmol) of trifluoroacetic acid was added at room temperature and stirred for 16 hours. After the completion of the reaction, the reaction solution was concentrated under reduced pressure. Thereafter, water was added to the reaction solution, and pH of the solution was adjusted to 4.5 with 1 mol/L aqueous sodium hydroxide solution, followed by extraction with ethyl acetate. The organic layer was dried over anhydrous sodium sulfate, and then concentrated under reduced pressure. The residue was subjected to silica gel column chromatography (elution solvent; ethyl acetate:methanol=1:0→3:1 (V/V)), and fractions containing the target product were concentrated under reduced pressure to afford 364 mg of the title compound as a white foam. (Quantitative)

Mass spectrum (ESI$^+$, m/z): 503 ($M^++1$)

$^1$H-NMR spectrum (DMSO-d$_6$, δ ppm): 12.41 (brs, 0.9H), 8.64 (ddd, J=4.7, 1.7, 1.0 Hz, 1H), 7.95 (ddd, J=7.7, 7.7, 1.7 Hz, 1H), 7.82-7.79 (m, 1H), 7.60-7.53 (m, 3H), 7.45-7.41 (m, 2H), 7.36-7.30 (m, 3H), 7.23-7.17 (m, 2H), 6.78 (brs, 1H), 6.35 (d, J=8.2 Hz, 1H), 6.30 (d, J=7.0 Hz, 1H), 4.73 (s, 2H), 4.25 (s, 2H), 3.84 (s, 2H), 2.38 (s, 3H)

Comparative Example 7

{6-[(3'-Ethylbiphenyl-4-ylmethyl)(pyridin-2-ylsulfonyl)aminomethyl]pyridin-2-ylamino}acetic acid This compound is the compound of Example Number 751 described in WO2009/113600.

7-(a): 3'-Ethylbiphenyl-4-ylcarbaldehyde

To a solution of 380 mg (1.43 mmol) of 3'-bromobiphenyl-4-ylcarbaldehyde in 21 mL of toluene were added 1.2 mL of water, 1.22 g (5.75 mmol) of tripotassium phosphate, and 423 mg (5.72 mmol) of ethyl boronic acid, degassed under reduced pressure, and then substituted with nitrogen gas. Thereafter, 4.6 mg (0.020 mmol) of palladium acetate and 15.1 mg (0.0421 mmol) of butyl-di-1-adamantylphosphine were added and stirred for 3 hours at 100° C. in a nitrogen gas atmosphere. The post-treatment after the completion of the reaction was performed in accordance with Reference Example 5 to substantially quantitatively afford 325 mg of the title compound as a brown oil.

$^1$H-NMR spectrum (CDCl$_3$, δ ppm): 10.06 (s, 1H), 7.99-7.91 (m, 2H), 7.79-7.72 (m, 2H), 7.49-7.35 (m, 3H), 7.29-7.22 (m, 1H), 2.74 (q, J=7.6 Hz, 2H), 1.30 (t, J=7.6 Hz, 3H)

7-(b): 3'-Ethylbiphenyl-4-ylmethanol

The reaction and post-treatment were performed in accordance with Reference Example 3-(b) except for using 320 mg (equivalent to 1.43 mmol of pure content) of 3'-ethylbiphenyl-4-ylcarbaldehyde obtained in Comparative Example 7-(a) in place of 3'-(1-propenyl)biphenyl-4-ylcarbaldehyde, and using 28.7 mg (0.759 mmol) of sodium borohydride, to substantially quantitatively afford 317 mg of the title compound as a colorless oil.

$^1$H-NMR spectrum (CDCl$_3$, δ ppm): 7.63-7.56 (m, 2H), 7.49-7.31 (m, 5H), 7.23-7.16 (m, 1H), 4.74 (s, 2H), 2.72 (q, J=7.6 Hz, 2H), 1.70 (brs, 0.8H), 1.29 (t, J=7.6 Hz, 3H)

7-(c): tert-Butyl (tert-butoxycarbonyl{6-[(3'-ethylbiphenyl-4-ylmethyl)-(pyridin-2-ylsulfonyl)aminomethyl]pyridin-2-yl}amino)acetate The reaction and post-treatment were performed in accordance with Example 1 except for using 200 mg (0.418 mmol) of tert-butyl (tert-butoxycarbonyl{6-[(pyridin-2-ylsulfonyl)aminomethyl]pyridin-2-yl}amino)acetate obtained in the same manner as in Reference Example 1-(f) and 88.7 mg (0.418 mmol) of 3'-ethylbiphenyl-4-ylmethanol obtained in Comparative Example 7-(b) in place of 3'-(1-propenyl)biphenyl-4-ylmethanol, and using 198 μL (0.802 mmol) of tri-n-butylphosphine and 113 mg (0.656 mmol) of N,N,N',N'-tetramethylazodicarboxamide, to afford 253 mg of the title compound as a white syrup. (Yield: 90%)

Mass spectrum (FAB, m/z): 673 (M$^+$+1)

$^1$H-NMR spectrum (DMSO-d$_6$, δ ppm): 8.63-8.58 (m, 1H), 7.85-7.73 (m, 2H), 7.65 (d, J=8.5 Hz, 1H), 7.50-7.25 (m, 9H), 7.22-7.15 (m, 1H), 6.92 (d, J=7.3 Hz, 1H), 4.74 (s, 2H), 4.52 (s, 2H), 4.46 (s, 2H), 2.72 (q, J=7.7 Hz, 2H), 1.52 (s, 9H), 1.43 (s, 9H), 1.29 (t, J=7.7 Hz, 3H)

7-(d): {6-[(3'-Ethylbiphenyl-4-ylmethyl)(pyridin-2-ylsulfonyl)-aminomethyl]pyridin-2-ylamino}acetic acid To a solution of 243 mg (0.361 mmol) of tert-butyl (tert-butoxycarbonyl {6-[(3'-ethylbiphenyl-4-ylmethyl)(pyridin-2-ylsulfonyl)-aminomethyl]pyridin-2-yl}amino) acetate obtained in Comparative Example 7-(c) in 3.6 mL of methylene chloride, 3.6 mL (47 mmol) of trifluoroacetic acid was added at room temperature and stirred at room temperature for 2.5 hours. After the completion of the reaction, the reaction solution was concentrated under reduced pressure. Thereafter, water was added to the reaction solution, and pH of the solution was adjusted to 4.5 with 1 mol/L aqueous sodium hydroxide solution and 1 mol/L hydrochloric acid. The precipitated solid was collected by filtration, washed with water, and then concentrated under reduced pressure to afford 158 mg of the title compound as a white solid. (Yield: 85%)

Mass spectrum (FAB, m/z): 517 (M$^+$+1)

$^1$H-NMR spectrum (DMSO-d$_6$, δ ppm): 12.41 (brs, 0.8H), 8.67-8.61 (m, 1H), 7.98-7.92 (m, 1H), 7.83-7.78 (m, 1H), 7.60-7.56 (m, 1H), 7.57-7.54 (m, 2H), 7.47-7.42 (m, 2H), 7.38-7.34 (m, 1H), 7.34-7.30 (m, 2H), 7.24-7.18 (m, 2H), 6.77 (brs, 0.8H), 6.36 (d, J=8.1 Hz, 1H), 6.30 (d, J=7.0 Hz, 1H), 4.73 (s, 2H), 4.25 (s, 2H), 3.84 (s, 2H), 2.67 (q, J=7.7 Hz, 2H), 1.23 (t, J=7.7 Hz, 3H)

Comparative Example 8

{6-[(3'-Propylbiphenyl-4-ylmethyl)(pyridin-2-ylsulfonyl)aminomethyl]-pyridin-2-ylamino}acetic acid This compound is the compound of Example Number 754 described in WO2009/113600.

8-(a): 3'-Propylbiphenyl-4-ylcarbaldehyde

To a solution of 500 mg (1.91 mmol) of 3'-bromobiphenyl-4-ylcarbaldehyde in 28 mL of toluene were added 1.7 mL of water, 1.63 g (7.68 mmol) of tripotassium phosphate, and 675 mg (7.68 mmol) of propylboronic acid, degassed under reduced pressure, and then substituted with nitrogen gas. Thereafter, 6.2 mg (0.028 mmol) of palladium acetate and 20.2 mg (0.0563 mmol) of butyl-di-1-adamantylphosphine were added and stirred for 3 hours at 100° C. in a nitrogen gas atmosphere. The post-treatment after the completion of the reaction was performed in accordance with Reference Example 5 to afford 406 mg of the title compound as a pale yellow oil. (Yield: 86%)

Mass spectrum (EI, m/z): 224 (M$^+$)

$^1$H-NMR spectrum (CDCl$_3$, δ ppm): 10.06 (s, 1H), 7.99-7.91 (m, 2H), 7.78-7.73 (m, 2H), 7.51-7.34 (m, 3H), 7.28-7.20 (m, 1H), 2.73-2.61 (m, 2H), 1.80-1.62 (m, 2H), 0.98 (t, J=7.3 Hz, 3H)

8-(b): 3'-Propylbiphenyl-4-ylmethanol

The reaction and post-treatment were performed in accordance with Reference Example 3-(b) except for using 400 mg (1.78 mmol) of 3'-propylbiphenyl-4-ylcarbaldehyde obtained in Comparative Example 8-(a) in place of 3'-(1-propenyl)biphenyl-4-ylcarbaldehyde, and using 33.7 mg (0.891 mmol) of sodium borohydride, to afford 383 mg of the title compound as a white solid. (Yield: 95%)

Mass spectrum (EI, m/z): 226 (M⁺)

¹H-NMR spectrum (CDCl₃, δ ppm): 7.64-7.55 (m, 2H), 7.48-7.30 (m, 5H), 7.21-7.13 (m, 1H), 4.74 (d, J=5.6 Hz, 2H), 2.71-2.59 (m, 2H), 1.77-1.62 (m, 3H), 0.97 (t, J=7.3 Hz, 3H)

8-(c): tert-Butyl (tert-butoxycarbonyl{6-[(3'-propyl-biphenyl-4-ylmethyl)-(pyridin-2-ylsulfonyl)aminomethyl]pyridin-2-yl}amino)acetate The reaction and post-treatment were performed in accordance with Example 1 except for using 200 mg (0.418 mmol) of tert-butyl (tert-butoxycarbonyl {6-[(pyridin-2-ylsulfonyl)aminomethyl]pyridin-2-yl}amino)acetate obtained in the same manner as in Reference Example 1-(f) and 94.6 mg (0.418 mmol) of 3'-propylbiphenyl-4-ylmethanol obtained in Comparative Example 8-(b) in place of 3'-(1-propenyl)biphenyl-4-ylmethanol, and using 198 pt (0.802 mmol) of tri-n-butylphosphine and 113 mg (0.656 mmol) of N,N,N',N'-tetramethylazodicarboxamide, to afford 255 mg of the title compound. (Yield: 89%)

Mass spectrum (FAB, m/z): 687 (M⁺+1)

¹H-NMR spectrum (CDCl₃, δ ppm): 8.62-8.58 (m, 1H), 7.85-7.73 (m, 2H), 7.65 (d, J=8.3 Hz, 1H), 7.49-7.23 (m, 9H), 7.20-7.12 (m, 1H), 6.92 (d, J=7.3 Hz, 1H), 4.73 (s, 2H), 4.52 (s, 2H), 4.46 (s, 2H), 2.69-2.61 (m, 2H), 1.77-1.61 (m, 2H), 1.52 (s, 9H), 1.42 (s, 9H), 0.98 (t, J=7.3 Hz, 3H)

8-(d): {6-[(3'-Propylbiphenyl-4-ylmethyl)(pyridin-2-ylsulfonyl)aminomethyl]-pyridin-2-ylamino}acetic acid The reaction and post-treatment were performed in accordance with Comparative Example 7-(d) except for using 247 mg (0.360 mmol) of tert-butyl (tert-butoxycarbonyl {6-[(3-propylbiphenyl-4-ylmethyl)(pyridin-2-ylsulfonyl)-aminomethyl]pyridin-2-yl}amino)acetate obtained in Comparative Example 8-(c) in place of tert-butyl (tert-butoxycarbonyl {6-[(3'-ethylbiphenyl-4-ylmethyl)-(pyridin-2-ylsulfonyl)aminomethyl]pyridin-2-yl}amino)acetate, and using 0.74 mL (9.7 mmol) of trifluoroacetic acid, to afford 161 mg of the title compound as a white solid. (Yield: 84%)

Mass spectrum (FAB, m/z): 531 (M⁺+1)

¹H-NMR spectrum (DMSO-d₆, δ ppm): 12.42 (brs, 0.8H), 8.66-8.63 (m, 1H), 7.95 (ddd, J=7.7, 7.6, 1.5 Hz, 1H), 7.83-7.79 (m, 1H), 7.58 (ddd, J=7.6, 4.7, 0.8 Hz, 1H), 7.57-7.53 (m, 2H), 7.46-7.41 (m, 2H), 7.38-7.34 (m, 1H), 7.33-7.30 (m, 2H), 7.25-7.16 (m, 2H), 6.78 (brs, 0.8H), 6.36 (d, J=8.1 Hz, 1H), 6.30 (d, J=7.0 Hz, 1H), 4.73 (s, 2H), 4.26 (s, 2H), 3.84 (s, 2H), 2.65-2.60 (m, 2H), 1.68-1.60 (m, 2H), 0.92 (t, J=7.3 Hz, 3H)

Comparative Example 9

(6-{[3'-(1-Butenyl)biphenyl-4-ylmethyl](pyridin-2-ylsulfonyl)aminomethyl}-pyridin-2-ylamino)acetic acid 9-(a): 3'(1-Butenyl)biphenyl-4-ylcarbaldehyde The reaction and post-treatment were performed in accordance with Reference Example 5 except for using 445 mg (2.11 mmol) of 1-bromo-3-(1-butenyl)benzene (see WO2008/124848) in place of 3-bromophenetole, using 497 mg (3.31 mmol) of 4-formylphenylboronic acid in place of 4-(hydroxymethyl)phenylboronic acid, and using 1.5 mL (3.0 mmol) of 2 mol/L aqueous sodium carbonate solution and 120 mg (0.104 mmol) of tetrakis(triphenylphosphine) palladium, to afford 489 mg of the title compound as a colorless oil. (Yield: 98%)

Mass spectrum (CI, m/z): 237 (M⁺+1)

¹H-NMR spectrum (CDCl₃, δ ppm): 10.06 (s, 1H), 8.00-7.92 (m, 2H), 7.80-7.73 (m, 2H), 7.61-7.57 (m, 1H), 7.53-7.37 (m, 3H), 6.50-6.30 (m, 2H), 2.33-2.21 (m, 2H), 1.12 (t, J=7.4 Hz, 3H)

9-(b): 3'-(1-Butenyl)biphenyl-4-ylmethanol

The reaction and post-treatment were performed in accordance with Reference Example 3-(b) except for using 480 mg (2.03 mmol) of 3'-(1-butenyl)biphenyl-4-ylcarbaldehyde obtained in Comparative Example 9-(a) in place of 3'-(1-propenyl)biphenyl-4-ylcarbaldehyde, and using 38.5 mg (1.02 mmol) of sodium borohydride, to afford 465 mg of the title compound as a white solid. (Yield: 96%)

Mass spectrum (EI, m/z): 238 (M⁺)

¹H-NMR spectrum (CDCl₃, δ ppm): 7.64-7.57 (m, 2H), 7.57-7.54 (m, 1H), 7.48-7.30 (m, 5H), 6.50-6.26 (m, 2H), 4.75 (d, J=5.9 Hz, 2H), 2.33-2.19 (m, 2H), 1.66 (t, J=5.9 Hz, 1H), 1.11 (t, J=7.4 Hz, 3H)

9-(c): Ethyl (6-{[3'-(1-butenyl)biphenyl-4-ylmethyl](pyridin-2-ylsulfonyl)-aminomethyl}pyridin-2-ylamino)acetate The reaction and post-treatment were performed in accordance with Example 1 except for using 200 mg (0.571 mmol) of ethyl {6-[(pyridin-2-ylsulfonyl)aminomethyl]pyridin-2-ylamino}acetate obtained in the same manner as in Reference Example 1-(g) and 136 mg (0.571 mmol) of 3'-(1-butenyl)biphenyl-4-ylmethanol obtained in Comparative Example 9-(b) in place of 3'-(1-propenyl)biphenyl-4-ylmethanol, and using 270 µL (1.09 mmol) of tri-n-butylphosphine and 154 mg (0.894 mmol) of N,N,N',N'-tetramethylazodicarboxamide, to afford 188 mg of the title compound as a colorless oil. (Yield: 58%)

¹H-NMR spectrum (CDCl₃, δ ppm): 8.62 (ddd, J=4.6, 1.7, 0.9 Hz, 1H), 7.83 (ddd, J=7.7, 1.0, 0.9 Hz, 1H), 7.75 (ddd, J=7.7, 7.6, 1.7 Hz, 1H), 7.53-7.50 (m, 1H), 7.50-7.45 (m, 2H), 7.40-7.32 (m, 6H), 7.23 (dd, J=8.3, 7.3 Hz, 1H), 6.51 (d, J=7.3 Hz, 1H), 6.49-6.27 (m, 2H), 6.23 (d, J=8.3 Hz, 1H), 4.80 (s, 2H), 4.70 (t, J=5.4 Hz, 1H), 4.42 (s, 2H), 4.22 (q, J=7.1 Hz, 2H), 3.96 (d, J=5.4 Hz, 2H), 2.32-2.20 (m, 2H), 1.28 (t, J=7.1 Hz, 3H), 1.11 (t, J=7.4 Hz, 3H)

9-(d): (6-{[3'-(1-Butenyl)biphenyl-4-ylmethyl](pyridin-2-ylsulfonyl)-aminomethyl}pyridin-2-ylamino) acetic acid The reaction and post-treatment were performed in accordance with Example 2 except for using 180 mg (0.315 mmol) of ethyl (6-{[3'-(1-butenyl)biphenyl-4-ylmethyl](pyridin-2-ylsulfonyl)aminomethyl}pyridin-2-ylamino)acetate obtained in Comparative Example 9-(c) in place of ethyl (6-{[3'-(1-propenyl)biphenyl-4-ylmethyl](pyridin-2-ylsulfonyl)aminomethylpyridin-2-yl}amino)acetate, and using 1.58 mL (1.58 mmol) of 1 mol/L aqueous sodium hydroxide solution, to afford 134 mg of the title compound as a white solid. (Yield: 78%)

Mass spectrum (FAB, m/z): 543 (M⁺+1)

¹H-NMR spectrum (DMSO-d₆, δ ppm): 12.52 (brs, 0.6H), 8.69-8.65 (m, 1H), 8.03-7.95 (m, 1H), 7.89-7.81 (m, 1H), 7.65-7.53 (m, 4H), 7.46-7.43 (m, 1H), 7.40-7.38 (m, 2H), 7.36-7.22 (m, 3H), 6.60-6.21 (m, 4H), 4.70 (s, 2H), 4.33 (s, 2H), 3.89 (s, 2H), 2.26-2.20 (m, 2H), 1.08 (t, J=7.5 Hz, 3H)

Comparative Example 10

(6-{[3'-(2-Propenyl)biphenyl-4-ylmethyl](pyridin-2-ylsulfonyl)aminomethyl}-pyridin-2-ylamino)acetic acid 10-(a): 3'-(2-Propenyl)biphenyl-4-ylmethanol To a mixed solution of 2.11 g (8.00 mmol) of 3'-bromobiphenyl-4-ylmethanol (see WO2001/070753) in 80 mL of toluene/ethanol=1:1 (V/V) were added 8.0 mL (16 mmol) of 2 mol/L aqueous sodium carbonate solution and 2.24 mL (12.0 mmol) of allylboronic acid pinacol ester, degassed under reduced pressure, and then substituted with argon gas. Thereafter, 462 mg (0.400 mmol) of tetrakis(triphenylphosphine)palladium was added and stirred for 9 hours at 100° C. in an argon gas atmosphere. Furthermore, 1.50 mL (8.00 mmol) of allylboronic acid pinacol ester and 925 mg (0.800 mmol) of tetrakis(triphenylphosphine)palladium were added and stirred for 5 hours at the same temperature. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The residue was subjected to silica gel column chromatography (elution solvent; n-hexane:ethyl acetate=4:1→3:2 (V/V)), and fractions containing the target product were concentrated under reduced pressure to afford 1.11 g of the title compound as a pale brown solid. (Yield: 62%)

Mass spectrum (EI, m/z): 224 (M$^+$)

$^1$H-NMR spectrum (CDCl$_3$, δ ppm): 7.61-7.57 (m, 2H), 7.45-7.34 (m, 5H), 7.20-7.17 (m, 1H), 6.08-5.95 (m, 1H), 5.17-5.07 (m, 2H), 4.74 (d, J=4.4 Hz, 2H), 3.46 (d, J=6.8 Hz, 2H), 1.66 (t, J=4.4 Hz, 1H)

10-(b): Ethyl (6-{[3'-(2-propenyl)biphenyl-4-ylmethyl](pyridin-2-ylsulfonyl)-aminomethyl}pyridin-2-ylamino)acetate The reaction and post-treatment were performed in accordance with Example 1 except for using 331 mg (0.945 mmol) of ethyl {6-[(pyridin-2-ylsulfonyl)aminomethyl]pyridin-2-ylamino}acetate obtained in the same manner as in Reference Example 1-(g) and 202 mg (0.900 mmol) of 3'-(2-propenyl)biphenyl-4-ylmethanol obtained in Comparative Example 10-(a) in place of 3'-(1-propenyl)biphenyl-4-ylmethanol, and using 450 μL (1.82 mmol) of tri-n-butylphosphine and 310 mg (1.80 mmol) of N,N,N',N'-tetramethylazodicarboxamide, to afford 478 mg of the title compound as a colorless oil. (Yield: 95%)

Mass spectrum (FAB, m/z): 557 (M$^+$+1)

$^1$H-NMR spectrum (CDCl$_3$, δ ppm): 8.61 (ddd, J=4.8, 1.8, 1.1 Hz, 1H), 7.82 (ddd, J=7.7, 1.3, 1.1 Hz, 1H), 7.75 (ddd, J=7.7, 7.5, 1.8 Hz, 1H), 7.48-7.44 (m, 2H), 7.42-7.33 (m, 6H), 7.23 (dd, J=8.2, 7.3 Hz, 1H), 7.20-7.16 (m, 1H), 6.51 (d, J=7.3 Hz, 1H), 6.23 (d, J=8.2 Hz, 1H), 6.08-5.95 (m, 1H), 5.17-5.15 (m, 1H), 5.13-5.08 (m, 1H), 4.80 (s, 2H), 4.69 (t, J=5.3 Hz, 1H), 4.42 (s, 2H), 4.22 (q, J=7.1 Hz, 2H), 3.96 (d, J=5.3 Hz, 2H), 3.46 (d, J=6.6 Hz, 2H), 1.28 (t, J=7.1 Hz, 3H)

10-(c): (6-{[3'-(2-Propenyl)biphenyl-4-ylmethyl](pyridin-2-ylsulfonyl)-aminomethyl}pyridin-2-ylamino)acetic acid The reaction and post-treatment were performed in accordance with Example 4 except for using 473 mg (0.849 mmol) of ethyl (6-{[3'-(2-propenyl)biphenyl-4-ylmethyl](pyridin-2-ylsulfonyl)aminomethyl}pyridin-2-ylamino)acetate obtained in Comparative Example 10-(b) in place of ethyl (6-{[3'-(1-propynyl)biphenyl-4-ylmethyl](pyridin-2-ylsulfonyl)aminomethyl}pyridin-2-ylamino)acetate, and using 3.40 mL (3.40 mmol) of 1 mol/L aqueous sodium hydroxide solution, to afford 409 mg of the title compound as a white foam. (Yield: 91%)

Mass spectrum (FAB, m/z): 529 (M$^+$+1)

$^1$H-NMR spectrum (DMSO-d$_6$, δ ppm): 12.44 (brs, 0.5H), 8.64 (ddd, J=4.8, 1.8, 1.0 Hz, 1H), 7.95 (ddd, J=7.8, 7.8, 1.8 Hz, 1H), 7.80 (ddd, J=7.8, 1.0, 1.0 Hz, 1H), 7.58 (ddd, J=7.8, 4.8, 1.0 Hz, 1H), 7.56-7.53 (m, 2H), 7.48-7.44 (m, 2H), 7.39 (dd, J=7.7, 7.7 Hz, 1H), 7.33-7.31 (m, 2H), 7.20 (dd, J=8.4, 7.2 Hz, 2H), 6.75 (t, J=5.7 Hz, 1H), 6.34 (d, J=8.4 Hz, 1H), 6.29 (d, J=7.2 Hz, 1H), 6.06-5.97 (m, 1H), 5.15-5.11 (m, 1H), 5.09-5.06 (m, 1H), 4.74 (s, 2H), 4.24 (s, 2H), 3.82 (d, J=5.7 Hz, 2H), 3.44 (d, J=7.0 Hz, 2H)

Comparative Example 11

{6-[(3'-Methoxybiphenyl-4-ylmethyl)(pyridin-2-ylsulfonyl)aminomethyl]-pyridin-2-ylamino}acetic acid This compound is the compound of Example Number 797 described in WO2009/113600.

11-(a): tert-Butyl (tert-butoxycarbonyl{6-[(4-iodobenzyl)(pyridin-2-yl-sulfonyl)aminomethyl]pyridin-2-yl}amino)acetate To a solution of 1.50 g (3.14 mmol) of tert-butyl (tert-butoxycarbonyl {6-[(pyridin-2-ylsulfonyl)aminomethyl]pyridin-2-yl}amino)acetate obtained in the same manner as in Reference Example 1-(f) in 9 mL of acetonitrile, 8.57 g (6.20 mmol) of potassium carbonate and 1.1 g (3.7 mmol) of 4-iodobenzyl bromide were added and stirred for 1 hour at room temperature and then for 1 hour at 50° C. Then, 0.47 g (1.6 mmol) of 4-iodobenzyl bromide was further added and stirred for 2 hours at 50° C. After the completion of the reaction, water was added to the reaction solution, followed by extraction with ethyl acetate. The organic layer was washed with saturated aqueous sodium chloride solution, dried over anhydrous magnesium sulfate, and then concentrated under reduced pressure. The obtained residue was subjected to silica gel column chromatography (elution solvent; n-hexane:ethyl acetate=3:1→1:1 (V/V)), and fractions containing the target product were concentrated under reduced pressure to afford 2.04 g of the title compound as a white foam. (Yield: 94%)

Mass spectrum (CI, m/z): 695 (M$^+$+1)

$^1$H-NMR spectrum (CDCl$_3$, δ ppm): 8.59 (ddd, J=4.7, 1.8, 1.0 Hz, 1H), 7.82-7.74 (m, 2H), 7.66 (d, J=8.3 Hz, 1H), 7.58-7.53 (m, 2H), 7.44 (dd, J=8.3, 7.5 Hz, 1H), 7.42-7.37 (m, 1H), 7.02-6.97 (m, 2H), 6.87 (d, J=7.5 Hz, 1H), 4.65 (s, 2H), 4.44 (s, 2H), 4.43 (s, 2H), 1.53 (s, 9H), 1.42 (s, 9H)

11-(b): tert-Butyl (tert-butoxycarbonyl {6-[(3'-methoxybiphenyl-4-ylmethyl)-(pyridin-2-ylsulfonyl)aminomethyl]pyridin-2-yl}amino)acetate The reaction and post-treatment were performed in accordance with Reference Example 5 except for using 400 mg (0.577 mmol) of tert-butyl (tert-butoxycarbonyl {6-[(4-iodobenzyl)(pyridin-2-ylsulfonyl)aminomethyl]pyridin-2-yl}amino)acetate obtained in Comparative Example 11-(a) in place of 3-bromophenetole, using 134 mg (0.879 mmol) of 3-methoxyphenylboronic acid in place of 4-(hydroxymethyl)phenylboronic acid, and using 1.3 mL (2.6 mmol) of 2 mol/L aqueous sodium carbonate solution and 67 mg (0.058 mmol) of tetrakis(triphenylphosphine)palladium, to afford 315 mg of the title compound as a white foam. (Yield: 81%)

Mass spectrum (CI, m/z): 675 ($M^+$+1)

$^1$H-NMR spectrum (CDCl$_3$, δ ppm): 8.60 (ddd, J=4.7, 1.8, 1.1 Hz, 1H), 7.82 (ddd, J=7.7, 1.1, 1.1 Hz, 1H), 7.77 (ddd, J=7.7, 7.7, 1.8 Hz, 1H), 7.65 (d, J=8.3 Hz, 1H), 7.47-7.27 (m, 7H), 7.14-7.11 (m, 1H), 7.08-7.06 (m, 1H), 6.92-6.87 (m, 2H), 4.74 (s, 2H), 4.51 (s, 2H), 4.46 (s, 2H), 3.87 (s, 3H), 1.52 (s, 9H), 1.42 (s, 9H)

11-(c): {6[(3'-Methoxybiphenyl-4-ylmethyl)(pyridin-2-ylsulfonyl)-aminomethyl]pyridin-2-ylamino}acetic acid To a solution of 312 mg (0.462 mmol) of tert-butyl (tert-butoxycarbonyl {6-[(3'-methoxybiphenyl-4-ylmethyl)(pyridin-2-ylsulfonyl)-aminomethyl]pyridin-2-yl}amino) acetate obtained in Comparative Example 11-(b) in 3.7 mL of methylene chloride, 3.7 mL (48 mmol) of trifluoroacetic acid was added at room temperature and allowed to stand undisturbed for 4 hours. After the completion of the reaction, the reaction solution was concentrated under reduced pressure. Thereafter, water was added to the reaction solution, and pH of the solution was adjusted to 4.4 with saturated aqueous sodium bicarbonate solution and 1 mol/L hydrochloric acid, followed by extraction with ethyl acetate. The organic layer was washed with saturated aqueous sodium chloride solution, dried over anhydrous sodium sulfate, and then concentrated under reduced pressure to afford 257 mg of the title compound as a white foam. (Quantitative)

Mass spectrum (FAB, m/z): 519 ($M^+$+1)

$^1$H-NMR spectrum (DMSO-d$_6$, δ ppm): 12.41 (brs, 0.9H), 8.64 (ddd, J=4.8, 1.8, 1.0 Hz, 1H), 7.95 (ddd, J=7.8, 7.8, 1.8 Hz, 1H), 7.80 (ddd, J=7.8, 1.0, 1.0 Hz, 1H), 7.59-7.56 (m, 3H), 7.37 (dd, J=8.0, 8.0 Hz, 1H), 7.34-7.31 (m, 2H), 7.21-7.18 (m, 2H), 7.15 (dd, J=2.0, 2.0 Hz, 1H), 6.93 (ddd, J=8.0, 2.0, 1.1 Hz, 1H), 6.77 (brs, 1H), 6.35 (d, J=8.1 Hz, 1H), 6.29 (d, J=7.0 Hz, 1H), 4.74 (s, 2H), 4.24 (s, 2H), 3.84 (s, 2H), 182 (s, 3H)

Comparative Example 12

{6-[(3'-Propoxybiphenyl-4-ylmethyl)(pyridin-2-ylsulfonyl)aminomethyl]-pyridin-2-ylamino}acetic acid This compound is the compound of Example Number 803 described in WO2009/113600.

12-(a): tert-Butyl (tert-butoxycarbonyl{6-[(3'-propoxybiphenyl-4-ylmethyl)-(pyridin-2-ylsulfonyl)aminomethyl]pyridin-2-yl}amino)acetate The reaction and post-treatment were performed in accordance with Reference Example 5 except for using 401 mg (0.577 mmol) of tert-butyl (tert-butoxycarbonyl {6-[(4-iodobenzyl)(pyridin-2-ylsulfonyl)aminomethyl]pyridin-2-yl}amino)acetate obtained in Comparative Example 11-(a) in place of 3-bromophenetole, using 156 mg (0.868 mmol) of 3-propoxyphenylboronic acid in place of 4-(hydroxymethyl)phenylboronic acid, and using 1.3 mL (2.6 mmol) of 2 mol/L aqueous sodium carbonate solution and 67 mg (0.058 mmol) of tetrakis(triphenylphosphine)palladium, to afford 332 mg of the title compound as a white foam. (Yield: 82%)

Mass spectrum (CI, m/z): 703 ($M^+$+1)

$^1$H-NMR spectrum (CDCl$_3$, δ ppm): 8.60 (ddd, J=4.7, 1.8, 1.0 Hz, 1H), 7.82 (ddd, J=7.7, 1.0, 1.0 Hz, 1H), 7.76 (ddd, J=7.7, 7.7, 1.8 Hz, 1H), 7.65 (d, J=8.3 Hz, 1H), 7.48-7.26 (m, 7H), 7.12-7.07 (m, 2H), 6.93-6.86 (m, 2H), 4.73 (s, 2H), 4.51 (s, 2H), 4.46 (s, 2H), 3.98 (t, J=6.6 Hz, 2H), 1.90-1.78 (m, 2H), 1.52 (s, 9H), 1.42 (s, 9H), 1.06 (t, J=7.4 Hz, 3H)

12-(b): {6-[(3'-Propoxybiphenyl-4-ylmethyl)(pyridin-2-ylsulfonyl)-aminomethyl]pyridin-2-ylamino}acetic acid To a solution of 328 mg (0.466 mmol) of tert-butyl (tert-butoxycarbonyl{6-[(3'-propoxybiphenyl-4-ylmethyl)(pyridin-2-ylsulfonyl)-aminomethyl]pyridin-2-yl}amino) acetate obtained in Comparative Example 12-(a) in 4.7 mL of methylene chloride, 4.7 mL (61 mmol) of trifluoroacetic acid was added at room temperature and allowed to stand undisturbed for 5 hours. After the completion of the reaction, the reaction solution was concentrated under reduced pressure. Thereafter, water was added to the reaction solution, and pH of the solution was adjusted to 4.4 with saturated aqueous sodium bicarbonate solution and 1 mol/L hydrochloric acid, followed by extraction with ethyl acetate. The organic layer was washed with saturated aqueous sodium chloride solution, dried over anhydrous sodium sulfate, and then concentrated under reduced pressure. The residue was subjected to silica gel column chromatography (elution solvent; ethyl acetate:acetic acid=100:1 (V/V)), and fractions containing the target product were concentrated under reduced pressure to afford 158 mg of the title compound as a white foam. (Yield: 62%)

Mass spectrum (FAB, m/z): 547 ($M^+$+1)

$^1$H-NMR spectrum (DMSO-d$_6$, δ ppm): 12.34 (brs, 0.7H), 8.64 (ddd, J=4.7, 1.8, 1.0 Hz, 1H), 7.95 (ddd, J=7.7, 7.7, 1.8 Hz, 1H), 7.80 (ddd, J=7.7, 1.0, 1.0 Hz, 1H), 7.59-7.56 (m, 3H), 7.35 (dd, J=8.1, 8.0 Hz, 1H), 7.33-7.31 (m, 2H), 7.21-7.17 (m, 2H), 7.14 (dd, J=2.1, 2.0 Hz, 1H), 6.92 (ddd, J=8.1, 2.1, 1.1 Hz, 1H), 6.75 (t, J=5.9 Hz, 1H), 6.34 (d, J=8.4 Hz, 1H), 6.28 (d, J=7.3 Hz, 1H), 4.74 (s, 2H), 4.24 (s, 2H), 4.00 (t, J=6.4 Hz, 2H), 3.82 (d, J=5.9 Hz, 2H), 1.79-1.72 (m, 2H), 1.00 (t, J=7.4 Hz, 3H)

Comparative Example 13

{6-[(2'-Ethoxybiphenyl-4-ylmethyl)(pyridin-2-ylsulfonyl)aminomethyl]pyridin-2-ylamino}acetic acid 13-(a): tert-Butyl ({6-[(4-bromobenzyl)(pyridin-2-ylsulfonyl)aminomethyl]-pyridin-2-yl}tert-butoxycarbonylamino)acetate The reaction and post-treatment were performed in accordance with Comparative Example 11-(a) except for using 787 mg (3.15 mmol) of 4-bromobenzyl bromide in place of 4-iodobenzyl bromide, and using 1.44 g (3.00 mmol) of tert-butyl (tert-butoxycarbonyl {6-[(pyridin-2-ylsulfonyl)aminomethyl]pyridin-2-yl}amino)acetate obtained in the same manner as in Reference Example 1-(f) and 830 mg (6.00 mmol) of potassium carbonate, to afford 1.77 g of the title compound as a slightly yellow oil. (Yield: 91%)

Mass spectrum (FAB, m/z): 647, 649 ($M^+$+1)

¹H-NMR spectrum (CDCl₃, δ ppm): 8.59 (ddd, J=4.8, 1.8, 1.0 Hz, 1H), 7.83-7.75 (m, 2H), 7.65 (d, J=8.5 Hz, 1H), 7.47-7.33 (m, 4H), 7.15-7.10 (m, 2H), 6.87 (d, J=6.8 Hz, 1H), 4.66 (s, 2H), 4.44 (s, 2H), 4.43 (s, 2H), 1.52 (s, 9H), 1.42 (s, 9H)

13-(b): tert-Butyl (tert-butoxycarbonyl {6-[(2'-ethoxybiphenyl-4-ylmethyl)-(pyridin-2-ylsulfonyl)aminomethyl]pyridin-2-yl}amino)acetate The reaction and post-treatment were performed in accordance with Reference Example 5 except for using 518 mg (0.800 mmol) of tert-butyl ({6-[(4-bromobenzyl)(pyridin-2-ylsulfonyl)aminomethyl]pyridin-2-yl}tert-butoxycarbonylamino)acetate obtained in Comparative Example 13-(a) in place of 3-bromophenetole, using 199 mg (1.20 mmol) of 2-ethoxyphenylboronic acid in place of 4-(hydroxymethyl)phenylboronic acid, and using 0.60 mL (1.2 mmol) of 2 mol/L aqueous sodium carbonate solution and 46.2 mg (0.0400 mmol) of tetrakis(triphenylphosphine)palladium, to afford 548 mg of the title compound as a slightly yellowish white foam. (Yield: 99%)

Mass spectrum (FAB, m/z): 689 (M⁺+1)

¹H-NMR spectrum (CDCl₃, δ ppm): 8.60 (ddd, J=4.7, 1.8, 1.0 Hz, 1H), 7.83-7.73 (m, 2H), 7.65 (d, J=8.8 Hz, 1H), 7.48-7.41 (m, 3H), 7.37 (ddd, J=7.3, 4.7, 1.4 Hz, 1H), 7.31-7.23 (m, 4H), 7.03-6.91 (m, 3H), 4.74 (s, 2H), 4.53 (s, 2H), 4.46 (s, 2H), 4.03 (q, J=7.0 Hz, 2H), 1.52 (s, 9H), 1.43 (s, 9H), 1.35 (t, J=7.0 Hz, 3H)

13-(c): {6-[(2'-Ethoxybiphenyl-4-ylmethyl)(pyridin-2-ylsulfonyl)-aminomethyl]pyridin-2-ylamino}acetic acid The reaction and post-treatment were performed in accordance with Example 7-(b) except for using 541 mg (0.785 mmol) of tert-butyl (tert-butoxycarbonyl-{6-[(2'-ethoxybiphenyl-4-ylmethyl)(pyridin-2-ylsulfonyl)aminomethyl]-pyridin-2-yl}amino)acetate obtained in Comparative Example 13-(b) in place of tert-butyl (tert-butoxycarbonyl {6-[(3'-ethoxybiphenyl-4-ylmethyl)(pyridin-2-yl-sulfonyl)aminomethyl]pyridin-2-yl}amino)acetate, and using 3.3 mL (20 mmol) of 6 mol/L hydrochloric acid and 1.0 mL of water, to afford 413 mg of the title compound as a slightly yellowish white foam. (Yield: 99%)

Mass spectrum (FAB, m/z): 533 (M⁺+1)

¹H-NMR spectrum (DMSO-d₆, δ ppm): 12.42 (brs, 0.6H), 8.64 (ddd, J=4.8, 1.8, 1.0 Hz, 1H), 7.94 (ddd, J=7.7, 7.7, 1.8 Hz, 1H), 7.79 (ddd, J=7.7, 1.0, 1.0 Hz, 1H), 7.57 (ddd, J=7.7, 4.8, 1.0 Hz, 1H), 7.44-7.41 (m, 2H), 7.33-7.26 (m, 4H), 7.20 (dd, J=8.4, 7.2 Hz, 1H), 7.09-7.07 (m, 1H), 7.01 (ddd, J=7.5, 7.5, 1.1 Hz, 1H), 6.75 (t, J=5.6 Hz, 1H), 6.34 (d, J=8.4 Hz, 1H), 6.29 (d, J=7.2 Hz, 1H), 4.74 (s, 2H), 4.26 (s, 2H), 4.04 (q, J=7.0 Hz, 2H), 3.82 (d, J=5.6 Hz, 2H), 1.27 (t, J=7.0 Hz, 3H)

Comparative Example 14

{6-[(4'-Ethoxybiphenyl-4-ylmethyl)(pyridin-2-ylsulfonyl)aminomethyl]-pyridin-2-ylamino}acetic acid 14-(a): tert-Butyl (tert-butoxycarbonyl{6-[(4'-ethoxybiphenyl-4-ylmethyl)-(pyridin-2-ylsulfonyl)aminomethyl]pyridin-2-yl}amino)acetate The reaction and post-treatment were performed in accordance with Reference Example 5 except for using 389 mg (0.600 mmol) of tert-butyl ({6-[(4-bromobenzyl)(pyridin-2-ylsulfonyl)aminomethyl]pyridin-2-yl}tert-butoxycarbonylamino)acetate obtained in the same manner as in Comparative Example 13-(a) in place of 3-bromophenetole, using 150 mg (0.900 mmol) of 4-ethoxyphenylboronic acid in place of 4-(hydroxymethyl)phenylboronic acid, and using 0.45 mL (0.90 mmol) of 2 mol/L aqueous sodium carbonate solution and 34.7 mg (0.0300 mmol) of tetrakis(triphenylphosphine)palladium, to afford 395 mg of the title compound as a slightly yellowish white foam. (Yield: 96%)

Mass spectrum (FAB, m/z): 689 (M⁺+1)

¹H-NMR spectrum (CDCl₃, δ ppm): 8.60 (ddd, J=4.6, 1.7, 1.0 Hz, 1H), 7.82 (ddd, J=7.7, 1.0, 1.0 Hz, 1H), 7.76 (ddd, J=7.7, 7.6, 1.7 Hz, 1H), 7.65 (d, J=8.1 Hz, 1H), 7.49-7.36 (m, 6H), 7.27-7.24 (m, 2H), 6.97-6.90 (m, 3H), 4.72 (s, 2H), 4.51 (s, 2H), 4.46 (s, 2H), 4.08 (q, J=7.0 Hz, 2H), 1.52 (s, 9H), 1.44 (t, J=7.0 Hz, 3H), 1.42 (s, 9H)

14-(b): {6-[(4'-Ethoxybiphenyl-4-ylmethyl)(pyridin-2-ylsulfonyl)-aminomethyl]pyridin-2-ylamino}acetic acid The reaction and post-treatment were performed in accordance with Example 7-(b) except for using 390 mg (0.566 mmol) of tert-butyl (tert-butoxycarbonyl-{6-[(4'-ethoxybiphenyl-4-ylmethyl)(pyridin-2-ylsulfonyl)aminomethyl] pyridin-2-yl}-amino)acetate obtained in Comparative Example 14-(a) in place of tert-butyl (tert-butoxycarbonyl {6-[(3'-ethoxybiphenyl-4-ylmethyl)(pyridin-2-ylsulfonyl)-aminomethyl]pyridin-2-yl}amino)acetate, and using 2.35 mL (14.1 mmol) of 6 mol/L hydrochloric acid and 0.65 mL of water, to afford 296 mg of the title compound as a slightly yellowish white foam. (Yield: 98%)

Mass spectrum (FAB, m/z): 533 (M⁺+1)

¹H-NMR spectrum (DMSO-d₆, δ ppm): 12.42 (brs, 0.8H), 8.63 (ddd, J=4.8, 1.8, 0.9 Hz, 1H), 7.94 (ddd, J=7.8, 7.8, 1.8 Hz, 1H), 7.79 (ddd, J=7.8, 0.9, 0.9 Hz, 1H), 7.59-7.55 (m, 3H), 7.52-7.50 (m, 2H), 7.30-7.28 (m, 2H), 7.19 (dd, J=8.4, 7.1 Hz, 1H), 7.01-6.98 (m, 2H), 6.75 (t, J=5.8 Hz, 1H), 6.34 (d, J=8.4 Hz, 1H), 6.28 (d, J=7.1 Hz, 1H), 4.72 (s, 2H), 4.23 (s, 2H), 4.06 (q, J=7.0 Hz, 2H), 3.82 (d, J=5.8 Hz, 2H), 1.35 (t, J=7.0 Hz, 3H)

Comparative Example 15

(6-{[4-(2-Ethoxypyridin-4-yl)benzyl](pyridin-2-ylsulfonyl)aminomethyl}-pyridin-2-ylamino)acetic acid 15-(a): 4-(2-Ethoxypyridin-4-yl)phenylmethanol The reaction and post-treatment were performed in accordance with Reference Example 5 except for using 0.55 g (2.7 mmol) of 4-bromo-2-ethoxypyridine (see Tetrahedron Letters, 51, 3041 (2010)) in place of 3-bromophenetole, and using 0.66 g (4.3 mmol) of 4-(hydroxymethyl)phenylboronic acid, 1.9 mL (3.8 mmol) of 2 mol/L aqueous sodium carbonate solution, and 154 mg (0.133 mmol) of tetrakis(triphenylphosphine)palladium, to afford 250 mg of the title compound as a yellow oil. (Yield: 40%)

Mass spectrum (CI, m/z): 230 (M⁺+1)

¹H-NMR spectrum (CDCl₃, δ ppm): 8.19 (dd, J=5.4, 0.7 Hz, 1H), 7.64-7.60 (m, 2H), 7.49-7.45 (m, 2H), 7.09 (dd, J=5.4, 1.5 Hz, 1H), 6.94 (dd, J=1.5, 0.7 Hz, 1H), 4.76 (d, J=5.2 Hz, 2H), 4.40 (q, J=7.0 Hz, 2H), 1.79 (t, J=5.2 Hz, 0.9H), 1.43 (t, J=7.0 Hz, 3H)

15-(b): tert-Butyl [tert-butoxycarbonyl(6-{[4-(2-ethoxypyridin-4-yl)-benzyl](pyridin-2-ylsulfonyl)aminomethyl}pyridin-2-yl)amino]acetate The reaction and post-treatment were performed in accordance with Example 1 except for using 505 mg (1.06 mmol) of tert-butyl (tert-butoxycarbonyl-{6-[(pyridin-2-ylsulfonyl)aminomethyl]pyridin-2-yl}amino)acetate obtained in the same manner as in Reference Example 1-(f) and 242 mg (1.06 mmol) of 4-(2-ethoxypyridin-4-yl)phenylmethanol obtained in Comparative Example 15-(a) in place of 3'-(1-propenyl)biphenyl-4-ylmethanol, and using 662 μL (2.65 mmol) of tri-n-butylphosphine and 273 mg (1.59 mmol) of N,N,N',N'-tetramethylazodicarboxamide, to afford 0.49 g of the title compound as a white foam. (Yield: 67%)

Mass spectrum (CI, m/z): 690 (M$^+$+1)

$^1$H-NMR spectrum (CDCl$_3$, δ ppm): 8.60 (ddd, J=4.8, 1.7, 1.0 Hz, 1H), 8.18 (dd, J=5.4, 0.7 Hz, 1H), 7.83 (ddd, J=7.7, 1.1, 1.0 Hz, 1H), 7.77 (ddd, J=7.7, 7.5, 1.7 Hz, 1H), 7.65 (d, J=8.3 Hz, 1H), 7.49-7.45 (m, 2H), 7.44 (dd, J=8.3, 7.3 Hz, 1H), 7.39 (ddd, J=7.5, 4.8, 1.1 Hz, 1H), 7.35-7.31 (m, 2H), 7.04 (dd, J=5.4, 1.5 Hz, 1H), 6.92-6.88 (m, 2H), 4.76 (s, 2H), 4.50 (s, 2H), 4.44 (s, 2H), 4.41 (q, J=7.1 Hz, 2H), 1.52 (s, 9H), 1.43 (t, J=7.1 Hz, 3H), 1.42 (s, 9H)

15-(c): (6-{[4-(2-Ethoxypyridin-4-yl)benzyl](pyridin-2-ylsulfonyl)-aminomethyl}pyridin-2-ylamino)acetic acid To a solution of 0.47 g (0.68 mmol) of tert-butyl [tert-butoxycarbonyl(6-{[4-(2-ethoxypyridin-4-yl)benzyl](pyridin-2-ylsulfonyl)-aminomethyl}pyridin-2-yl)amino]acetate obtained in Comparative Example 15-(b) in 6.8 mL of methylene chloride, 6.8 mL (89 mmol) of trifluoroacetic acid was added at room temperature and stirred for 6.5 hours. After the completion of the reaction, the reaction solution was concentrated under reduced pressure. Thereafter, water was added to the reaction solution, and pH of the solution was adjusted to 4.5 with 2 mol/L aqueous sodium hydroxide solution and 0.1 mol/L hydrochloric acid, followed by extraction with ethyl acetate. The organic layer was washed with saturated aqueous sodium chloride solution, dried over anhydrous magnesium sulfate, and then concentrated under reduced pressure to afford 293 mg of the title compound. (Yield: 81%)

Mass spectrum (FAB, m/z): 534 (M$^+$+1)

$^1$H-NMR spectrum (DMSO-d$_6$, δ ppm): 12.52 (brs, 0.7H), 8.66 (dd, J=4.7, 1.7 Hz, 1H), 8.20 (dd, J=5.5, 0.7 Hz, 1H), 7.98 (dd, J=7.7, 7.7 Hz, 1H), 7.83 (d, J=7.4 Hz, 1H), 7.69-7.66 (m, 2H), 7.61 (dd, J=7.7, 4.7 Hz, 1H), 7.37-7.35 (m, 2H), 7.28 (brs, 1H), 7.26 (dd, J=5.5, 1.5 Hz, 1H), 7.04 (dd, J=1.5, 0.7 Hz, 1H), 6.42 (s, 1H), 6.35 (s, 1H), 4.73 (s, 2H), 4.35 (q, J=7.1 Hz, 2H), 4.32 (s, 2H), 3.86 (s, 2H), 1.34 (t, J=7.1 Hz, 3H)

Comparative Example 16

(6-{[2'-(1-Propynyl)biphenyl-4-ylmethyl](pyridin-2-ylsulfonyl)aminomethyl}pyridin-2-ylamino)acetic acid

16-(a): 1-Bromo-2-(1-propynyl)benzene

The reaction and post-treatment were performed in accordance with Reference Example 12-(a) except for using 7.07 g (25.0 mmol) of 1-bromo-2-iodobenzene in place of 1-bromo-3-iodobenzene, and using 1.43 g (7.51 mmol) of copper(I) iodide, 1.45 g (1.25 mmol) of tetrakis(triphenylphosphine)palladium, 2.81 g (25.0 mmol) of 1-trimethylsilyl-1-propyne, 11.5 mL (82.5 mmol) of triethylamine, and 25.0 mL (25.0 mmol) of 1 mol/L tetrafluoroammonium fluoride/tetrahydrofuran solution, to afford 3.77 g of the title compound as a colorless oil. (Yield: 77%)

Mass spectrum (CI, m/z): 195, 197 (M$^+$+1)

$^1$H-NMR spectrum (CDCl$_3$, δ ppm): 7.55 (dd, J=8.0, 1.1 Hz, 1H), 7.42 (dd, J=7.7, 1.7 Hz, 1H), 7.22 (ddd, J=7.7, 7.7, 1.1 Hz, 1H), 7.11 (ddd, J=8.0, 7.7, 1.7 Hz, 1H), 2.12 (s, 3H)

16-(b): 2'-(1-Propynyl)biphenyl-4-ylmethanol

The reaction and post-treatment were performed in accordance with Reference Example 5 except for using 1.95 g (10.0 mmol) of 1-bromo-2-(1-propynyl)benzene obtained in Comparative Example 16-(a) in place of 3-bromophenetole, and using 2.28 g (15.0 mmol) of 4-(hydroxymethyl)phenylboronic acid, 7.5 mL (15 mmol) of 2 mol/L aqueous sodium carbonate solution, and 580 mg (0.502 mmol) of tetrakis(triphenylphosphine)palladium, to afford 1.86 g of the title compound as a pale yellow oil. (Yield: 83%)

Mass spectrum (EI, m/z): 222 (M$^+$)

$^1$H-NMR spectrum (CDCl$_3$, δ ppm): 7.62-7.59 (m, 2H), 7.52-7.50 (m, 1H), 7.44-7.41 (m, 2H), 7.35-7.24 (m, 3H), 4.76 (d, J=5.9 Hz, 2H), 1.94 (s, 3H), 1.73 (t, J=5.9 Hz, 1H)

16-(c): Ethyl (6-{[2'-(1-propynyl)biphenyl-4-ylmethyl](pyridin-2-ylsulfonyl)-aminomethyl}pyridine-2-ylamino)acetate The reaction and post-treatment were performed in accordance with Example 1 except for using 280 mg (0.800 mmol) of ethyl {6-[(pyridin-2-ylsulfonyl)aminomethyl]pyridin-2-ylamino}acetate obtained in the same manner as in Reference Example 1-(g) and 178 mg (0.800 mmol) of 2'-(1-propynyl)biphenyl-4-ylmethanol obtained in Comparative Example 16-(b) in place of 3'-(1-propenyl)biphenyl-4-ylmethanol, and using 395 μL (1.60 mmol) of tri-n-butylphosphine and 276 mg (1.60 mmol) of N,N,N',N'-tetramethylazodicarboxamide, to afford 420 mg of the title compound as a colorless syrup. (Yield: 95%)

Mass spectrum (CI, m/z): 555 (M$^+$+1)

$^1$H-NMR spectrum (CDCl$_3$, δ ppm): 8.62 (ddd, J=4.7, 1.7, 1.0 Hz, 1H), 7.81 (ddd, J=7.7, 1.0, 1.0 Hz, 1H), 7.75 (ddd, J=7.7, 7.7, 1.7 Hz, 1H), 7.51-7.47 (m, 3H), 7.39-7.22 (m, 7H), 6.51 (d, J=7.0 Hz, 1H), 6.23 (d, J=8.2 Hz, 1H), 4.82 (s, 2H), 4.69 (t, J=5.4 Hz, 1H), 4.44 (s, 2H), 4.22 (q, J=7.1 Hz, 2H), 3.96 (d, J=5.4 Hz, 2H), 1.94 (s, 3H), 1.28 (t, J=7.1 Hz, 3H)

16-(d): (6-{[2'-(1-Propynyl)biphenyl-4-ylmethyl](pyridin-2-ylsulfonyl)-aminomethyl}pyridine-2-ylamino)acetic acid To a solution of 415 mg (0.748 mmol) of ethyl (6-{[2'-(1-propynyl)biphenyl-4-ylmethyl](pyridin-2-ylsulfonyl)aminomethyl}pyridin-2-ylamino)acetate obtained in Comparative Example 16-(c) in 3.0 mL of ethanol, 3.0 mL (3.0 mmol) of 1 mol/L aqueous sodium hydroxide solution was added and stirred for 20 hours at room temperature. After the completion of the reaction, water was added to the reaction solution, and then pH of the solution was adjusted to 4.5 with 1 mol/L hydrochloric acid. The obtained slurry solution was heated to 50° C. and then cooled to room temperature for 2 hours with stirring. The precipitated solid was collected by filtration and then dried under reduced pressure to afford 357 mg of the title compound as a pale yellowish white solid. (Yield: 91%)

Mass spectrum (ESI$^+$, m/z): 527 (M$^+$+1)

$^1$H-NMR spectrum (DMSO-d$_6$, δ ppm): 12.44 (brs, 0.6H), 8.65 (ddd, J=4.7, 1.0, 1.0 Hz, 1H), 7.95 (ddd, J=7.7, 7.7, 1.7 Hz, 1H), 7.80 (ddd, J=7.7, 1.0, 1.0 Hz, 1H), 7.58 (ddd, J=7.7, 4.7, 1.0 Hz, 1H), 7.51-7.46 (m, 3H), 7.43-7.30 (m, 5H), 7.20 (dd, J=8.3, 7.1 Hz, 1H), 6.74 (t, J=5.5 Hz, 1H), 6.34 (d, J=8.3 Hz, 1H), 6.29 (d, J=7.1 Hz, 1H), 4.76 (s, 2H), 4.27 (s, 2H), 3.82 (d, J=5.5 Hz, 2H), 1.93 (s, 3H)

Comparative Example 17

(6-{[4'-(1-Propynyl)biphenyl-4-ylmethyl](pyridin-2-ylsulfonyl)aminomethyl}-pyridin-2-ylamino)acetic acid 17-(a): 1-Bromo-4-(1-propynyl)benzene The reaction and post-treatment were performed in accordance with Reference Example 12-(a) except for using 7.07 g (25.0 mmol) of 1-bromo-4-iodobenzene in place of 1-bromo-3-iodobenzene, and using 1.43 g (7.51 mmol) of copper(I) iodide, 1.45 g (1.25 mmol) of tetrakis(triphenylphosphine)palladium, 2.81 g (25.0 mmol) of 1-trimethylsilyl-1-propyne, 11.5 mL (82.5 mmol) of triethylamine, and 25.0 mL (25.0 mmol) of 1 mol/L tetrafluoroammonium fluoride/tetrahydrofuran solution, to afford 4.11 g of the title compound as a white solid. (Yield: 84%)

Mass spectrum (CI, m/z): 195, 197 (M$^+$+1)
$^1$H-NMR spectrum (CDCl$_3$, δ ppm): 7.42-7.39 (m, 2H), 7.26-7.22 (m, 2H), 2.03 (s, 3H)

17-(b): 4'-(1-Propynyl)biphenyl-4-ylmethanol

The reaction and post-treatment were performed in accordance with Reference Example 5 except for using 1.95 g (10.0 mmol) of 1-bromo-4-(1-propynyl)benzene obtained in Comparative Example 17-(a) in place of 3-bromophenetole, and using 2.28 g (15.0 mmol) of 4-(hydroxymethyl)phenylboronic acid, 7.5 mL (15 mmol) of 2 mol/L aqueous sodium carbonate solution, and 581 mg (0.503 mmol) of tetrakis(triphenylphosphine)palladium, to afford 1.95 g of the title compound as a slightly yellow solid. (Yield: 88%)

Mass spectrum (EI, m/z): 222 (M$^+$)
$^1$H-NMR spectrum (CDCl$_3$, δ ppm): 7.60-7.56 (m, 2H), 7.53-7.50 (m, 2H), 7.47-7.42 (m, 4H), 4.74 (d, J=5.9 Hz, 2H), 2.08 (s, 3H), 1.68 (t, J=5.9 Hz, 1H)

17-(c): Ethyl (6-{[4'-(1-propynyl)biphenyl-4-ylmethyl](pyridin-2-ylsulfonyl)aminomethyl}pyridine-2-ylamino)acetate The reaction and post-treatment were performed in accordance with Example 1 except for using 281 mg (0.801 mmol) of ethyl {6-[(pyridin-2-ylsulfonyl)aminomethyl] pyridin-2-ylamino}acetate obtained in the same manner as in Reference Example 1-(g) and 180 mg (0.810 mmol) of 4'-(1-propynyl)biphenyl-4-ylmethanol obtained in Comparative Example 17-(b) in place of 3'-(1-propenyl)biphenyl-4-ylmethanol, and using 395 μL (1.60 mmol) of tri-n-butylphosphine and 276 mg (1.60 mmol) of N,N,N',N'-tetramethylazodicarboxamide, to afford 419 mg of the title compound as a colorless syrup. (Yield: 94%)

Mass spectrum (CI, m/z): 555 (M$^+$+1)
$^1$H-NMR spectrum (CDCl$_3$, δ ppm): 8.61 (ddd, J=4.7, 1.7, 1.0 Hz, Hi), 7.83 (ddd, J=7.7, 1.0, 1.0 Hz, 1H), 7.75 (ddd, J=7.7, 7.7, 1.7 Hz, 1H), 7.50-7.43 (m, 6H), 7.38 (ddd, J=7.7, 4.7, 1.0 Hz, 1H), 7.36-7.33 (m, 2H), 7.23 (dd, J=8.2, 7.3 Hz, 1H), 6.50 (d, J=7.3 Hz, 1H), 6.22 (d, J=8.2 Hz, 1H), 4.79 (s, 2H), 4.69 (t, J=5.4 Hz, 1H), 4.41 (s, 2H), 4.22 (q, J=7.2 Hz, 2H), 3.95 (d, J=5.4 Hz, 2H), 2.08 (s, 3H), 1.28 (t, J=7.2 Hz, 3H)

17-(d): (6-{[4'-(1-Propynyl)biphenyl-4-ylmethyl](pyridin-2-ylsulfonyl)-aminomethyl}pyridine-2-ylamino)acetic acid The reaction and post-treatment were performed in accordance with Comparative Example 16-(d) except for using 415 mg (0.748 mmol) of ethyl (6-{[4'-(1-propynyl)biphenyl-4-ylmethyl](pyridin-2-ylsulfonyl)aminomethyl}pyridin-2-ylamino)acetate obtained in Comparative Example 17-(c) in place of ethyl (6-{[2'-(1-propynyl)biphenyl-4-ylmethyl](pyridin-2-ylsulfonyl)aminomethyl}pyridine-2-ylamino)acetate, and using 3.0 mL (3.0 mmol) of 1 mol/L aqueous sodium hydroxide solution, to afford 371 mg of the title compound as a white solid. (Yield: 94%)

Mass spectrum (ESI$^+$, m/z): 527 (M$^+$+1)
$^1$H-NMR spectrum (DMSO-d$_6$, δ ppm): 12.43 (brs, 0.7H), 8.64 (ddd, J=4.7, 1.7, 1.0 Hz, 1H), 7.95 (ddd, J=7.7, 7.7, 1.7 Hz, 1H), 7.80 (ddd, J=7.7, 1.0, 1.0 Hz, 1H), 7.64-7.56 (m, 5H), 7.47-7.44 (m, 2H), 7.35-7.32 (m, 2H), 7.19 (dd, J=8.3, 7.2 Hz, 1H), 6.75 (t, J=5.7 Hz, 1H), 6.34 (d, J=8.3 Hz, 1H), 6.28 (d, J=7.2 Hz, 1H), 4.74 (s, 2H), 4.24 (s, 2H), 3.81 (d, J=5.7 Hz, 2H), 2.07 (s, 3H)

Test Example 1

Measurement of EP2 Receptor Binding Action

Measurement of EP2 receptor binding action was performed in accordance with the method of Abramovitz et al. (Biochimica et Biophysica Acta, 1483, 285 (2000)). A test compound dissolved in dimethyl sulfoxide (final concentration: 1.0 (V/V) %) and [$^3$H]prostaglandin E$_2$ (NET-428, manufactured by PerkinElmer) (final concentration: 10 nM) were added to a buffer solution (10 mM MES-KOH (pH 6.0), 10 mM MgCl$_2$, 1 mM EDTA) in which 10 μg of a membrane fraction of HEK293 cells expressing human EP2 receptor (ES-562-M, manufactured by Euroscreen) was suspended, and then incubated at 30° C. for 60 minutes. The membrane fraction was recovered on glass fiber filter paper (GF/B, manufactured by Whatman) using a cell harvester (M30R, manufactured by Brandel), and after washing with a buffer solution (10 mM MES-KOH (pH 6.0), 10 mM MgCl$_2$), radioactivity was measured with a liquid scintillation analyzer (2000CA, manufactured by Packard). The concentration of test compound required to replace 50% of the [$^3$H]prostaglandin E$_2$ bound to the receptor (IC$_{50}$ value) was calculated using EXSAS (Ver. 7.1.6, manufactured by Arm Systex), and the inhibition constant (Ki value) was determined using the formula described below.

$Ki=IC_{50}/(1+([^3H]$prostaglandin $E_2$ concentration$/Kd))$

Note that the dissociation constant (Kd value) was calculated by Scatchard analysis.

The test results are shown in Table 1.

TABLE 1

| Test compound No. | Ki value (nM) of EP2 receptor binding action |
|---|---|
| Example 2 | 0.53 |
| Example 4 | 0.80 |
| Example 6 | 0.75 |
| Example 7 | 0.61 |
| Example 9 | 0.80 |
| Example 10 | 0.97 |
| Example 11 | 0.79 |
| Example 12 | 0.94 |
| Example 14 | 0.90 |

TABLE 1-continued

| Test compound No. | Ki value (nM) of EP2 receptor binding action |
|---|---|
| Example16 | 0.95 |
| Example18 | 0.99 |
| Example19 | 1.4 |
| Comparative example 1 | 1.5 |
| Comparative example 2 | 3.8 |
| Comparative example 3 | 4.4 |
| Comparative example 4 | >10 |
| Comparative example 5 | >10 |
| Comparative example 6 | 2.2 |
| Comparative example 7 | 1.4 |
| Comparative example 8 | 1.1 |
| Comparative example 9 | 1.5 |
| Comparative example10 | 1.7 |
| Comparative example11 | 1.2 |
| Comparative example12 | 2.0 |
| Comparative example13 | 2.6 |
| Comparative example14 | >10 |
| Comparative example15 | 3.2 |
| Comparative example16 | 0.75 |
| Comparative example17 | 6.8 |

In this test, compounds of the present invention demonstrated superior EP2 receptor binding action.

Test Example 2

Test for Inhibition of Pulmonary Fibroblast Proliferation

Measurement of inhibition effect of pulmonary fibroblast proliferation was performed by modifying the method of Huang et al. (American Journal of Respiratory Cell and Molecular Biology, 39, 482 (2008)). Pulmonary fibroblasts derived from a human fetus (IMR90, purchased from American Type Culture Collection) were cultured in DMEM medium containing 10% FBS and seeded at 1×10⁴ cells/well of a 96-well plate. After culturing for approximately 8 hours in a carbon dioxide incubator, the medium was replaced with FBS-free DMEM medium and the culturing was performed for one night. On the following day, the medium was replaced with a new FBS-free DMEM medium, and then a test compound dissolved in dimethyl sulfoxide (final concentration: 0.1%) and FGF (final concentration: 10 ng/mL, manufactured by Wako Pure Chemical Industries, Ltd.) were added thereto and allowed to stand undisturbed in a carbon dioxide incubator. After 22 hours, a BrdU labeling solution (manufactured by Roche) was added and culturing was performed for another 2 hours. After the completion of the culturing, amount of BrdU incorporation was measured using Cell Proliferation ELISA BrdU (colorimetric) (manufactured by Roche). The concentration of the test compound required to inhibit BrdU incorporation to 50% ($IC_{50}$ value) was calculated by non-linear regression of the test compound concentration and the amount of BrdU incorporation using EXSAS (Ver. 8.0.0, manufactured by Arm Systex).

The test results are shown in Tables 2 and 3.

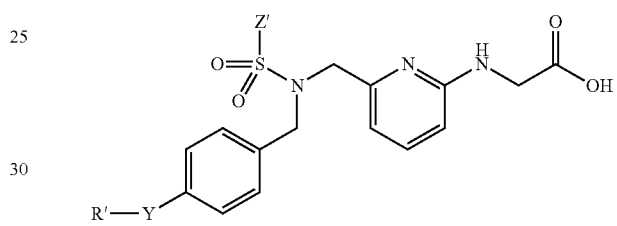

TABLE 2

| Test compound No. | R'—Y— | Z' | $IC_{50}$ value (nM) of inhibition effect of pulmonary fibroblast proliferation |
|---|---|---|---|
| Example 2 | propenyl-phenyl | 2-pyridyl | 0.035 |
| Example 4 | ethynyl-phenyl | 2-pyridyl | 0.016 |
| Example 6 | ethynyl-phenyl | 3-pyridyl | 0.045 |
| Example 14 | ethynyl-phenyl | 2-thienyl | 0.011 |

TABLE 2-continued
| Test compound No. | R'—Y | Z' | IC$_{50}$ value (nM) of inhibition effect of pulmonary fibroblast proliferation |
|---|---|---|---|
| Example 16 | 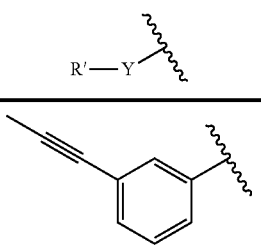 | 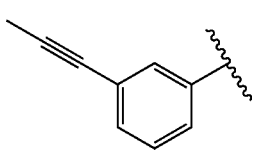 [SMILES: *c1cccc(C#CC)c1] | 0.0088 |
| Example 18 | 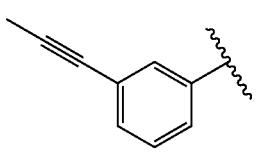 [SMILES: *c1cccc(C#CC)c1] | 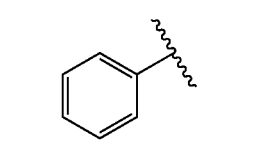 [SMILES: *c1ccccc1] | 0.0042 |
| Example 19 | 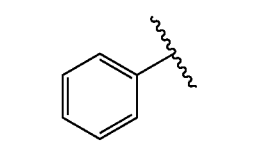 [SMILES: *c1ccccc1] | 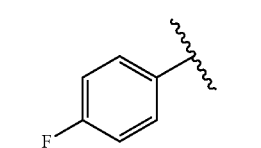 | 0.026 |
| Comparative example 1 | 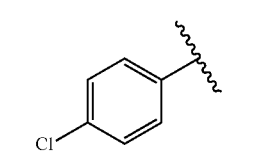 [SMILES: *c1ccc(Cl)cc1] | 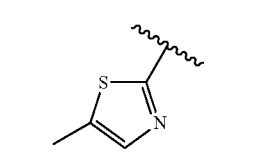 [SMILES: *c1ncc(C)s1] | >1.0 |
| Comparative example 2 | 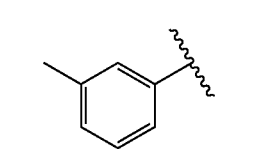 [SMILES: *c1cccc(C)c1] | 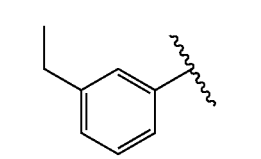 [SMILES: *c1cccc(CC)c1] | 0.97 |
| Comparative example 3 | | | >1.0 |
| Comparative example 4 | | | >1.0 |
| Comparative example 5 | | | >1.0 |
| Comparative example 6 | | | 0.58 |
| Comparative example 7 | | | 0.88 |

TABLE 2-continued

| Test compound No. | R'—Y | Z' | IC$_{50}$ value (nM) of inhibition effect of pulmonary fibroblast proliferation |
|---|---|---|---|
| Comparative example 8 | propyl-phenyl | 2-methylpyridine | 0.34 |
| Comparative example 9 | butenyl-phenyl | 2-methylpyridine | 0.75 |
| Comparative example 10 | allyl-phenyl | 2-methylpyridine | 0.56 |
| Comparative example 16 | ethynyl-phenyl (ortho) | 2-methylpyridine | 0.50 |
| Comparative example 17 | propynyl-phenyl (para) | 2-methylpyridine | >1.0 |

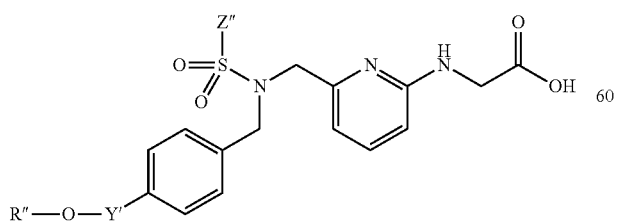

TABLE 3
| Test compound No. | R″—O—Y′ | Z″ | IC$_{50}$ value (nM) of inhibition effect of pulmonary fibroblast proliferation |
|---|---|---|---|
| Example 7 | 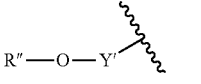 | 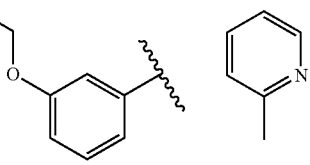 | 0.028 |
| Example 9 | 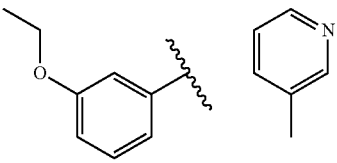 | 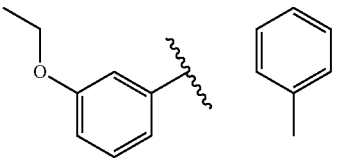 | 0.051 |
| Example 10 | 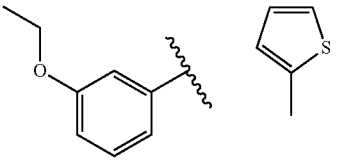 | 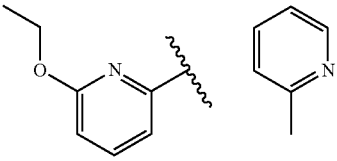 | 0.035 |
| Example 11 | 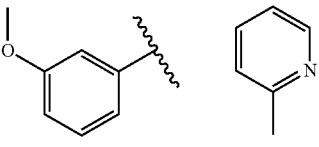 | 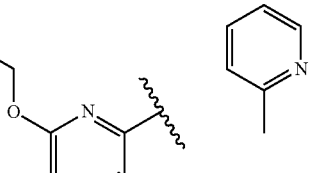 | 0.049 |
| Example 12 | 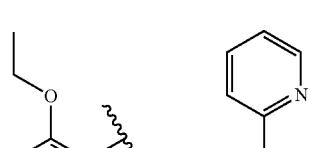 | | 0.037 |
| Comparative example 11 | | | 0.20 |
| Comparative example 12 | | | 0.44 |
| Comparative example 13 | | | >1.0 |

TABLE 3-continued

| Test compound No. | R″—O—Y″ ⌇⌇ Z″ | IC$_{50}$ value (nM) of inhibition effect of pulmonary fibroblast proliferation |
|---|---|---|
| Comparative example 14 | [4-ethoxyphenyl group] / [2-methylpyridin-? -yl] | >1.0 |
| Comparative example 15 | [2-ethoxypyridin-4-yl group] / [2-methylpyridin-?-yl] | >1.0 |

In this test, compounds of the present invention demonstrated superior inhibition effect of pulmonary fibroblast proliferation.

Test Example 3

Test for Inhibition of Pulmonary Fibrosis in Mouse

Test for inhibition effect of pulmonary fibrosis using mouse was performed by partially modifying the method of Oku et al. (European Journal of Pharmacology, 590, 400 (2008)). That is, ICR mice (male, 12-15 weeks old, supplied by Charles River Laboratories Japan, Inc.) were subjected to intravenous administration (10 mg/kg) of bleomycin (Bleo for Injection 15 mg, manufactured by Nippon Kayaku Co., Ltd.) dissolved in saline for 5 consecutive days to prepare mouse pulmonary fibrosis models. These models were used as a bleomycin control group and a test compound administration group. Similarly, a normal group was subjected to administration of saline for 5 days. For the test, each group used 7 or more mice.

The test compound solution for the administration was prepared by dissolving the test substance to the equimolar amount of 0.1 mol/L aqueous sodium hydroxide solution, and then neutralizing by adding a phosphate buffer solution (PBS) which was a medium. The test compound was administered via intratracheal administration twice per day from the start date of the test, for 28 days. For the normal group and bleomycin control group, the medium was administered similarly via intratracheal administration. For the intratracheal administration, the MicroSprayer™ (IA-1C-M, manufactured by PennCentury) was used.

On the day following the completion of 28-day administration, the mice were left bleeding to die while subjecting the mice for inhalation anesthesia, to collect the lungs. To the collected lungs, 0.5 mL of 6 mol/L hydrochloric acid was added, and the lungs were treated using a homogenizer (FastPrep-24, available from Funakoshi Co., Ltd.) to prepare lung homogenates. The lung homogenates were subjected to heat treatment (105-110° C., for approximately 30 hours) to obtain yellow crude hydrolysis solutions. The solutions were filtrated with a filter (Minisart RC4, 0.45 μm, manufactured by Sartorius) to obtain lung hydrolysis solutions.

The amount of hydroxyproline (HYP) in the lung hydrolysis solution, which is an indicator of collagen accumulation, was measured by the method of Woessner et al. (Archives of Biochemistry and Biophysics, 93, 440 (1961)). In a test tube, the lung hydrolysis solution described above and the same amount of 6 mol/L aqueous sodium hydroxide solution were added to neutralize, and then 0.3 mol/L aqueous sodium chloride solution was added to make the total volume to be 1 mL. Then the solution was sequentially treated with 0.5 mL of chloramine-T solution (room temperature, for 20 minutes) and 0.5 mL of perchloric acid solution (room temperature, for 5 minutes or longer), and then 0.5 mL of p-dimethylaminobenzaldehyde solution was added and heated (60° C., for 20 minutes) to develop a color. After cooling, 200 μL of the colored solution was placed on a microplate, and the absorbance (measurement wavelength: 570 nm, reference wavelength: 620 nm) was measured using a plate reader (SPECTRA FLOUR, manufactured by Tecan). A HYP solution having a specified concentration was reacted in the same manner to create a calibration curve, and the HYP concentration of each sample was calculated. From the calculated HYP concentration, the amount of HYP in the lung per 100 g of body weight was calculated. The inhibiting rate of HYP formation in the lung upon administration of the test compound was calculated using the formula described below.

Inhibiting rate (%)=[(HYP$b$−HYP$c$)/(HYP$b$−HYP$n$)]×100

HYPb: amount of HYP in the lung per 100 g of body weight for the bleomycin control group
HYPc: amount of HYP in the lung per 100 g of body weight for the test compound administration group
HYPn: amount of HYP in the lung per 100 g of body weight for the normal group In this test, for example, the compounds of Examples 4, 10, and 16 of the present invention exhibited 70% or greater inhibiting rate at the dose of 0.3 mg/kg and demonstrated excellent inhibition effect of pulmonary fibrosis.

Test Example 4

Metabolism Test Using Human Lung Microsomal Fraction

To 990 μL of reaction composition solution (150 μL of NADPH formation system solution A (manufactured by Corning), 10 μL of NADPH formation system solution B (manufactured by Corning), 86 μL of 0.5 mol/L phosphate buffer solution (pH 7.4), and 394 μL of distilled water) in which human lung microsomes (manufactured by Xenotech) equivalent to 3.5 mg of protein was suspended, 10 μL of the test compound dissolved in dimethyl sulfoxide (final concentration: 1.0 (V/V) %) was added and incubated at 37° C. for 20 minutes. Using a high performance liquid chromatography (LC-20A series, manufactured by Shimadzu Corporation), peak areas (measurement UV wavelength: 245 nm) for the test compound (unchanged ester) and for carboxylic acid, which was the formed pharmacologically active compound, were calculated, and the formation rate of carboxylic acid was calculated by the formula described below.

HPLC condition; column: Phenomenex Kinetex C18, 2.1 mm×100 mm, 2.6 μm, Column temperature: 40° C., Eluents; A: 0.1% formic acid, B solution: acetonitrile/methanol/formic acid=500/500/1, Gradient condition; 0→3 minutes: A solution 80%, 3→11 minutes: A solution 20%→5%, 11→15 minutes: A solution 5%, Analysis time: 20 minutes)

Formation rate of carboxylic acid (after 20 minutes of the reaction) %=peak area for carboxylic acid after 20 minutes of the reaction/peak area for the test compound after 0 minutes of the reaction×100

The test results are shown in Table 4.

TABLE 4

| Test compound No. | Formation rate of carboxylic acid (%) |
|---|---|
| Example 3 | 27 |
| Example 20 | 35 |

In this test, the ester compound of the present invention was quickly transformed to carboxylic acid form which is a pharmacologically active form.

Representative preparation examples used in the present invention are described below.

Preparation Example 1: Hard Capsule 50 mg of powdered compound of Example 2, 128.7 mg of lactose, 70 mg of cellulose, and 1.3 mg of magnesium stearate are mixed and passed through a 60 mesh sieve followed by placing 250 mg of this powder in a No. 3 gelatin capsule to obtain a capsule preparation.

Preparation Example 2: Tablet 50 mg of the compound of Example 2, 124 mg of lactose, 25 mg of cellulose, and 1 mg of magnesium stearate are mixed and formed into a tablet with a tablet-making machine to obtain a tablet weighing 200 mg of the mixture per tablet. This tablet can be provided with a sugar coating as necessary.

INDUSTRIAL APPLICABILITY

The substituted biaryl compound of general formula (I) or the pharmacologically acceptable salt thereof of the present invention is useful as pharmaceuticals, especially as a therapeutic agent and/or prophylactic agent for interstitial pneumonia and pulmonary fibrosis, by exhibiting EP2 agonistic effect and excellent inhibition effect of pulmonary fibroblast proliferation.

The invention claimed is:
1. A substituted biaryl compound of general formula (I):

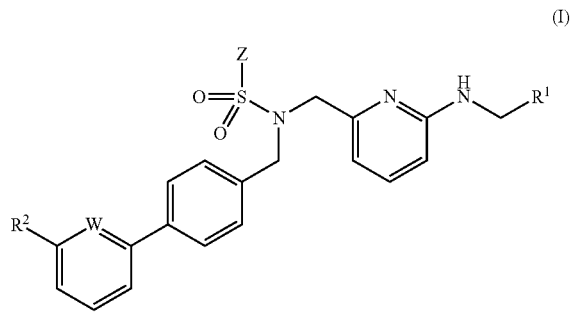

wherein,
$R^1$ represents —$CO_2H$ or —$CO_2R^{1'}$, wherein $R^{1'}$ is selected from $C_1$-$C_{12}$ alkyl groups, $C_7$-$C_{18}$ aralkyl groups, $C_1$-$C_4$ alkyl groups substituted with a $C_2$-$C_5$ alkanoyloxy group, $C_1$-$C_4$ alkyl groups substituted with a ($C_1$-$C_4$ alkoxy)carbonyloxy group, N,N-dimethylaminocarbonylmethyl group, N,N-diethylaminocarbonylmethyl group, 2-(N,N-dimethylamino)ethyl group, 2-(N,N-diethylamino)ethyl group, 2-(morpholin-4-yl) ethyl group, 2-piperidinoethyl group, 2-(4-methylpiperidino)ethyl group, (5-methyl-2-oxo-1,3-dioxolen-4-yl)methyl group, and (5-phenyl-2-oxo-1,3-dioxolen-4-yl)methyl group, W represents a nitrogen atom or —CH= group,
$R^2$ represents 1 propenyl group or 1-propynyl group, and
Z represents a phenyl group, 3-fluorophenyl group, pyridin-2-yl group, pyridin-3-yl group, thiophen-2-yl group, or thiophen-3-yl group;
or a pharmacologically acceptable salt thereof.

2. The substituted biaryl compound according to claim 1, wherein $R^1$ represents a carboxy group or $C_1$-$C_6$ alkoxycarbonyl group,
or a pharmacologically acceptable salt thereof.

3. The substituted biaryl compound according to claim 1, wherein $R^1$ represents a carboxy group, ethoxycarbonyl group, isopropoxycarbonyl group, or hexyloxycarbonyl group,
or a pharmacologically acceptable salt thereof.

4. The substituted biaryl compound according to claim 1, wherein $R^1$ represents a carboxy group, ethoxycarbonyl group, isopropoxycarbonyl group, or hexyloxycarbonyl group,
W represents a nitrogen atom or —CH= group,
and
Z represents a phenyl group, 3-fluorophenyl group, pyridin-2-yl group, pyridin-3-yl group, thiophen-2-yl group, or thiophen-3-yl group,
or a pharmacologically acceptable salt thereof.

5. The substituted biaryl compound according to claim 1, wherein the substituted biaryl compound is
ethyl (6-{[3'-(1-propenyl)biphenyl-4-ylmethyl](pyridin-2-ylsulfonyl)-aminomethyl}pyridin-2-ylamino)acetate,
(6-{[3'-(1-propenyl)biphenyl-4-ylmethyl](pyridin-2-ylsulfonyl)aminomethyl}pyridin-2-ylamino)acetic acid,
ethyl (6-{[3'-(1-propynyl)biphenyl-4-ylmethyl](pyridin-2-ylsulfonyl)-aminomethyl}pyridin-2-ylamino)acetate,
(6-{[3'-(1-propynyl)biphenyl-4-ylmethyl](pyridin-2-ylsulfonyl)aminomethyl}pyridin-2-ylamino)acetic acid, ethyl (6-{[3'-(1-propynyl)biphenyl-4-ylmethyl](pyridin-3-ylsulfonyl)-aminomethyl}pyridin-2-ylamino)acetate, (6-{[3'-(1-propynyl)biphenyl-4-ylmethyl](pyridin-3-ylsulfonyl)aminomethyl}pyridin-2-ylamino)acetic acid, ethyl (6-{[3'-(1-propynyl)biphenyl-4-ylmethyl](thiophen-2-ylsulfonyl)-aminomethyl}pyridin-2-ylamino)acetate, (6-{[3'-(1-propynyl)biphenyl-4-ylmethyl](thiophen-2-ylsulfonyl)aminomethyl}pyridin-2-ylamino)acetic acid, ethyl (6-{(benzenesulfonyl)[3'-(1-propynyl)biphenyl-4-ylmethyl]-aminomethyl}pyridin-2-ylamino)acetate, (6-{(benzenesulfonyl)[3'-(1-propynyl)biphenyl-4-ylmethyl]aminomethyl}pyridin-2-ylamino)acetic acid, ethyl (6-{[3'-(1-propynyl)biphenyl-4-ylmethyl](thiophen-3-ylsulfonyl)-aminomethyl}pyridin-2-ylamino)acetate, (6-{[3'-(1-propynyl)biphenyl-4-ylmethyl](thiophen-3-ylsulfonyl)aminomethyl}pyridin-2-ylamino)acetic acid, (6-{(3-fluorobenzenesulfonyl)[3'-(1-propynyl)biphenyl-4-ylmethyl]-aminomethyl}pyridin-2-ylamino)acetic acid, or isopropyl (6-{[3'-(1-propynyl)biphenyl-4-ylmethyl](pyridin-2-ylsulfonyl)-aminomethyl}pyridin-2-ylamino)acetate, or a pharmacologically acceptable salt thereof.

6. A pharmaceutical composition comprising the substituted biaryl compound according to claim 1, or a pharmacologically acceptable salt thereof, as an active ingredient.

7. A method for treating interstitial pneumonia and/or pulmonary fibrosis in a subject in need thereof, comprising administering to the subject a therapeutically effective amount of a pharmaceutical composition comprising the substituted biaryl compound according to claim 1, or a pharmacologically acceptable salt thereof, as an active ingredient.

* * * * *